(12) United States Patent
Numata et al.

(10) Patent No.: US 9,199,974 B2
(45) Date of Patent: Dec. 1, 2015

(54) MATERIAL FOR ORGANIC ELECTROLUMINESCENT DEVICE AND ORGANIC ELECTROLUMINESCENT DEVICE USING SAME

(75) Inventors: Masaki Numata, Chiba (JP); Hideaki Nagashima, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 13/027,844

(22) Filed: Feb. 15, 2011

(65) Prior Publication Data

US 2011/0278552 A1 Nov. 17, 2011

(30) Foreign Application Priority Data

Mar. 31, 2010 (JP) .................................. 2010-084476

(51) Int. Cl.
| | | |
|---|---|---|
| H01L 51/54 | (2006.01) | |
| C07D 407/14 | (2006.01) | |
| C07D 407/10 | (2006.01) | |
| C07D 405/14 | (2006.01) | |
| C07D 209/86 | (2006.01) | |
| C07D 403/10 | (2006.01) | |
| C07D 405/04 | (2006.01) | |
| C09K 11/06 | (2006.01) | |
| H01L 51/00 | (2006.01) | |
| H05B 33/14 | (2006.01) | |
| H05B 33/20 | (2006.01) | |
| H01L 51/50 | (2006.01) | |

(52) U.S. Cl.
CPC ............ *C07D 405/14* (2013.01); *C07D 209/86* (2013.01); *C07D 403/10* (2013.01); *C07D 405/04* (2013.01); *C09K 11/06* (2013.01); *H01L 51/0062* (2013.01); *H05B 33/14* (2013.01); *H05B 33/20* (2013.01); *C09K 2211/1029* (2013.01); *C09K 2211/1044* (2013.01); *C09K 2211/1059* (2013.01); *C09K 2211/1074* (2013.01); *C09K 2211/1092* (2013.01); *C09K 2211/185* (2013.01); *H01L 51/5012* (2013.01)

(58) Field of Classification Search
None
See application file for complete search history.

(56) References Cited

U.S. PATENT DOCUMENTS

| 7,504,769 B2* | 3/2009 | Radu et al. .................... 313/504 |
| 2003/0184221 A1* | 10/2003 | Mishima ....................... 313/512 |
| 2007/0278938 A1* | 12/2007 | Yabunouchi et al. ......... 313/504 |
| 2008/0238305 A1 | 10/2008 | Kondo et al. |
| 2009/0302745 A1* | 12/2009 | Otsu et al. ..................... 313/504 |
| 2010/0045172 A1 | 2/2010 | Hiyama et al. |
| 2010/0127246 A1* | 5/2010 | Nakayama et al. ............. 257/40 |
| 2011/0260138 A1* | 10/2011 | Xia et al. ......................... 257/40 |

FOREIGN PATENT DOCUMENTS

| JP | 2004-311413 A | 11/2004 | |
| JP | 2008-84913 | 4/2008 | |
| JP | 2008-523049 | 7/2008 | |
| JP | 2008-181937 | 8/2008 | |
| JP | 2008-227462 A | 9/2008 | |
| JP | 2008-270190 | 11/2008 | |
| JP | 2009-84622 A | 4/2009 | |
| JP | 2009-94124 A | 4/2009 | |
| JP | 2010-21336 | 1/2010 | |
| JP | 2010-40830 | 2/2010 | |
| WO | WO 2007/043484 | 4/2007 | |
| WO | WO 2007/108327 A1 | 9/2007 | |
| WO | WO 2007/119816 A1 * | 10/2007 | .............. H01L 51/50 |
| WO | WO 2008/029652 A1 | 3/2008 | |
| WO | WO 2008/029729 A1 | 3/2008 | |
| WO | WO 2008/120611 A1 | 10/2008 | |
| WO | WO 2008/132965 A1 | 11/2008 | |
| WO | WO 2008/140114 A | 11/2008 | |
| WO | WO 2009/060742 A1 | 5/2009 | |
| WO | WO 2010/004877 A1 | 1/2010 | |

OTHER PUBLICATIONS

Vaitkeviciene et al. (Synthetic Materials 158 (2008) 383-390).*
Machine English translation of JP 2010-021336 A. Jul. 3, 2012.*
International Search Report issued Apr. 5, 2011, in PCT/JP2011/053055.
Office Action issued Feb. 5, 2013 in Japanese Application No. 2012-508130.
Japanese Office Action issued Apr. 22, 2014, in Japan Patent Application No. 2013-094610.
Office Action issued Sep. 24, 2014 in Japanese Patent Application No. 2012-509494.

* cited by examiner

*Primary Examiner* — J. L. Yang
(74) *Attorney, Agent, or Firm* — Oblon, McClelland, Maier & Neustadt, L.L.P.

(57) ABSTRACT

The present invention provides a material for an organic electroluminescence device having a specific structure in which a dibenzofuranyl group or a dibenzothiophenyl group is bonded at an N-position (9-position) of a carbazolyl group and an organic electroluminescence device which is provided with one or more organic thin film layers including a light emitting layer between a cathode and an anode and in which at least one layer of the organic thin film layers described above contains the material for an organic electroluminescence device according to the present invention.

14 Claims, No Drawings

MATERIAL FOR ORGANIC ELECTROLUMINESCENT DEVICE AND ORGANIC ELECTROLUMINESCENT DEVICE USING SAME

BACKGROUND OF THE INVENTION

1. Technical Field

The present invention relates to a material for an organic electroluminescence device and an organic electroluminescence device prepared by using the same.

2. Background Art

An organic electroluminescence device (hereinafter "electroluminescence" shall be abbreviated as EL) is a spontaneous light emitting device making use of the principle that a fluorescent substance or a phosphorescent substance emits light by recombination energy of holes injected from an anode and electrons injected from a cathode by applying an electric field. Since a laminate type organic EL device operated at a low voltage was reported, researches on organic EL devices comprising organic materials as structural materials have actively been carried out. In the above laminate type device, tris(8-quinolinolate)aluminum is used for the light emitting layer, and a tetraphenyldiamine derivative is used for the hole transporting layer. The advantages of the laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layer type comprising a hole transporting (injecting) layer, a light emitting layer and an electron transporting (injecting) layer are well known as the device structures of an organic EL device. In the above laminate type structural devices, device structures and forming methods are studied in order to enhance a recombination efficiency of holes and electrons injected.

Known as light emitting materials for an organic EL device are light emitting materials such as chelate complexes such as a tris(8-quinolinolate)aluminum complex and the like, coumarin derivatives, tetraphenylbutadiene derivatives, distyrylarylene derivatives, oxadiazole derivatives and the like. It is reported that light emission of a blue color to a red color in a visible region is obtained from the above light emitting materials, and color display devices are materialized.

Fluorescent materials which emit light by a singlet exciton have so far been used as light emitting materials for an organic EL device. In recent years, it is proposed to make use of phosphorescence luminescence materials which emit light by a triplet exciton in addition to fluorescent materials (for example, non-patent documents 1 and 2). It is considered that when an electron is recombined with a hole in an organic EL device, singlet excitons and triplet excitons are formed in a proportion of 1:3 due to a difference thereof in a spin multiplicity, and therefore an organic EL device prepared by using a phosphorescence luminescence material can achieve a luminous efficiency which is larger by three to four times as compared with that of an organic EL device prepared by using only a fluorescent material. In blue color phosphorescent emission, however, it is difficult to achieve the high efficiency and the long lifetime, and a host material which achieves them is desired to be developed.

A compound to which two carbazole skeletons are bonded via linkage groups is proposed in a patent document 1. A compound in which two carbazole skeletons are bonded to one dibenzofuran skeleton or dibenzothiophene skeleton is proposed in a patent document 2 (for example, compounds 23 and 24). A compound in which two carbazole skeletons are bonded to one dibenzofuran skeleton is proposed in a patent document 3 (for example, compound 43).

However, compounds which have two carbazole skeletons and to which a dibenzofuran skeleton or a dibenzothiophene skeleton is bonded at sites of N in the respective skeletons, if necessary, via linkage groups are not described in the above documents.

Further, the compounds described in the patent documents 1 to 3 were unsatisfactory in an efficiency and a lifetime in blue color phosphorescent emission.

Patent document 1: WO2007/108459
Patent document 2: WO2007/119816
Patent document 3: WO2007/077810
Non-patent document 1: Applied Physics Letters Vol. 74, No. 3, pp. 442 to 444
Non-patent document 2: Applied Physics Letters Vol. 75, No. 1, pp. 4 to 6

SUMMARY OF THE INVENTION

Problems to be Solved by the Invention

The present invention has been made in order to solve the problems described above, and an object of the present invention is to provide an organic EL device having a high efficiency and a long lifetime in phosphorescent emission and a material for an organic EL device which materializes the same.

Means for Solving the Problems

Intense researches repeated by the present inventors in order to achieve the object described above have resulted in finding that the constitution of a compound represented by Formula (1) shown below makes it possible to generate phosphorescent emission at a high efficiency because of a reason described later when it is used as a material for an organic EL device and extend a lifetime of the device, and thus they have come to complete the present invention.

That is, the present invention relates to a material for an organic electroluminescence device represented by Formula (1) shown below:

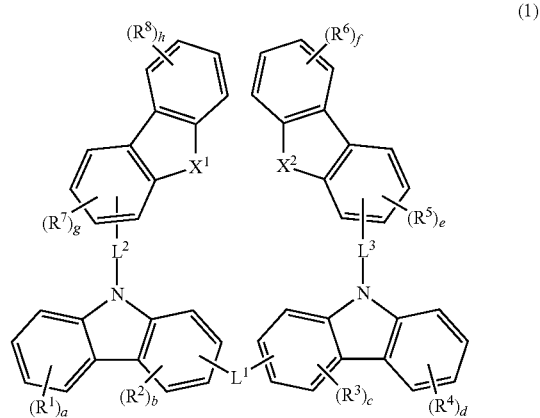

(in Formula (1), $X^1$ and $X^2$ each are independently an oxygen atom or a sulfur atom, and they are not a sulfur atom at the same time; $R^1$ to $R^8$ each represent independently an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group or a cyano group, and the above substituents $R^1$ to $R^8$ may be further substituted with the above substituents; when $R^1$ to $R^8$ each are present in a plural number, they may be the same as or different from each other;

a, d, f and h each represent independently an integer of any of 0 to 4, and b, c, e and g each represent independently an integer of any of 0 to 3; a sum of a to h is 6 or less;

$L^1$ represents a single bond, a divalent linkage group containing N, a divalent linkage group containing O, a divalent linkage group containing Si, a divalent linkage group containing P, a divalent linkage group containing S, an alkylene group having 1 to 20 carbon atoms, a cycloalkylene group having 3 to 20 ring carbon atoms, an arylene group having 6 to 18 ring carbon atoms, a heteroarylene group having 5 to 18 ring atoms, a divalent amino group or a divalent silyl group;

$L^2$ and $L^3$ each represent independently a single bond, an alkylene group having 1 to 20 carbon atoms, a cycloalkylene group having 3 to 20 ring carbon atoms, an arylene group having 6 to 18 ring carbon atoms or a heteroarylene group having 5 to 18 ring atoms; $L^1$ to $L^3$ may be further substituted with any of the substituents $R^1$ to $R^8$ described above; provided that when $L^1$ is an arylene group having 6 to 18 ring carbon atoms or a heteroarylene group having 5 to 18 ring atoms, a and d each represent independently an integer of any of 1 to 4).

Further, the present invention relates to an organic electroluminescence device which is provided with one or more organic thin film layers including a light emitting layer between a cathode and an anode and in which at least one layer of the organic thin film layers described above contains the material for an organic electroluminescence device represented by Formula (1) described above.

Effect of the Invention

According to the present invention, an organic EL device having a high efficiency in phosphorescent emission and a long lifetime and a material for an organic EL device which materializes the same can be provided.

EMBODIMENTS FOR CARRYING OUT THE INVENTION

The material for an organic electroluminescence device according to the present invention is represented by Formula (1) shown below:

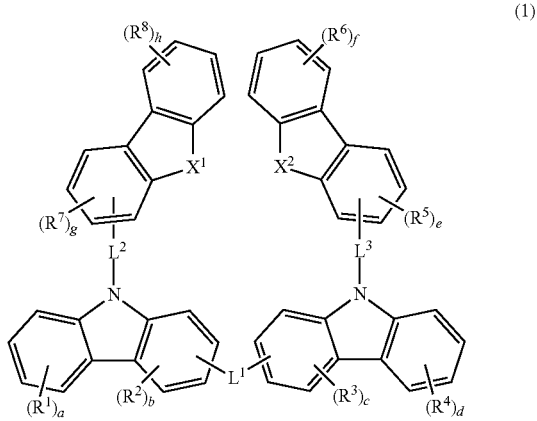

(1)

(in Formula (1), $X^1$ and $X^2$ each are independently an oxygen atom or a sulfur atom, and they are not a sulfur atom at the same time (that is, $X^1$ and $X^2$ are an oxygen atom or one of them is an oxygen atom, and the other is a sulfur atom); $R^1$ to $R^8$ each represent independently an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group or a cyano group, and the above substituents $R^1$ to $R^8$ may be further substituted with the above substituents (hereinafter referred to as "the substituents R" as a whole); when $R^1$ to $R^8$ each are present in a plural number, they may be the same as or different from each other;

a, d, f and h each represent independently an integer of any of 0 to 4, and b, c, e and g each represent independently an integer of any of 0 to 3; a sum of a to h is 6 or less;

$L^1$ represents a single bond, a divalent linkage group containing N, a divalent linkage group containing O, a divalent linkage group containing Si, a divalent linkage group containing P, a divalent linkage group containing S, an alkylene group having 1 to 20 carbon atoms, a cycloalkylene group having 3 to 20 ring carbon atoms, an arylene group having 6 to 18 ring carbon atoms, a heteroarylene group having 5 to 18 ring atoms, a divalent amino group or a divalent silyl group;

$L^2$ and $L^3$ each represent independently a single bond, an alkylene group having 1 to 20 carbon atoms, a cycloalkylene group having 3 to 20 ring carbon atoms, an arylene group having 6 to 18 ring carbon atoms or a heteroarylene group having 5 to 18 ring atoms; $L^1$ to $L^3$ may be further substituted with any of the substituents R described above; provided that when $L^1$ is an arylene group having 6 to 18 ring carbon atoms or a heteroarylene group having 5 to 18 ring atoms, a and d each represent independently an integer of any of 1 to 4).

In particular, bonding of a dibenzofuranyl group or a dibenzothiophenyl group at an N-position (9-position) of a carbazolyl group directly or via a bonding group as shown in Formula (1) elevates a LUMO sequence of dibenzofrane or dibenzothiophene and makes it easy to inject electrons into a light emitting layer and the like in the organic EL device prepared by using the material for an organic electroluminescence device according to the present invention. This makes it possible to facilitate controlling the carrier balance, and the effects of the present invention are exerted well.

The alkyl group represented by $R^1$ to $R^8$ includes methyl, ethyl, propyl, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, neopentyl, 1-methylpentyl, 2-methylpentyl, 1-pentylhexyl, 1-butylpentyl, 1-heptyloctyl, 3-methylpentyl and the like.

The examples of the cycloalkyl group represented by $R^1$ to $R^8$ include cyclopropyl, cyclobutyl, cyclopentyl, cyclohexyl, cycloheptyl, norbornyl, adamantyl and the like.

The alkoxy group represented by $R^1$ to $R^8$ includes methoxy, ethoxy, propoxy, butoxy, pentyloxy, hexyloxy and the like, and the groups having 3 or more carbon atoms may be linear, cyclic or branched.

The cycloalkoxy group represented by $R^1$ to $R^8$ includes cyclopentoxy, cyclohexyloxy and the like.

The aryl group represented by $R^1$ to $R^8$ includes phenyl, tolyl, xylyl, mesityl, o-biphenyl, m-biphenyl, p-biphenyl, o-terphenyl, m-terphenyl, p-terphenyl, naphthyl, phenanthryl and the like. Among them, phenyl and mesityl are preferred.

The aryloxy group represented by $R^1$ to $R^8$ includes, for example, phenoxy, biphenyloxy and the like.

The heteroaryl group represented by $R^1$ to $R^8$ includes carbazolyl, dibenzofuranyl, dibenzothiophenyl, pyrrolyl, furyl, thienyl, silolyl, pyridyl, quinolyl, isoquinolyl, benzofuryl, imidazolyl, pyrimidyl, selenophenyl, oxadiazolyl, triazolyl and the like.

The amino group and the silyl group represented by $R^1$ to $R^8$ may be substituted with the substituents which have already been described. The silyl group is preferably trimethylsilyl.

It is preferred that a, d, f and h each are independently an integer of any of 0 to 3, and they are more preferably an integer of any of 0 to 2. Also, it is preferred that b, c, e and g each are independently an integer of any of 0 to 2, and they are more preferably an integer of any of 0 to 1. Further, a sum of a to h is preferably 4 or less considering that if the sublimation property and the molecular weight are too large, thermal decomposition is liable to be brought about in vapor deposition.

The divalent linkage group containing N, the divalent linkage group containing O, the divalent linkage group containing Si, the divalent linkage group containing P and the divalent linkage group containing S each represented by $L^1$ include the following groups:

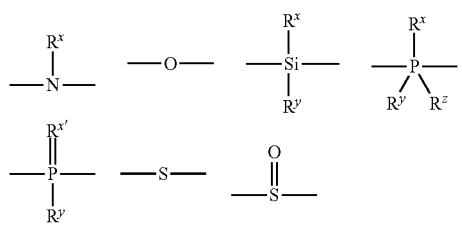

(in the respective formulas shown above, $R^x$, $R^Y$ and $R^z$ each are independently a hydrogen atom or a group selected from the substituents R described above; and $R^{x'}$ is oxygen). Among the groups described above, a "—S—" group, a phosphoxide group and an ether group are preferred.

The alkylene group, the cycloalkylene group having 3 to 20 ring carbon atoms, the arylene group having 6 to 18 ring carbon atoms, the heteroarylene group having 5 to 18 ring atoms, the divalent amino group or the divalent silyl group each represented by $L^1$ to $L^3$ include groups obtained by substituting hydrogen atoms of one of the substituents represented by $R^1$ to $R^8$ with bonding sites. Also, in the present invention, 9,9-fluorenylidene is included as well in the arylene group.

The arylene group is suitably p-phenylene, m-phenylene and biphenylene in addition to groups described later, and the amino group is suitably biphenylamino in addition to groups described later.

The linkage groups represented by $L^1$ to $L^3$ may further have substituents, and the above substituents are equivalent to the substituents explained in the substituents represented by $R^1$ to $R^8$.

The material for an organic EL device according to the present invention is preferably a host material or a hole-transporting material which is used together with the phosphorescence luminescence material. Also, an energy level of the triplet is preferably 2.0 eV or more, more preferably 2.5 eV or more.

The material for an organic EL device according to the present invention is preferably represented by the following Formula (2). A case in which two carbazolyl groups are bonded at a 3-position directly or via a linkage group as is the case with the following Formula (2) has the following advantages.

(1) The convenience in the synthesis is high.
(2) The 3- and 6-positions of carbazole are sites which are inferior in a chemical stability, and introduction of a substituent other than a hydrogen atom into even one of the 3- and 6-positions makes it possible to enhance the chemical stability. Accordingly, a structure in which a substituent is further introduced into the 6-position is more preferred.
(3) When carbazoles are combined at a 3-position via single bonds, N atoms on two carbazoles are conjugated to thereby make HOMO shallow, and the hole-injecting and transporting property can be elevated to make it easy to control the carrier balance.

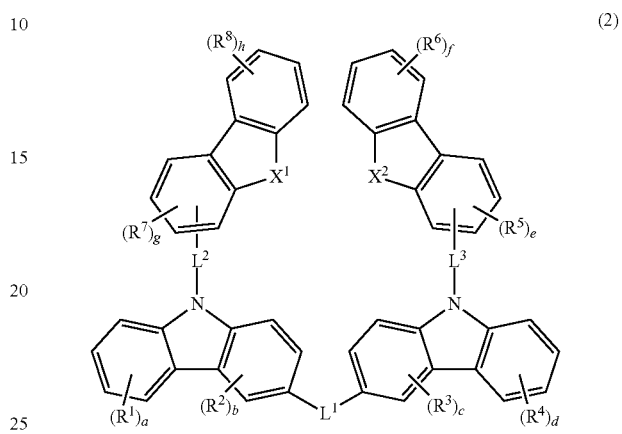

(in Formula (2), $X^1$ and $X^2$, $R^1$ to $R^8$, a to h and $L^1$ to $L^3$ are the same as described above).

Further, the material for an organic EL device according to the present invention is preferably represented by the following Formula (3) in terms of further enhancing a chemical stability.

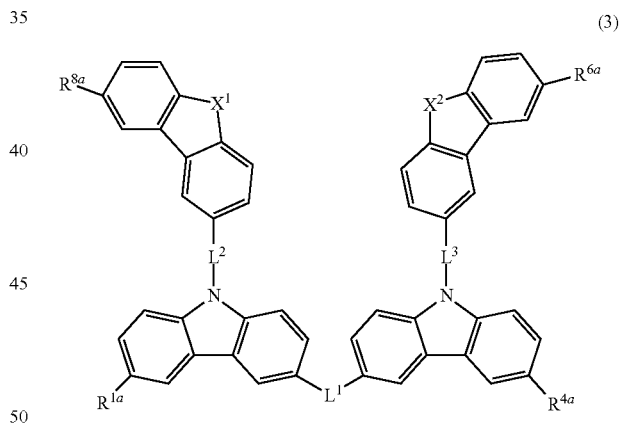

(in Formula (3), $R^{1a}$, $R^{4a}$, $R^{6a}$, and $R^{8a}$ each represent independently a hydrogen atom (corresponding to a case in which a, d, h and f in Formula (1) are 0) or an aryl group having 6 to 18 ring carbon atoms (the same aryl group as the substituent R described above), and the above aryl group may be substituted with the substituents R described above; and $X^1$, $X^2$ and $L^1$ to $L^3$ are the same as described above).

Further, $L^2$ and $L^3$ are preferably single bonds, and $L^1$ is preferably a single bond as well. This is because if the sublimation property and the molecular weight are too large, thermal decomposition is liable to be brought about in vapor deposition. Further, "$L^1$" and/or "$L^2$ and $L^3$" are preferably single bonds in terms of a reduction in the voltage and the half life. Also, $X^1$ and $X^2$ in Formulas (1) to (3) are preferably oxygen atoms in terms of the external quantum efficiency and the lifetime.

Further, Formula (3) is further preferably represented by the following Formula (3a) in terms of a reduction in the voltage and the half life:

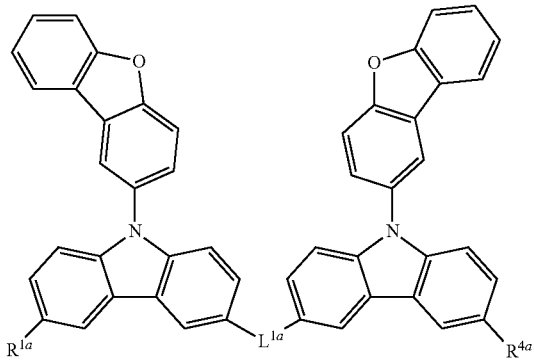

(3a)

(in Formula (3a), $R^{1a}$ and $R^{4a}$ each represent independently a hydrogen atom or a phenyl group which may be substituted with methyl; $L^{1a}$ is a single bond or a phenylene group; provided that a case in which both of $R^{1a}$ and $R^{4a}$ are hydrogen atoms and in which $L^{1a}$ is a phenylene group is excluded).

In a case in which both of $R^{1a}$ and $R^{4a}$ are hydrogen atoms and in which $L^{1a}$ is a phenylene group in Formula (3a) described above, a hydrogen atom is present at a 6-position of carbazole, and carbazoles are not bonded at a 3-position via a single bond. Accordingly, it is not a particularly excellent material as the material for an organic electroluminescence device in terms of a chemical stability and controlling of a carrier balance.

The specific examples of the material for an organic EL device represented by Formula (1) according to the present invention shall be shown below, but the present invention shall not be restricted to these compounds shown as the examples. Substituents shown in the following specific examples can be listed as the preferred substituents in the present invention.

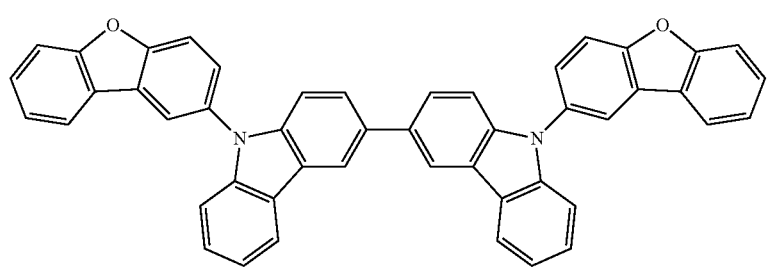

(1)

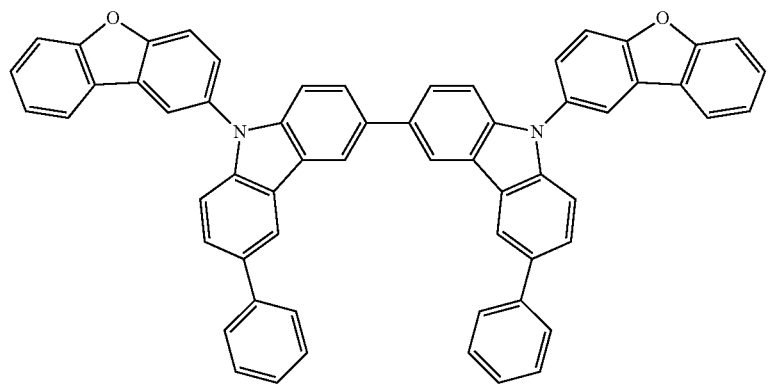

(2)

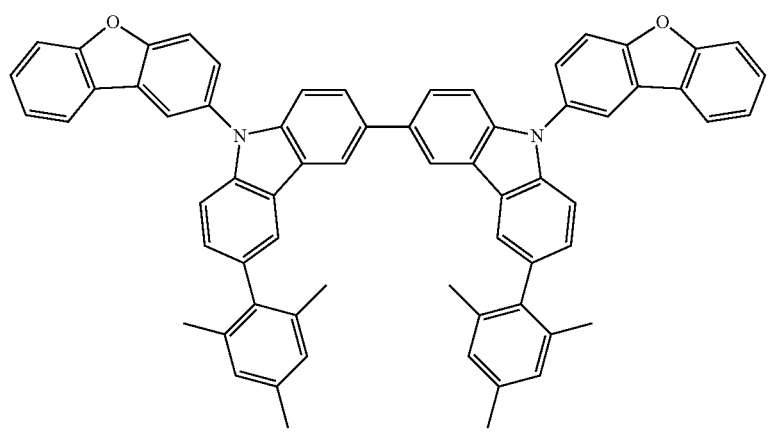

(3)

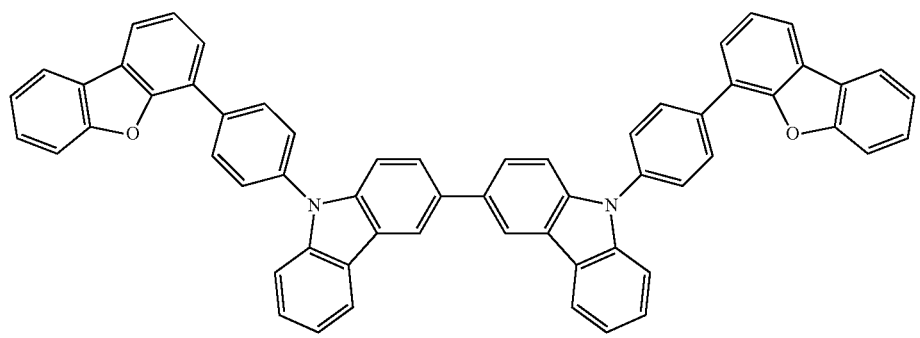
(4)
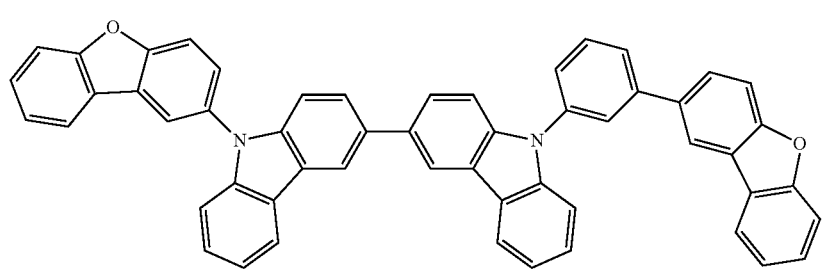
(5)
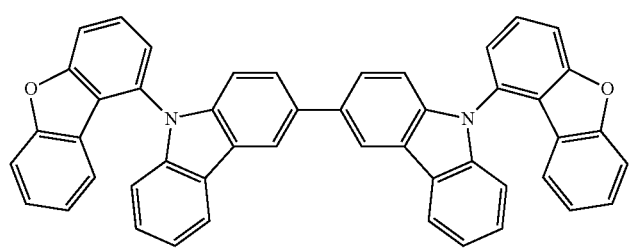
(6)
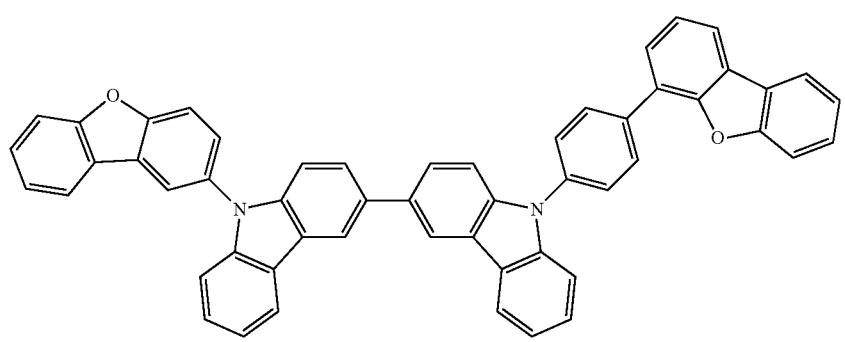
(7)

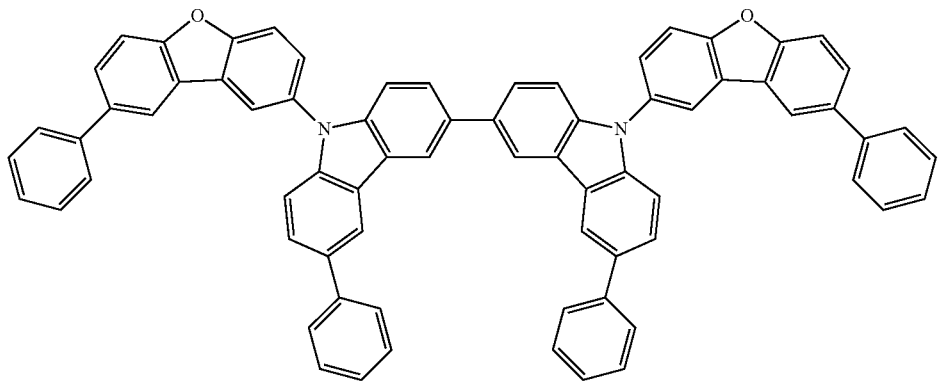
(8)
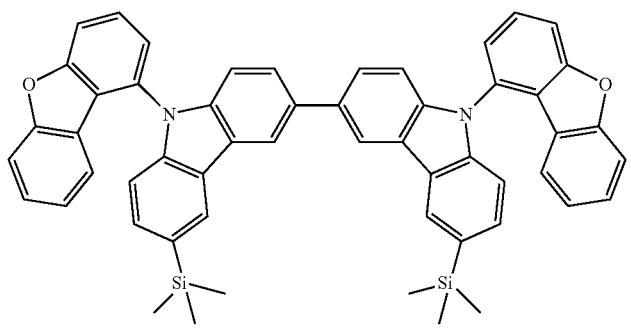
(9)
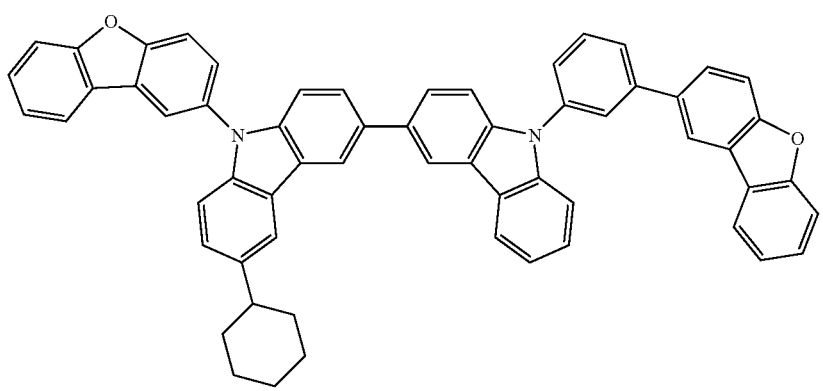
(10)
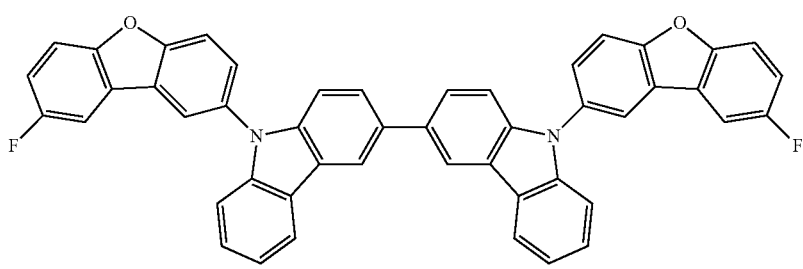
(11)

-continued
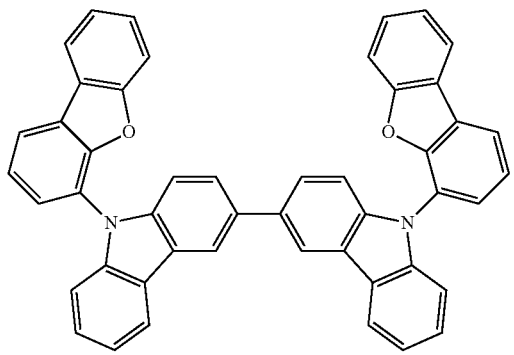
(12)
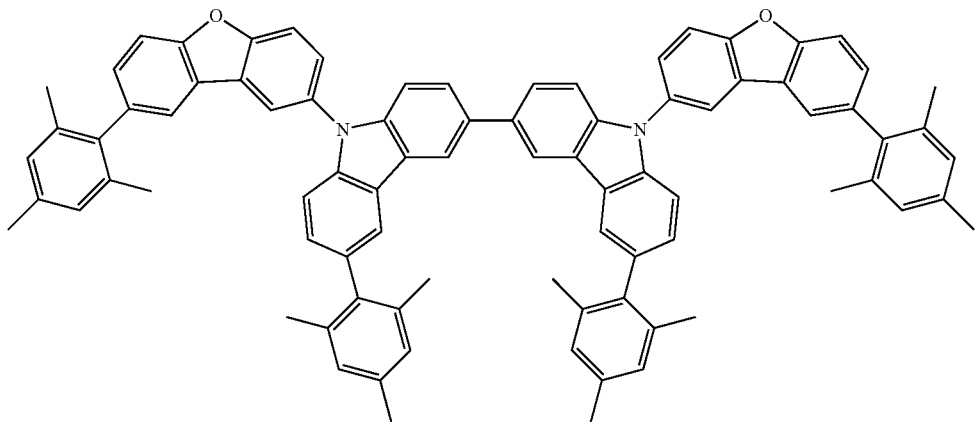
(13)
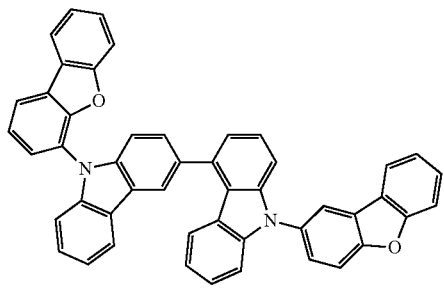
(14)
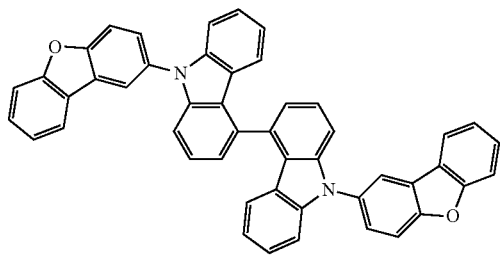
(15)

-continued
(16)
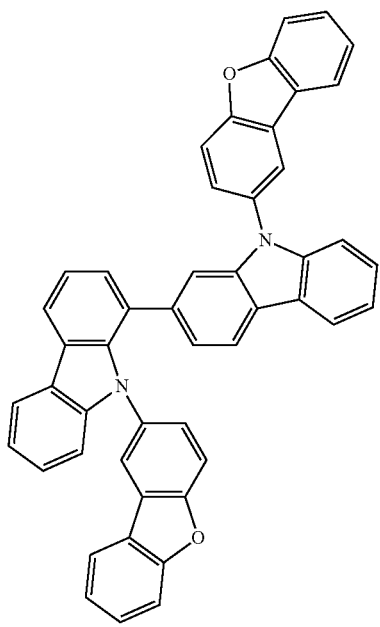
(17)
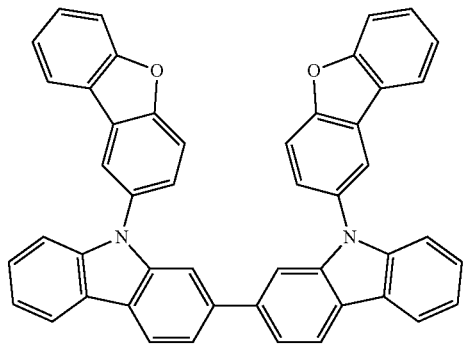
(18)
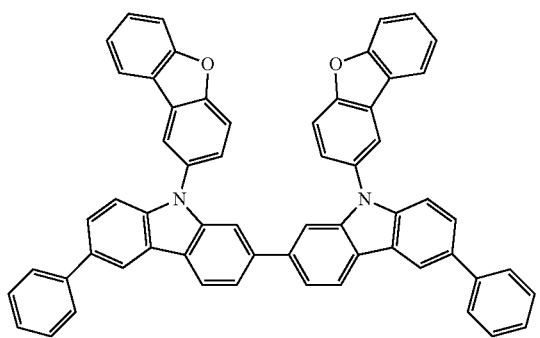
(19)
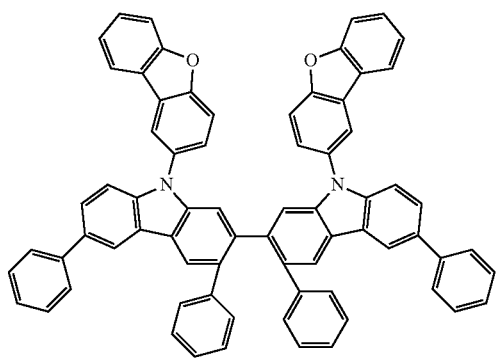
(20)
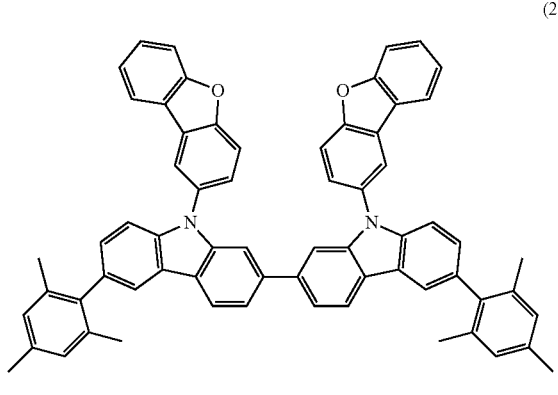
(21)
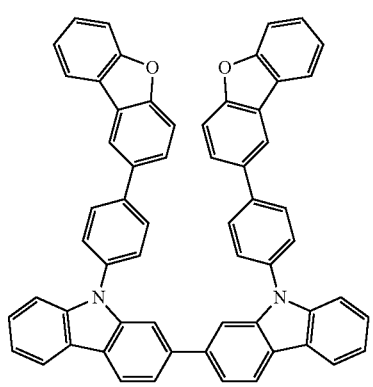

-continued
(22)
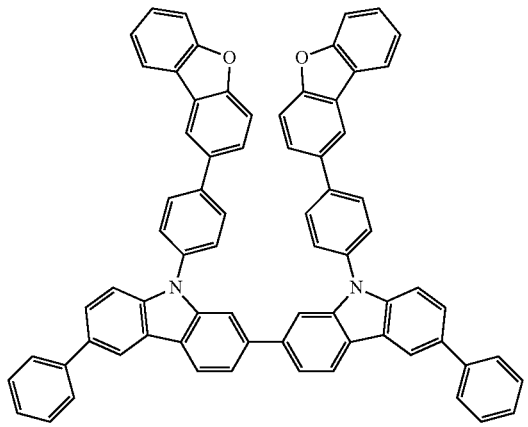
(23)
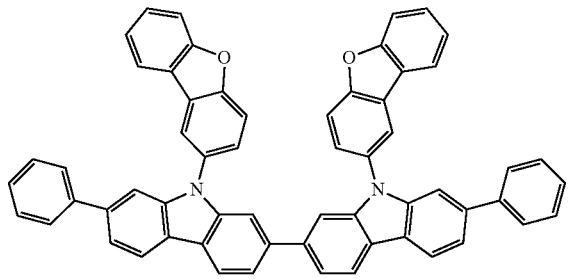
(24)
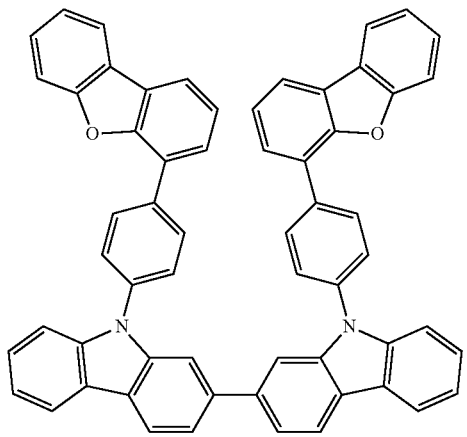
(25)
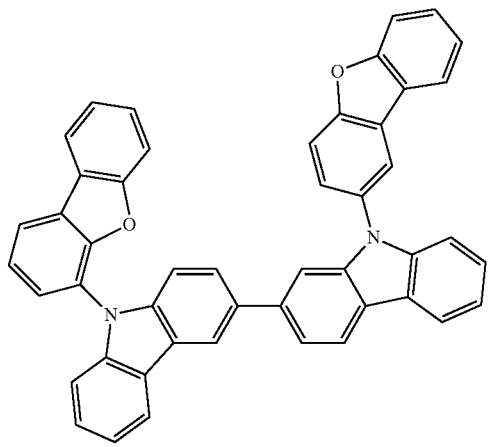
(26)
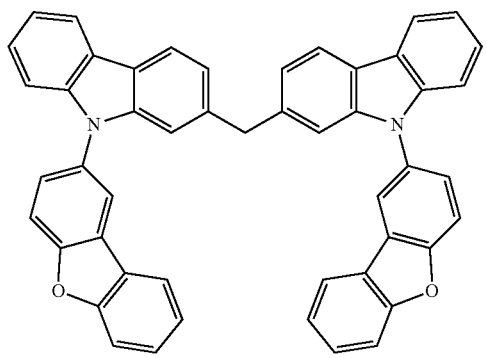
(27)
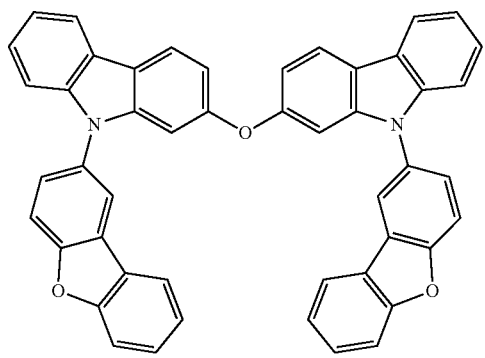
(28)
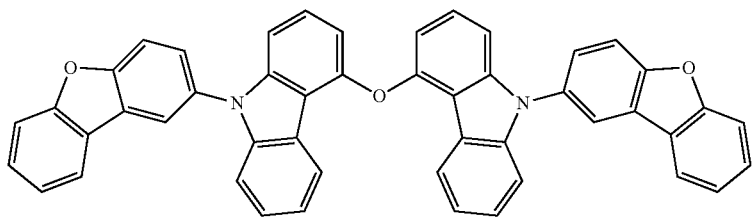

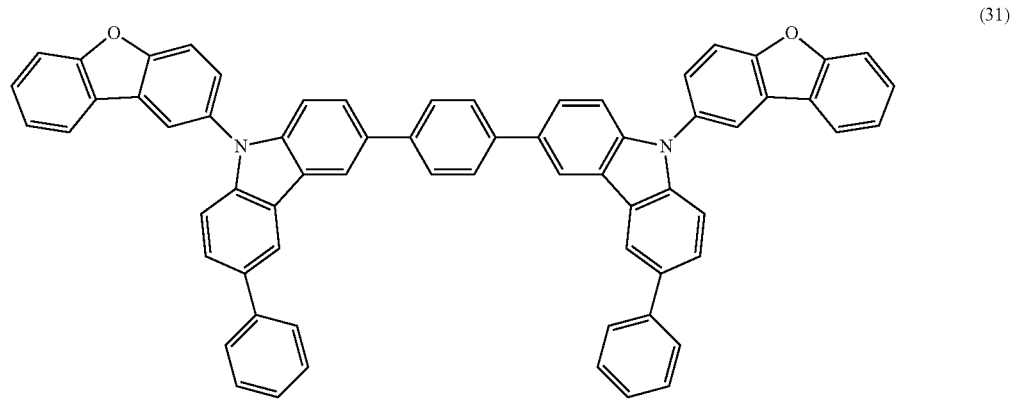
(31)
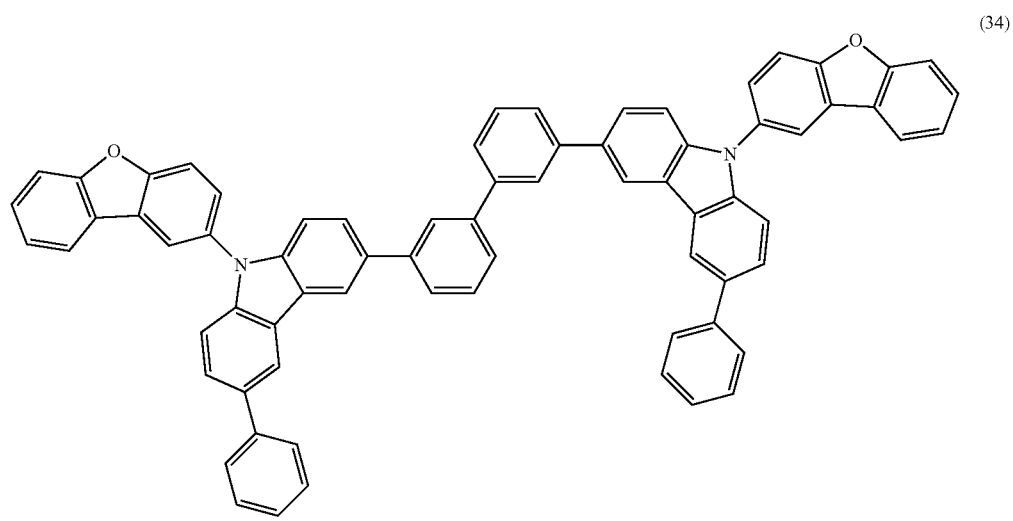
(34)
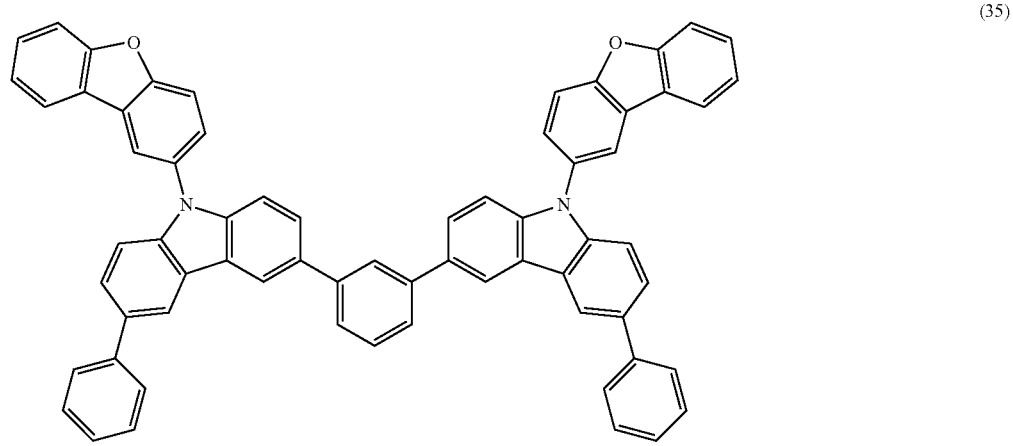
(35)

-continued
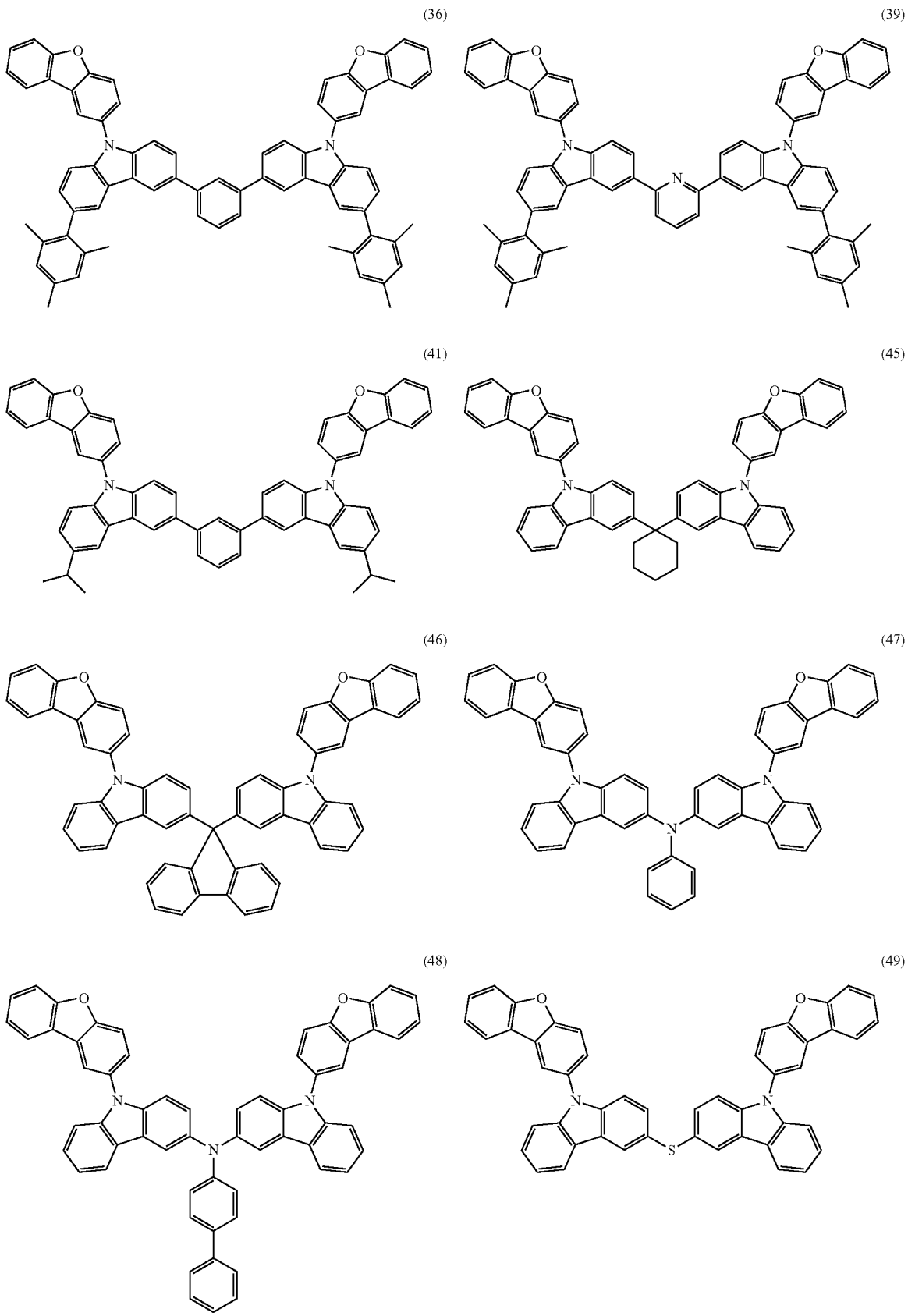

-continued
(50)
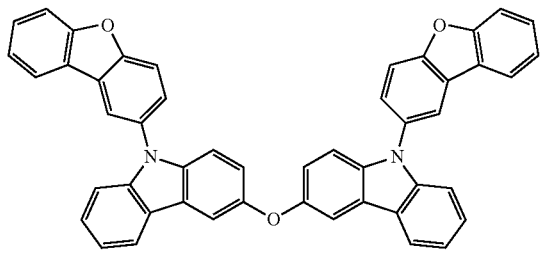
(51)
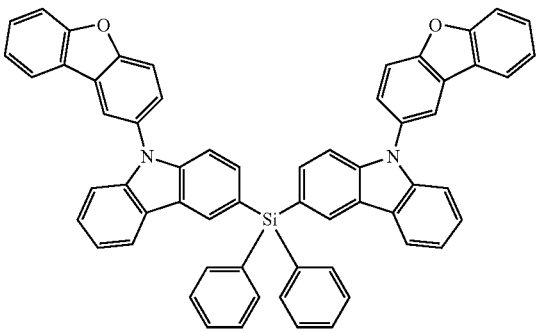
(52)
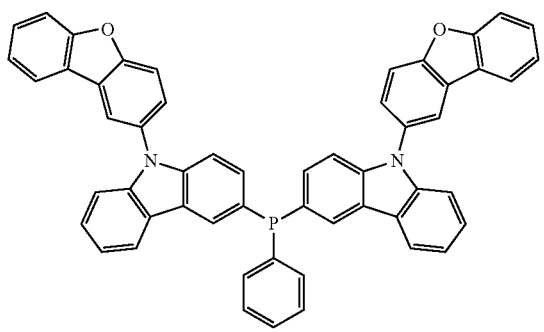
(53)
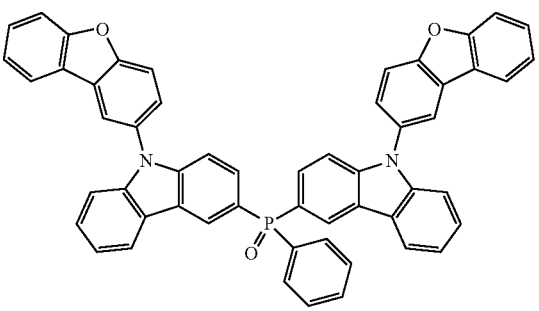
(54)
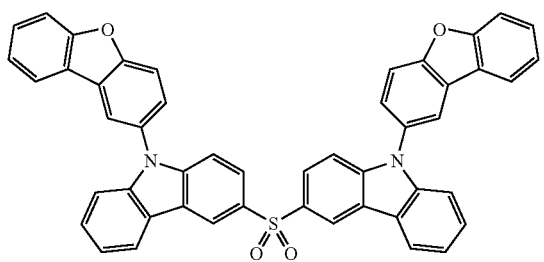
(55)
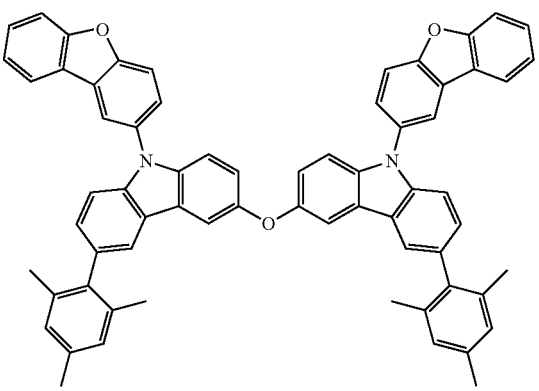
(56)
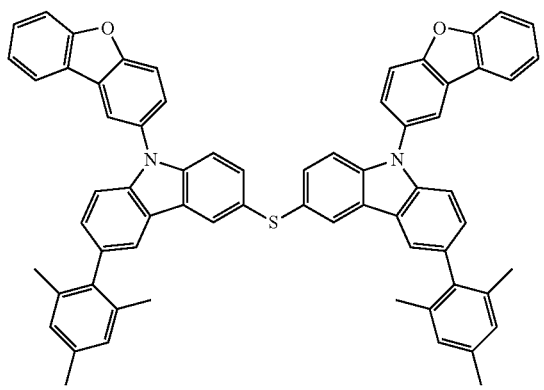
(57)
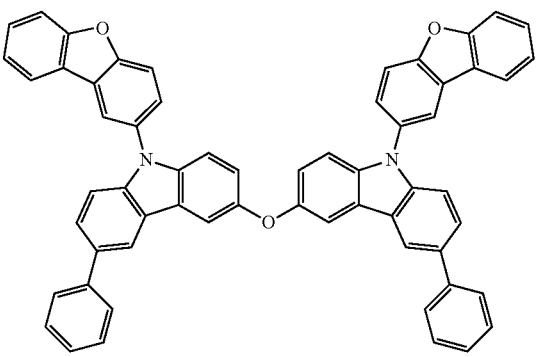

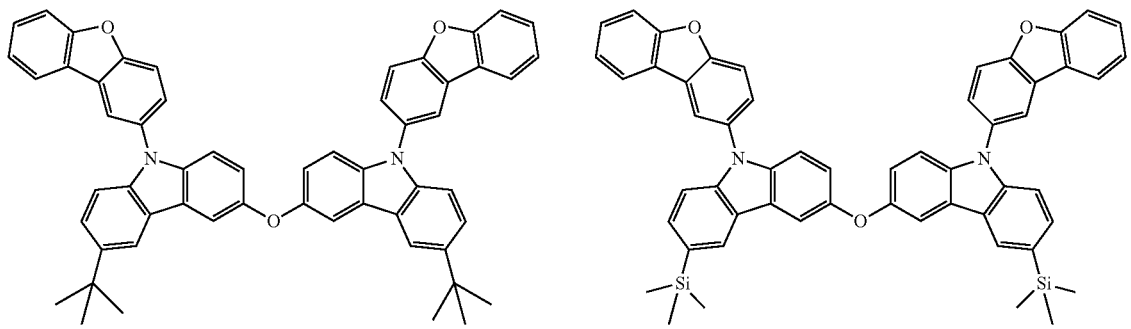
(59)
(60)
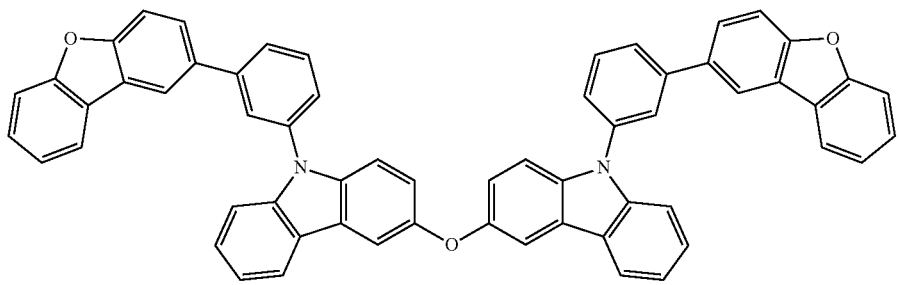
(61)
(62)
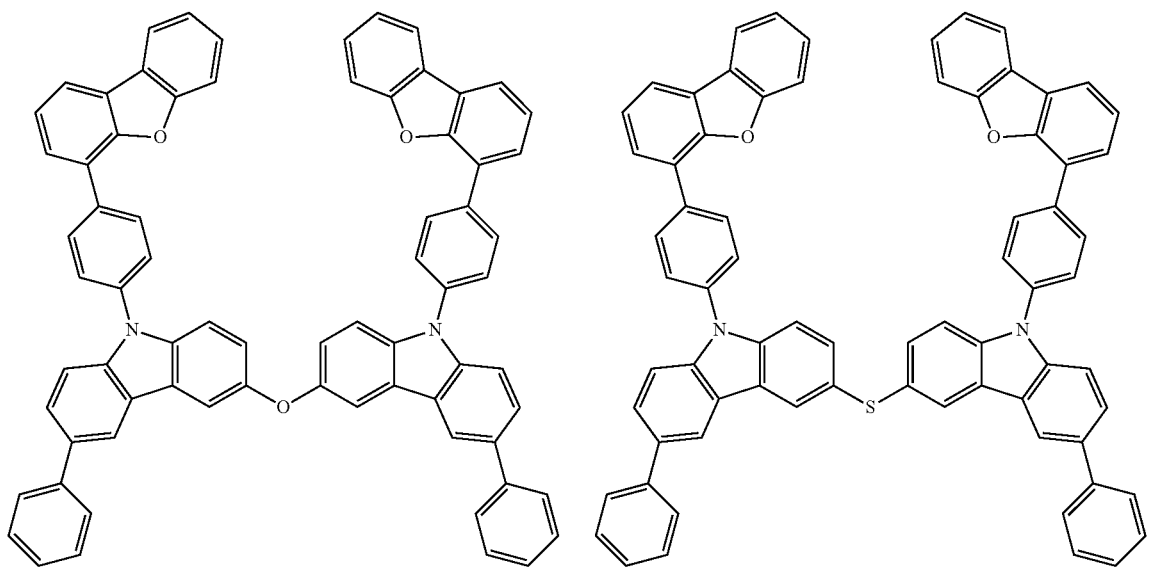
(66)
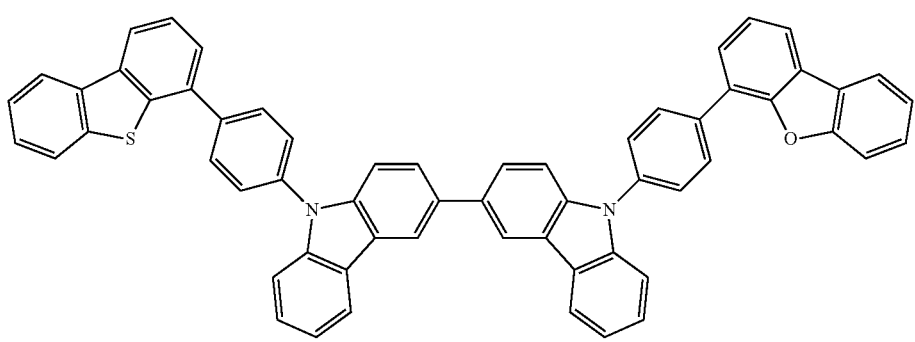

-continued
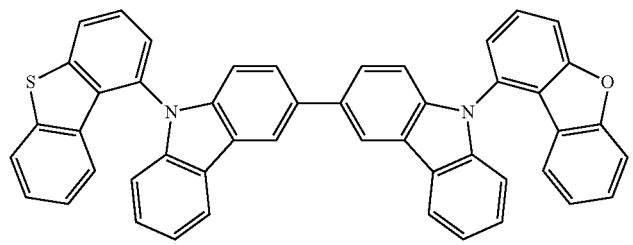
(68)
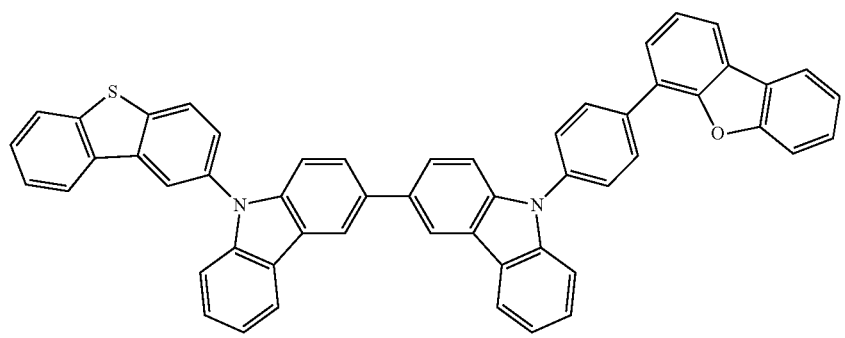
(69)
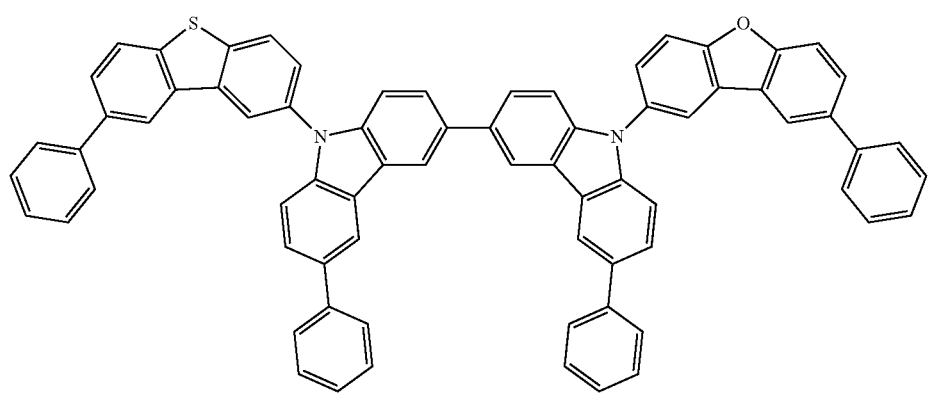
(70)
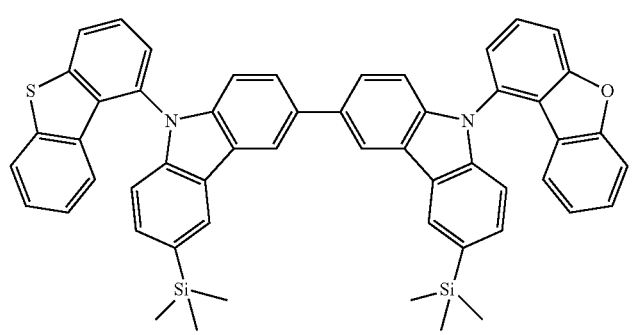
(71)

-continued
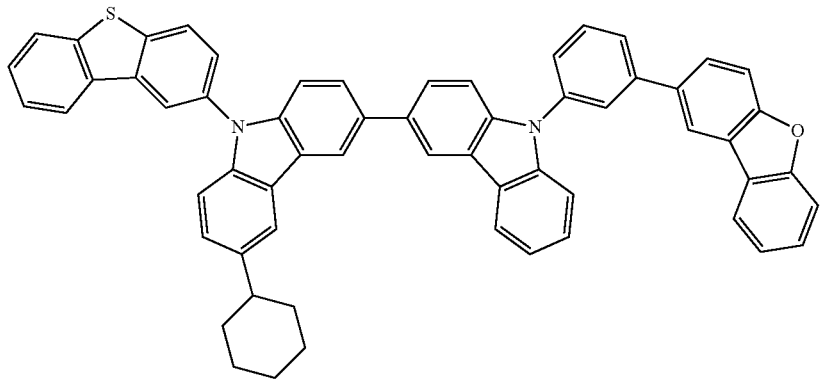
(72)
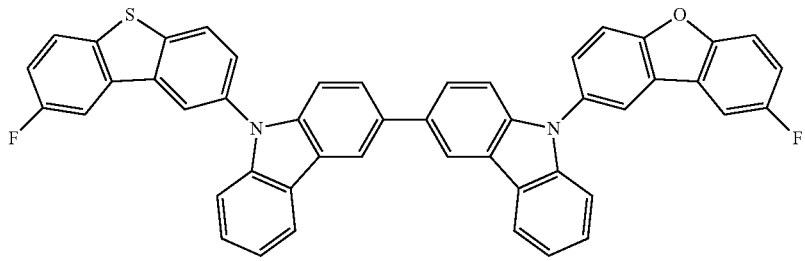
(73)
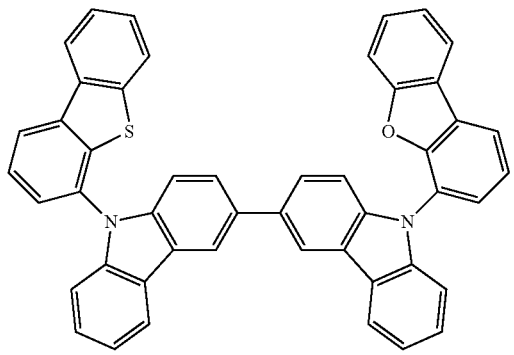
(74)
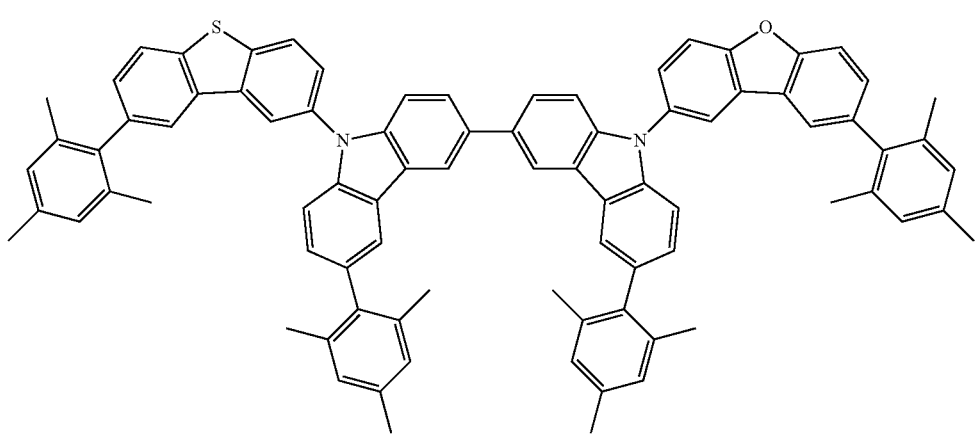
(75)

-continued
(77)
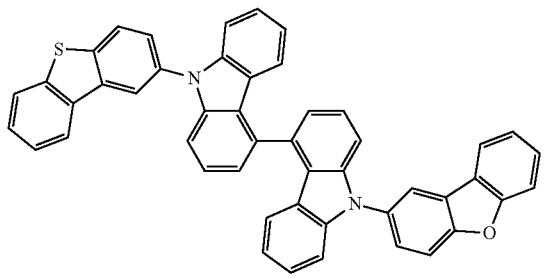
(78)
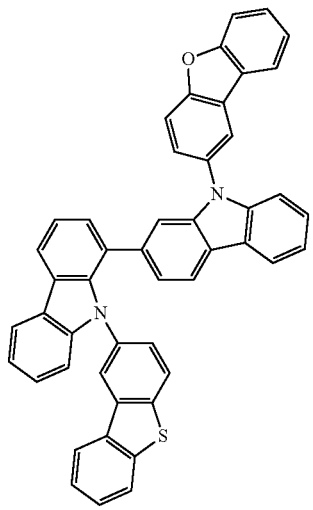
(79)
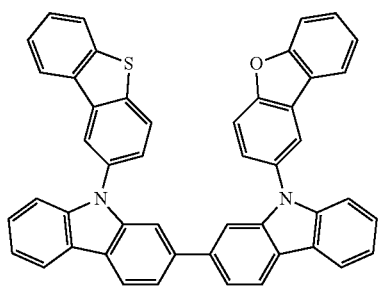
(81)
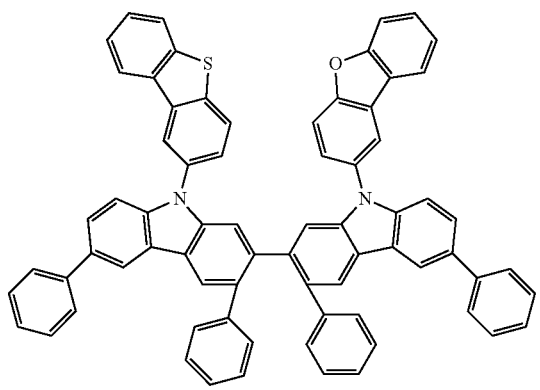
(82)
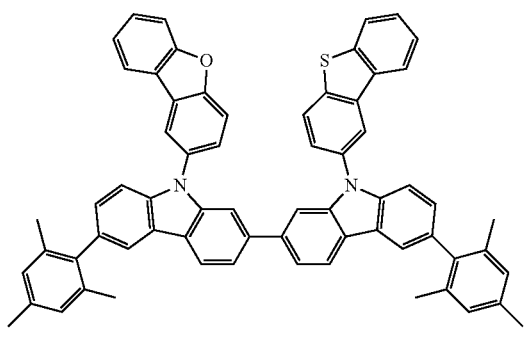
(83)
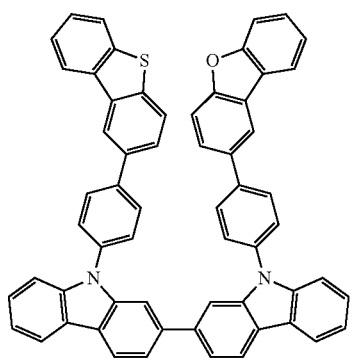

-continued
(84)
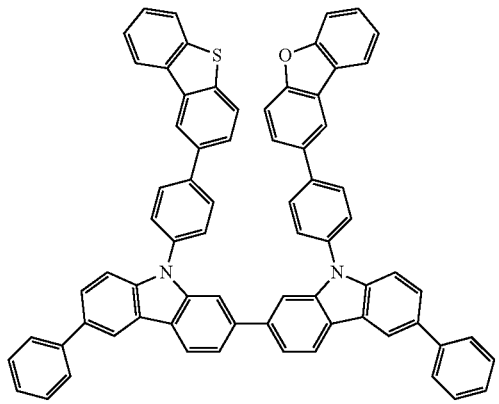
(85)
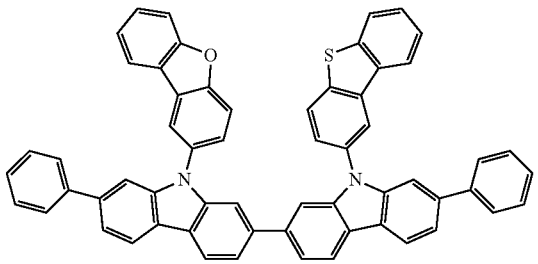
(88)
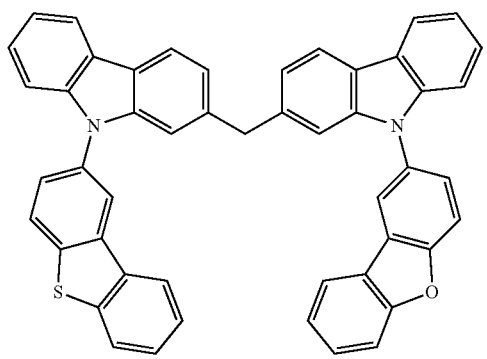
(89)
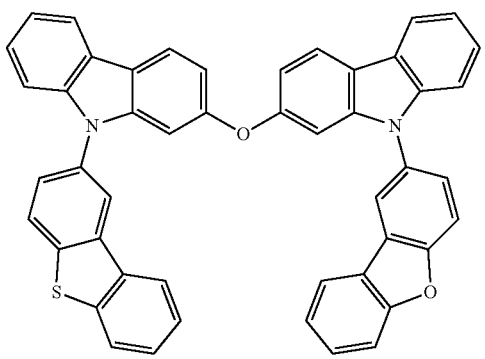
(90)
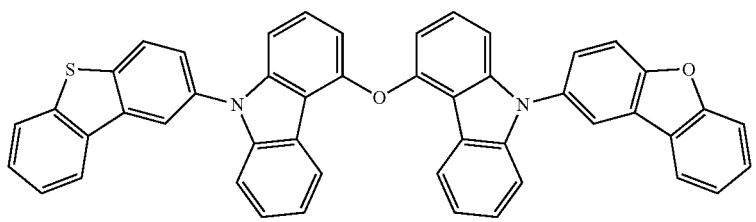
(97)
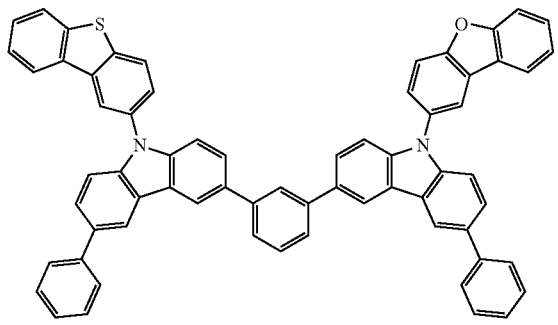
(101)
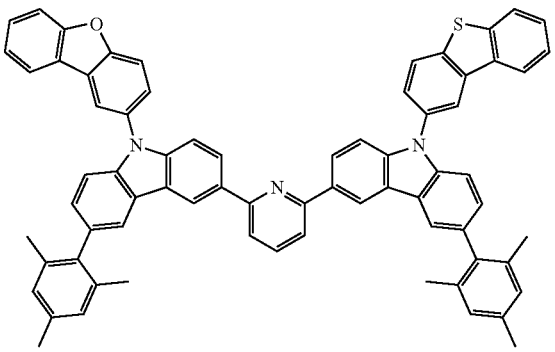

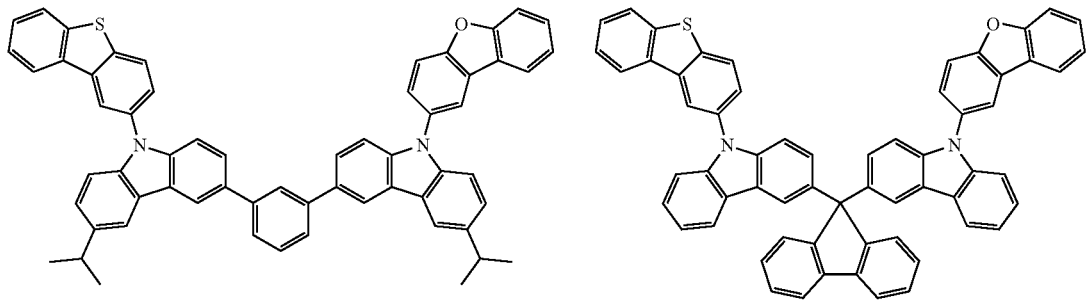
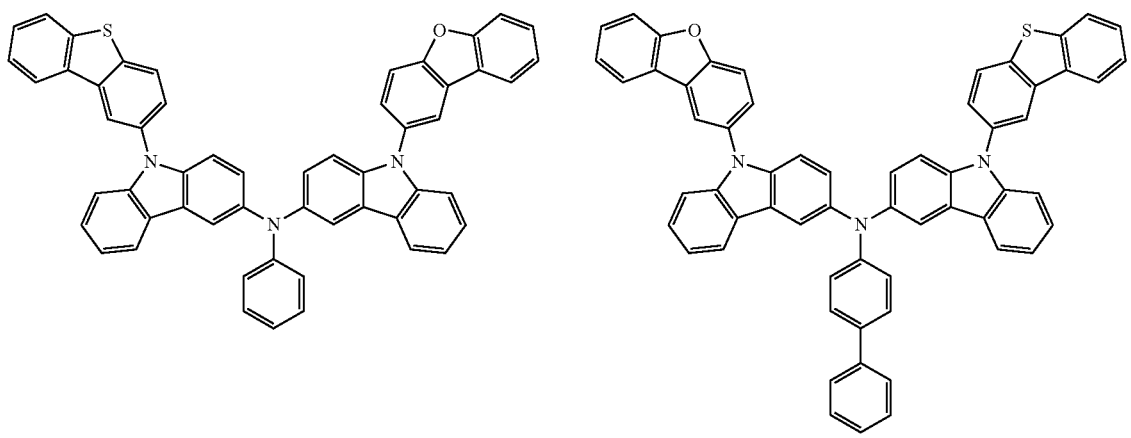
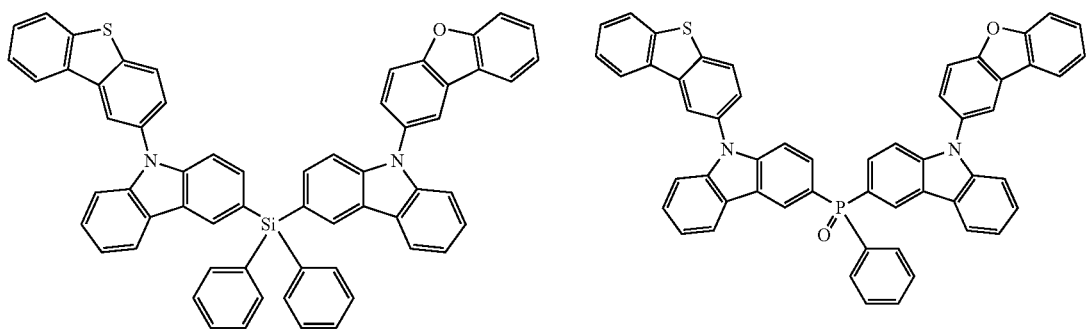
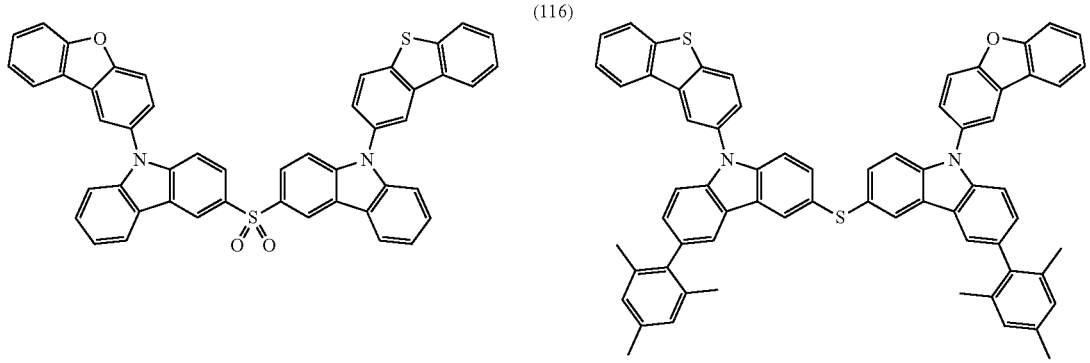

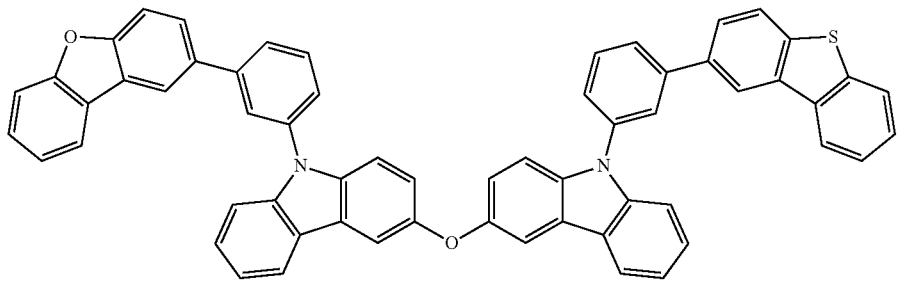
(122)
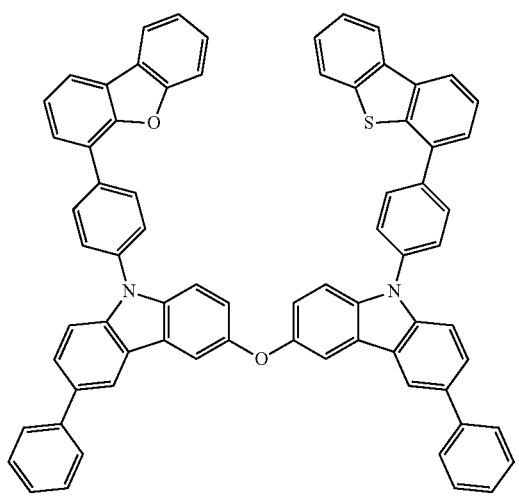
(123)
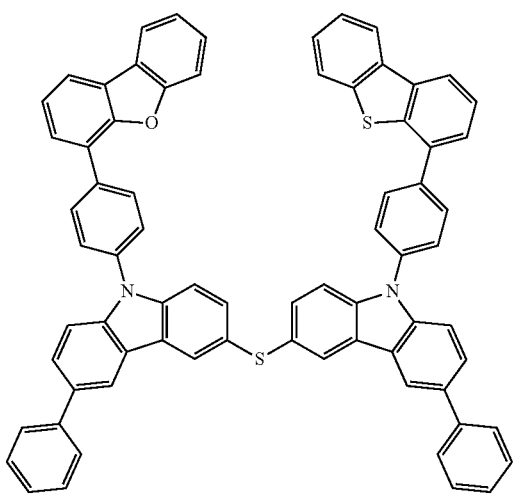
(124)
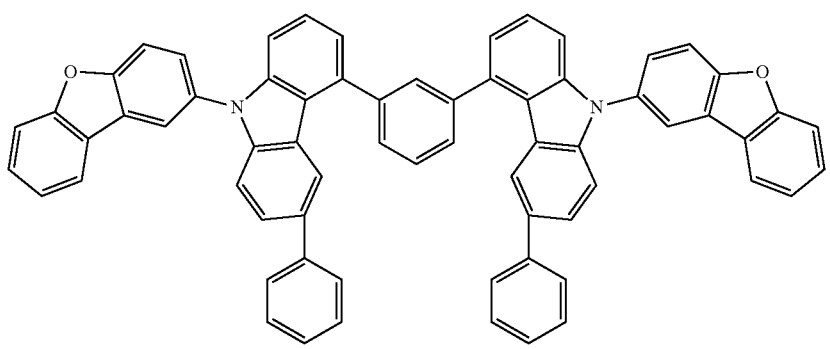
(125)

(126)
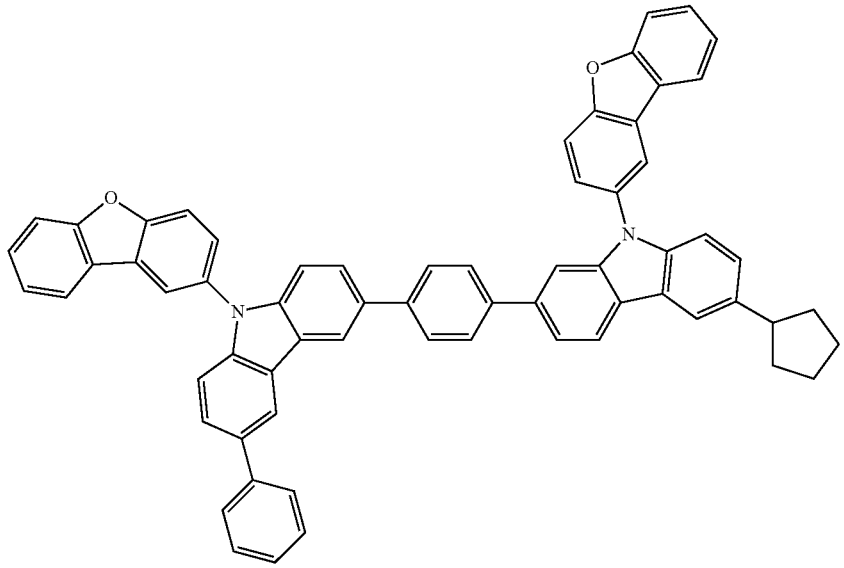
(127)
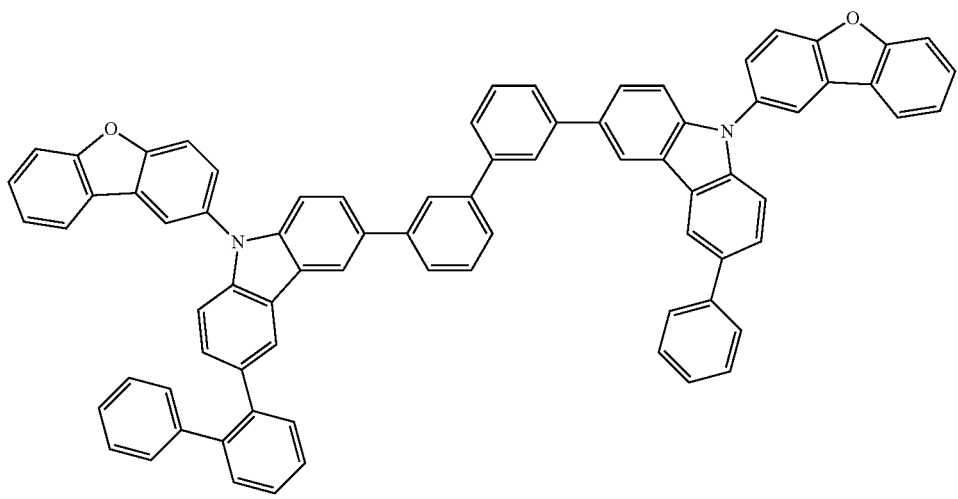
(128)
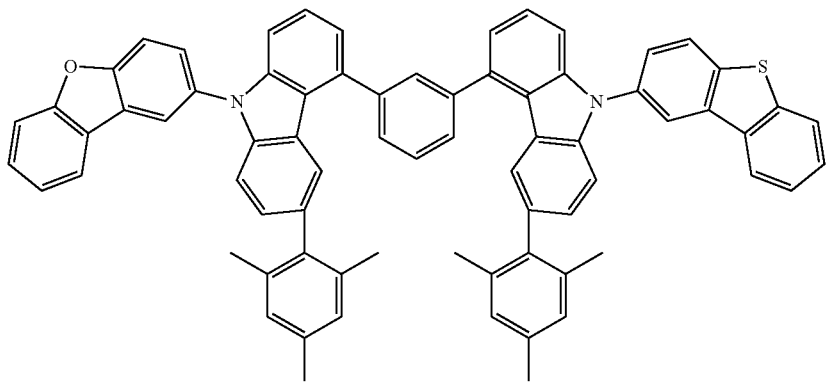

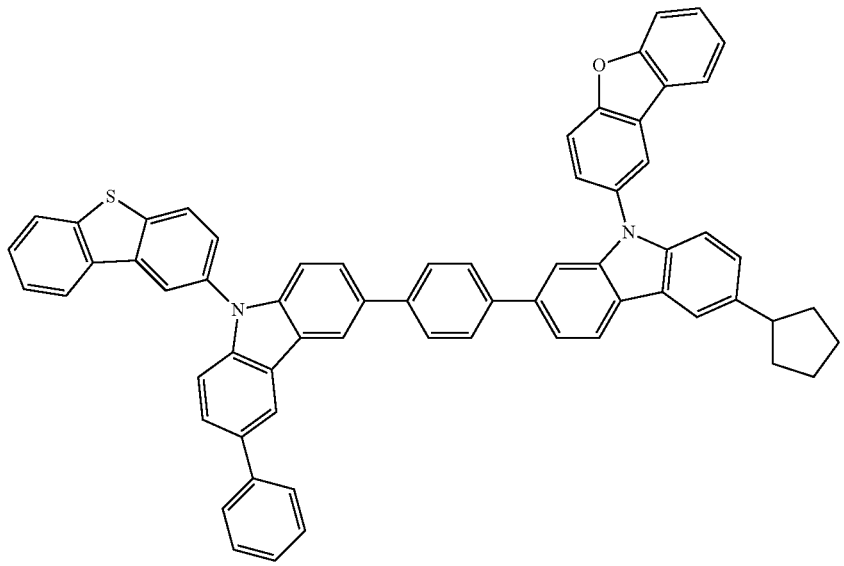

(129)

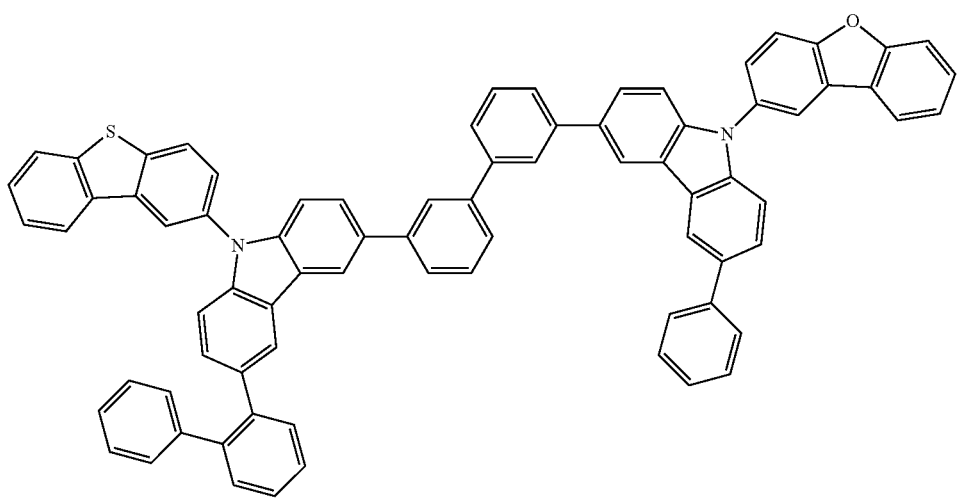

(130)

Among the compounds shown above, the compounds (1), (2), (3), (4), (5), (7), (8), (13), (35), (36), (48), (49), (54), (55), (56), (59) and (60) are preferred, and the compounds (1), (2), (3), (8), (13), (54), (55), (56) and (60) are more preferred.

The material for an organic EL device according to the present invention is preferably a host material contained in a light emitting layer of the organic EL device.

Next, the organic EL device of the present invention shall be explained.

The organic EL device of the present invention has one or more organic thin film layers including a light emitting layer between a cathode and an anode, and at least one layer of the above organic thin film layers contains the material for an organic EL device according to the present invention.

The structure of the organic EL device of a multilayer type includes, for example, structures in which layers are laminated in a multilayer constitution, such as anode/hole transporting layer (hole injecting layer)/light emitting layer/cathode, anode/light emitting layer/electron transporting layer (electron injecting layer)/cathode, anode/hole transporting layer (hole injecting layer)/light emitting layer/electron transporting layer (electron injecting layer)/cathode, anode/hole transporting layer (hole injecting layer)/light emitting layer/hole blocking layer/electron transporting layer (electron injecting layer)/cathode and the like. In the present invention, "the hole transporting/hole injecting layer" is included in the mode of the hole transporting layer.

In the organic EL device of the present invention, the light emitting layer described above contains preferably the material for an organic EL device represented by Formula (1) as a host material, and it contains more preferably a phosphorescence luminescence material. Also, when the organic EL device of the present invention has a hole transporting layer (hole injecting layer), the material for an organic EL device according to the present invention can preferably be contained as well in the above hole transporting layer (hole injecting layer).

The phosphorescence luminescence material is preferably a compound containing metal selected from iridium (Ir), osmium (Os) and platinum (Pt) in terms of having a high phosphorescence quantum efficiency and making it possible to enhance more an external quantum efficiency of the light emitting device, and it is more preferably a metal complex such as an iridium complex, an osmium complex and a platinum complex. Among them, the iridium complex and the platinum complex are more preferred. The metal complexes described above are preferably ortho-metallization metal complexes in which a central metal atom is subjected to ortho-metal bonding with a carbon atom contained in a ligand, and ortho-metallation iridium complexes are more preferred. The further preferred modes of the ortho-metallization metal complexes include iridium complexes shown below.

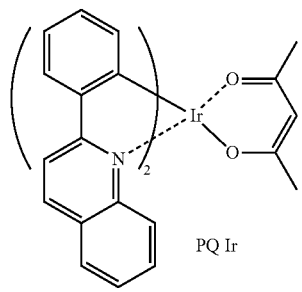

PQ Ir

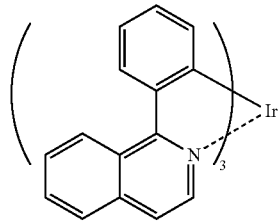

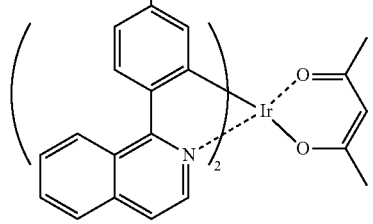

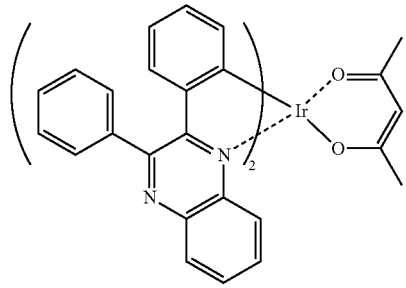

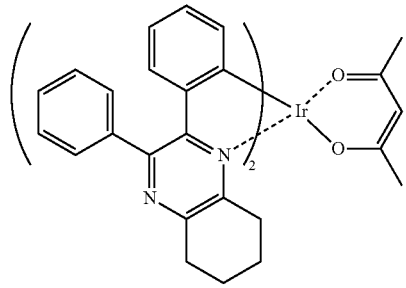

-continued

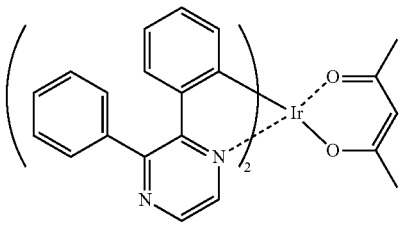

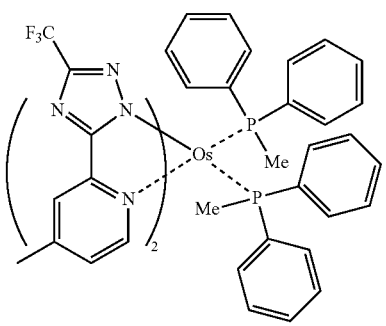

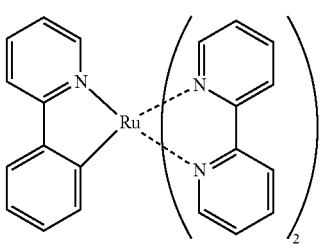

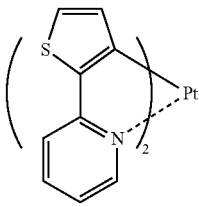

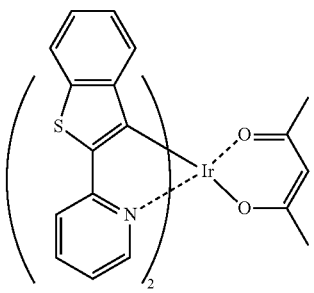

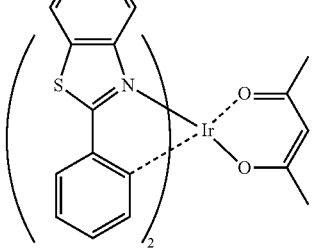

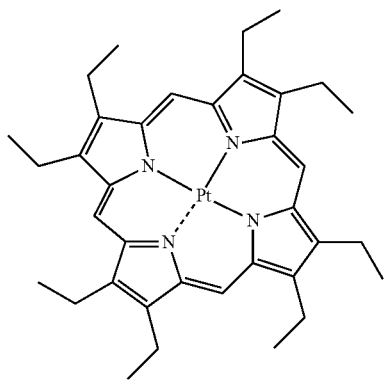
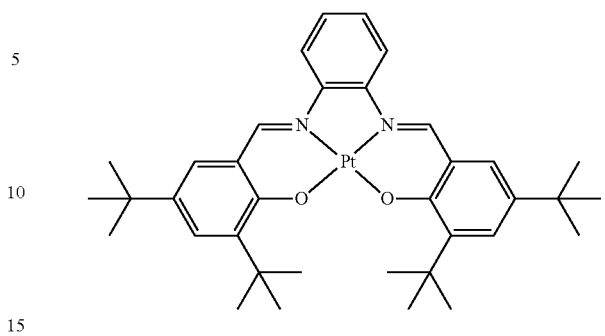
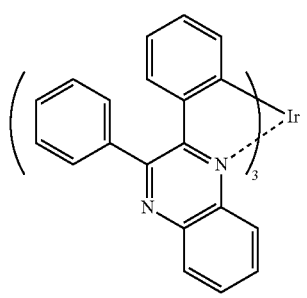
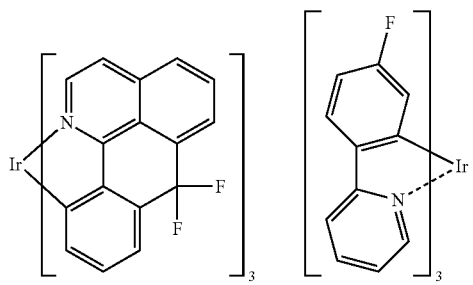
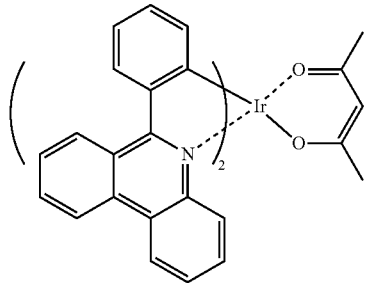
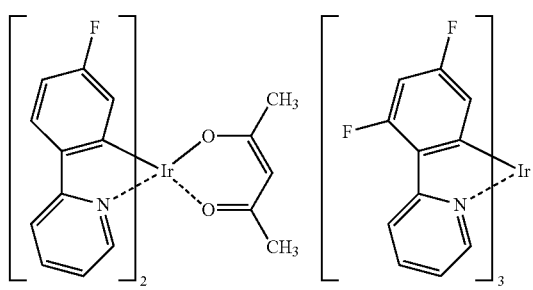
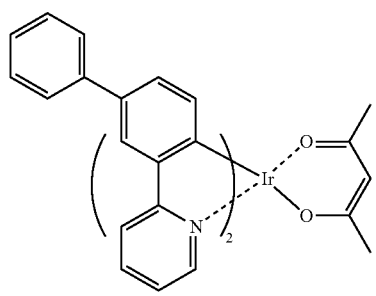
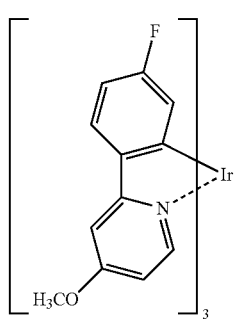
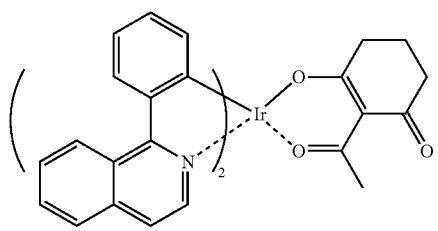
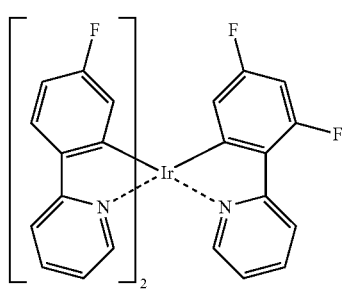

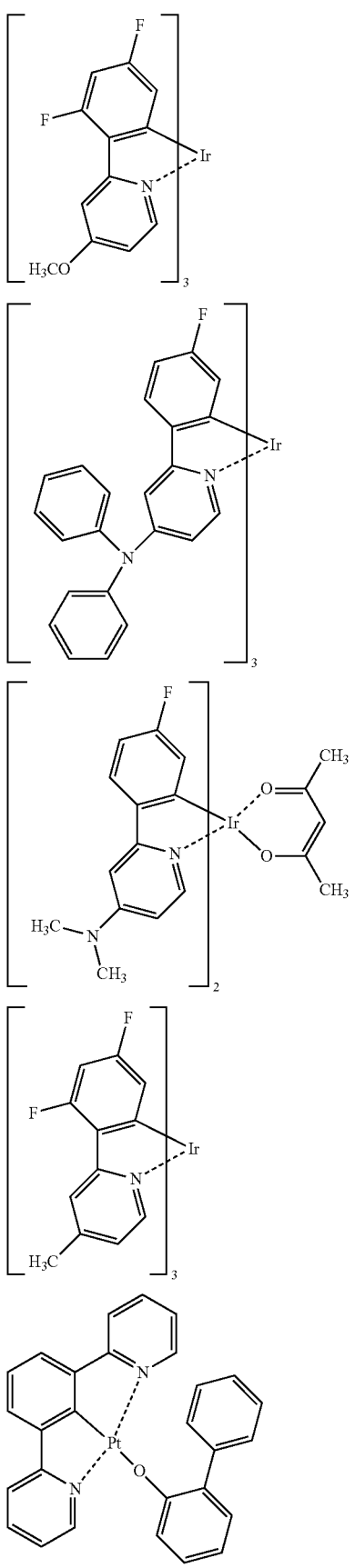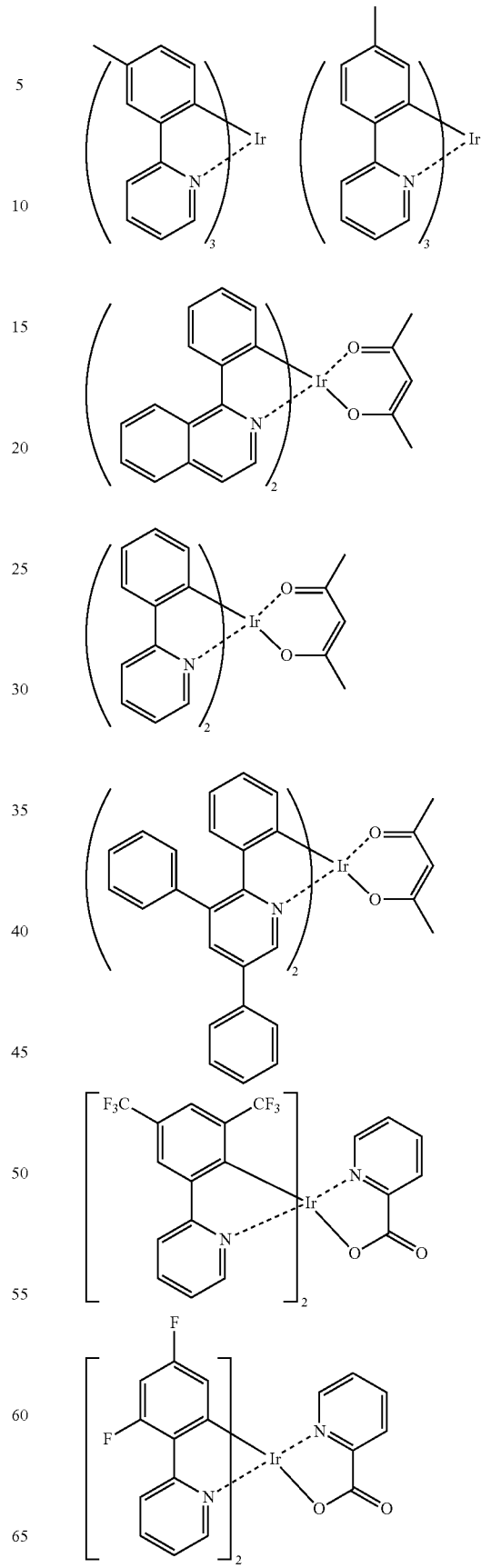

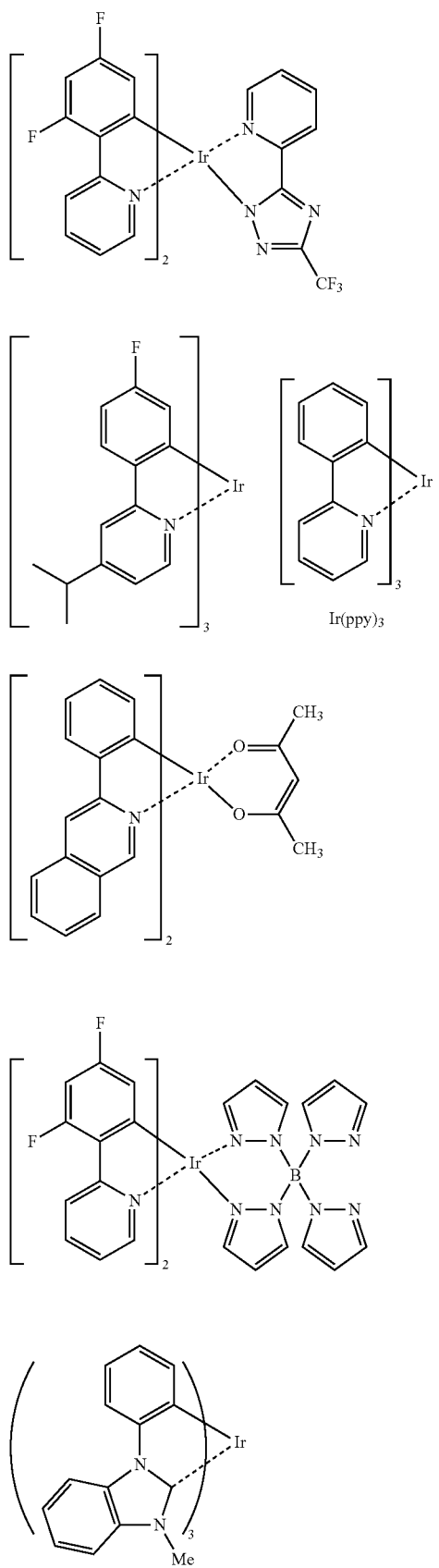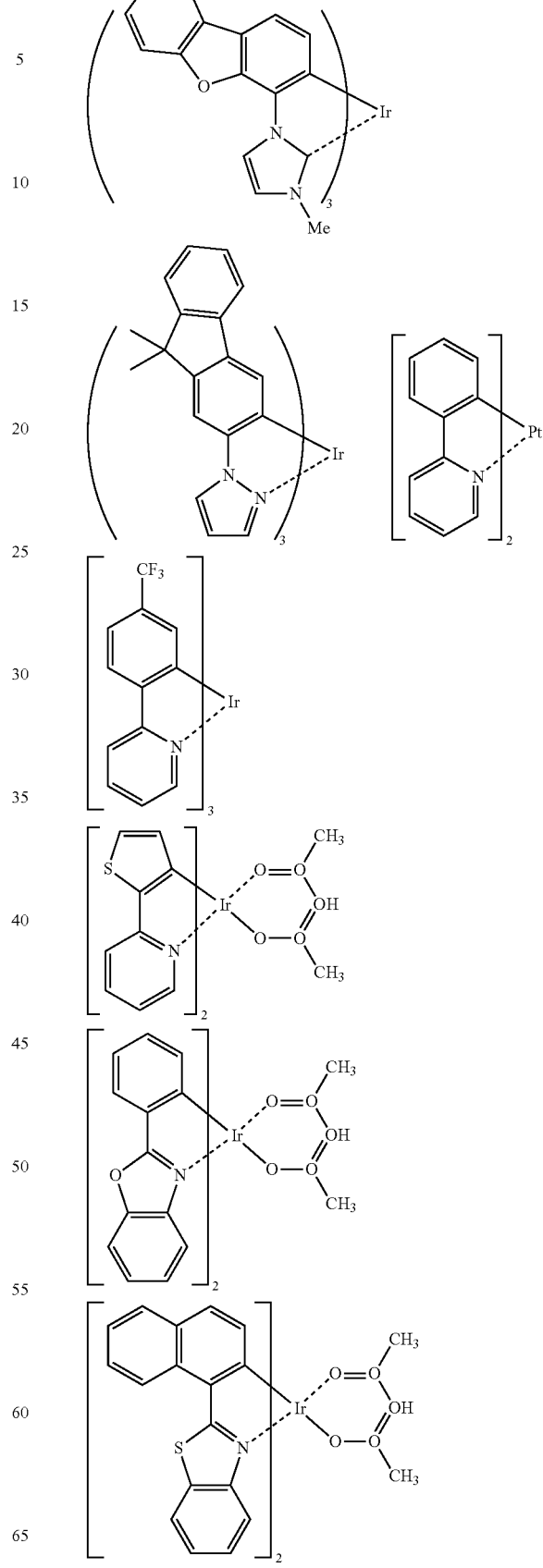

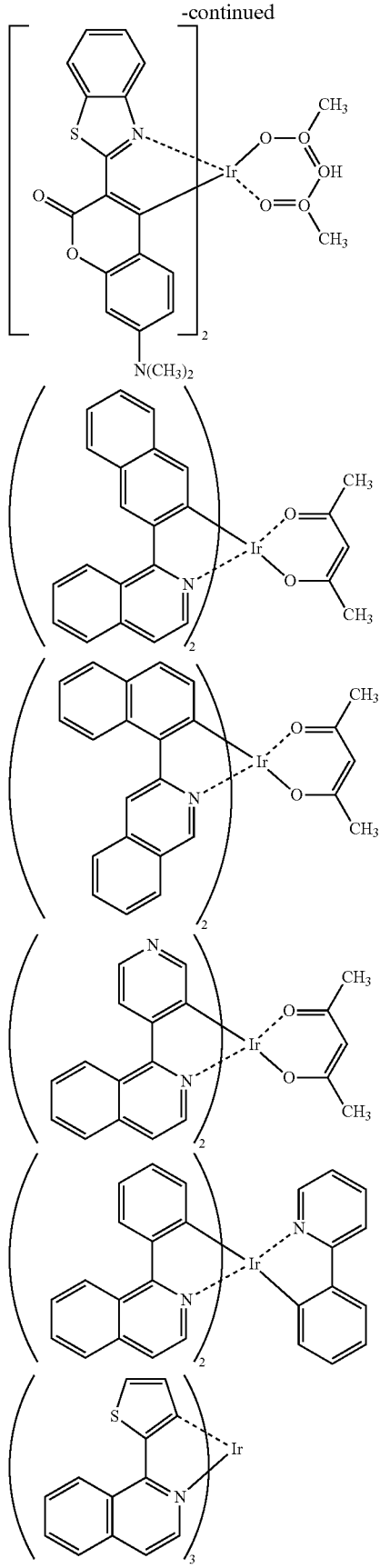

Further, in the organic EL device of the present invention, the light emitting layer described above contains preferably the host material containing the material for an organic EL device according to the present invention and the phosphorescence luminescence material, and it contains preferably a blue light emitting metal complex having a maximum value of 500 nm or less in an emission wavelength as the phosphorescence luminescence material.

The organic EL device of the present invention has a hole transporting layer (hole injecting layer), and the above hole transporting layer (hole injecting layer) preferably contains as well the material for an organic EL device according to the present invention.

The organic EL device of the present invention contains preferably a reducing dopant in an interfacial region between a cathode and an organic thin film layer. The reducing dopant includes at least one selected from alkali metals, alkali metal complexes, alkali metal compounds, alkaline earth metals, alkaline earth metal complexes, alkaline earth metal compounds, rare earth metals, rare earth metal complexes, rare earth metal compounds and the like.

The alkali metal includes Na (work function: 2.36 eV), K (work function: 2.28 eV), Rb (work function: 2.16 eV), Cs (work function: 1.95 eV) and the like, and the metals having a work function of 2.9 eV or less are particularly preferred. Among them, K, Rb and Cs are preferred, and Rb or Cs is more preferred. Cs is most preferred.

The alkaline earth metals include Ca (work function: 2.9 eV), Sr (work function: 2.0 to 2.5 eV), Ba (work function: 2.52 eV) and the like, and the metals having a work function of 2.9 eV or less are particularly preferred.

The rare earth metals include Sc, Y, Ce, Tb, Yb and the like, and the metals having a work function of 2.9 eV or less are particularly preferred.

Among the above metals, the preferred metals have a particularly high reducing ability, and addition thereof to an electron injecting zone in a relatively small amount makes it possible to enhance an emission luminance and extend a lifetime in the organic EL device.

The alkali metal compounds include alkali oxides such as $Li_2O$, $Cs_2O$, $K_2O$ and the like, and alkali halides such as LiF, NaF, CsF, KF and the like. LiF, $Li_2O$ and NaF are preferred.

The alkaline earth metal compounds include BaO, SrO, CaO and $Ba_xSr_{1-x}O$ (0<x<1), $Ba_xCa_{1-x}O$ (0<x<1) and the like which are obtained by mixing the above compounds, and BaO, SrO and CaO are preferred.

The rare earth metal compounds include $YbF_3$, $ScF_3$, $Y_2O_3$, $Ce_2O_3$, $GdF_3$, $TbF_3$ and the like, and $YbF_3$, $ScF_3$ and $TbF_3$ are preferred.

The alkali metal complexes, the alkaline earth metal complexes and the rare earth metal complexes shall not specifically be restricted as long as they contain at least one metal ion of alkali metal ions, alkaline earth metal ions and rare earth metal ions. Preferred for the ligands are quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfurborane, bipyridyl, phenanthroline, phthalocyanine, porphyrin, cyclopentadiene, β-diketones, azomethines and derivatives thereof, but they shall not be restricted to the above compounds.

In respect to an addition mode of the reducing dopant, it is formed preferably in a layer shape or an island shape in an interfacial region. A forming method thereof is preferably a method in which while depositing the reducing dopant by a resistance heating deposition method, organic substances used as a light emitting material or an electron injecting material for forming an interfacial region are deposited at the same time to disperse the reducing dopant in the organic substances. The dispersion concentration is the organic substances: the reducing dopant=100:1 to 1:100, preferably 5:1 to 1:5 in terms of a molar ratio. When the reducing dopant is formed into a layer shape, a light emitting material or an electron injecting material used for forming an organic layer in an interface are formed into a layer shape, and then the reducing dopant is deposited separately by a resistance heating deposition method. The layer is formed preferably in a layer thickness of 0.1 to 15 nm. When the reducing dopant is formed into an island shape, the light emitting material or the electron injecting material used for forming an organic layer in an interface are formed into an island shape, and then the reducing dopant is deposited separately by the resistance heating deposition method. The layer is formed preferably in an island thickness of 0.05 to 1 nm.

The organic EL device of the present invention has an electron injecting layer between a light emitting layer and a cathode, and the above electron injecting layer contains preferably a nitrogen-containing heterocyclic derivative as a principal component. An aromatic heterocyclic compound having at least one hetero atom in a molecule is preferably used as an electron transporting material used for the electron injecting layer, and a nitrogen-containing heterocyclic derivative is particularly preferred.

The above nitrogen-containing heterocyclic derivative is preferably, for example, a nitrogen-containing heterocyclic metal chelate complex represented by Formula (A).

The above nitrogen-containing heterocyclic derivative is preferably, for example, a nitrogen-containing heterocyclic metal chelate complex represented by Formula (A):

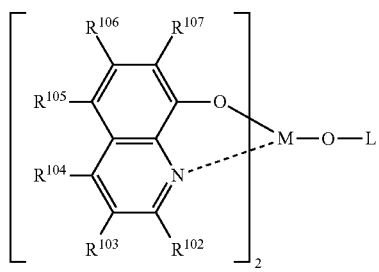

(A)

$R^{102}$ to $R^{107}$ each are independently a hydrogen atom, a halogen atom, an amino group, a hydrocarbon group having 1 to 40 carbon atoms, an alkoxy group, an aryloxy group, an alkoxycarbonyl group or a heterocyclic group, and they may be substituted.

The examples of the halogen atom include a fluorine atom, a chlorine atom, a bromine atom and an iodine atom. Also, The examples of the amino group which may be substituted include the same groups as in the alkylamino group and the arylamino group each described above. Further, it may be an aralkylamino group.

The hydrocarbon group having 1 to 40 carbon atoms include a substituted or non-substituted alkyl group, an alkenyl group, a cycloalkyl group, an aryl group, an aralkyl group and the like. The examples of the alkyl group, the cycloalkyl group, the alkoxy group, the aryl group, the heterocyclic group and the aryloxy group include the same groups as described above. The alkenyl group includes groups corresponding to the alkyl groups described above. The aralkyl group include the alkyl groups described above which are substituted with the aryl groups described above. The alkoxycarbonyl group is represented by —COOY', and the examples of Y' include the same groups as the alkyl groups described above.

M is aluminum (Al), gallium (Ga) or indium (In), and it is preferably In.

L in Formula (A) is a group represented by Formula (A') or (A") shown below:

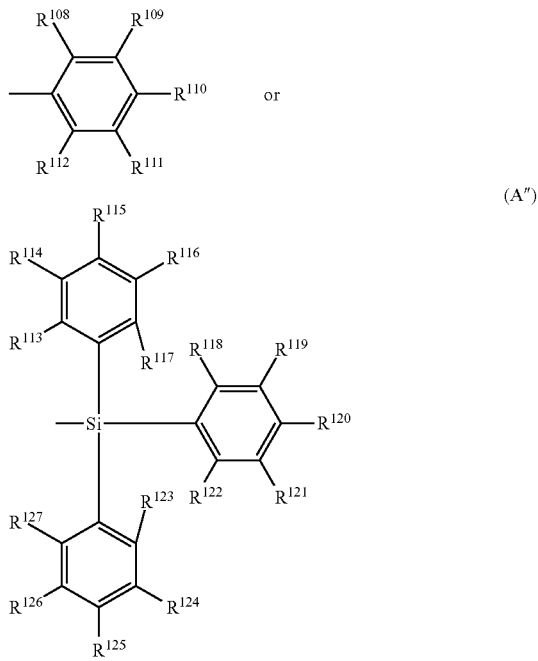

(wherein $R^{108}$ to $R^{112}$ each are independently a hydrogen atom or a substituted or non-substituted hydrocarbon group having 1 to 40 carbon atoms, and the groups which are adjacent to each other may form a cyclic structure; further, $R^{113}$ to $R^{127}$ each are independently a hydrogen atom or a substituted or non-substituted hydrocarbon group having 1 to 40 carbon atoms, and the groups which are adjacent to each other may form a cyclic structure).

The hydrocarbon group having 1 to 40 carbon atoms represented by $R^{108}$ to $R^{112}$ and $R^{113}$ to $R^{127}$ in Formula (A') and Formula (A") includes the same groups as the specific examples of $R^1$ to $R^8$.

Also, a divalent group in a case where the groups adjacent to each other in $R^{108}$ to $R^{112}$ and $R^{113}$ to $R^{127}$ form a cyclic structure includes tetramethylene, pentamethylene, hexamethylene, diphenylmethane-2,2'-diyl, diphenylethane-3,3'-diyl, diphenylpropane-4,4'-diyl and the like.

The specific examples of the nitrogen-containing heterocyclic metal chelate complex represented by Formula (A) shall be shown below, but they shall not be restricted to these compounds shown as the examples.

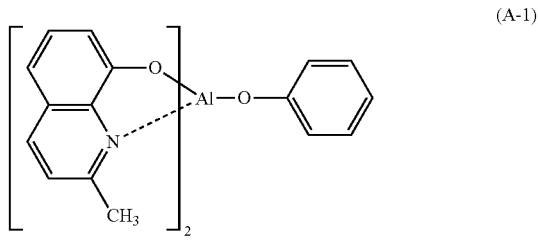

(A-1)

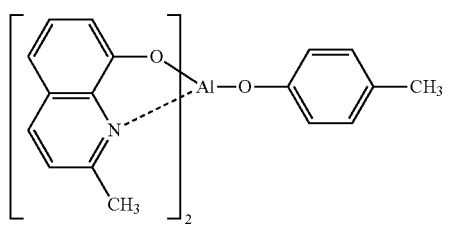
(A-2)
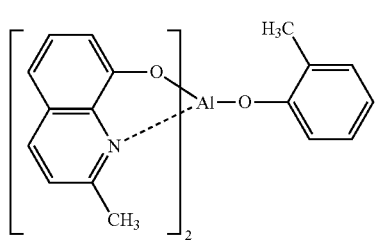
(A-3)
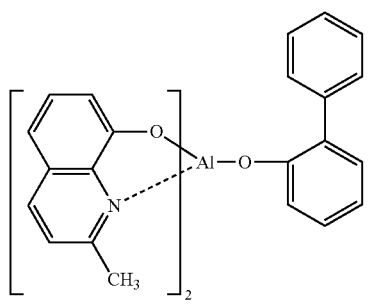
(A-4)
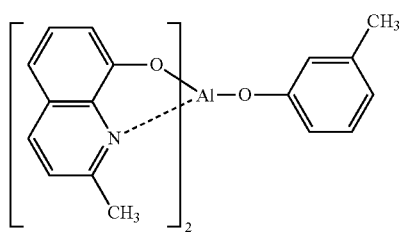
(A-5)
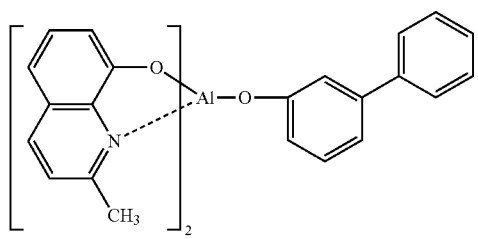
(A-6)
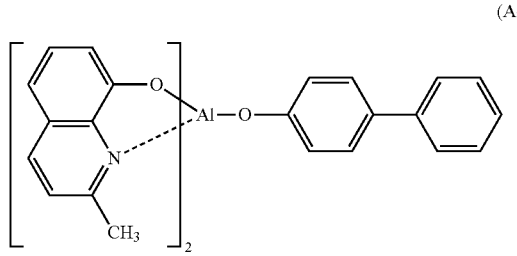
(A-7)
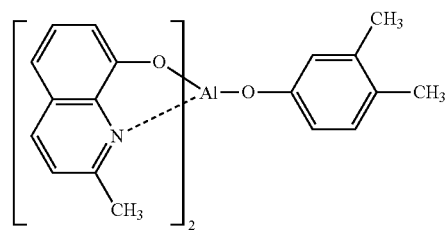
(A-8)
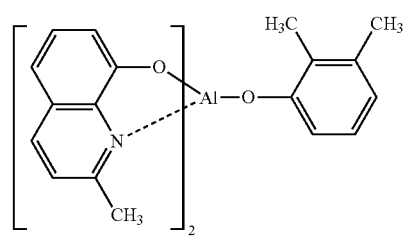
(A-9)
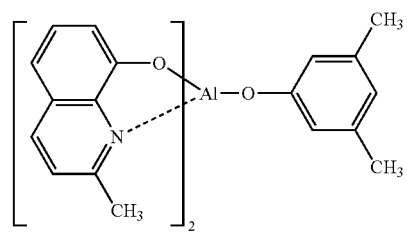
(A-10)
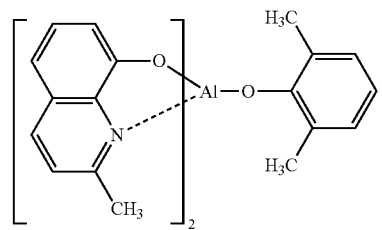
(A-11)
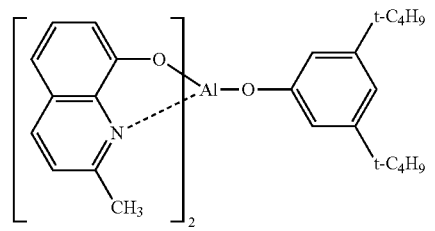
(A-12)
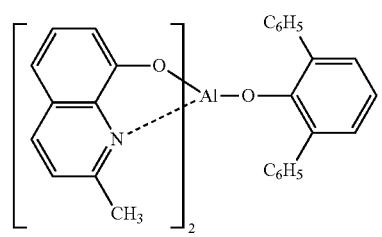
(A-13)
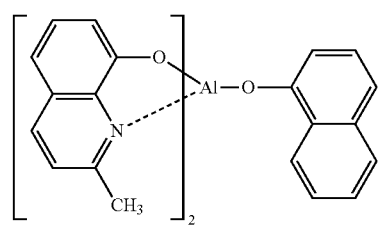
(A-14)

(A-15)
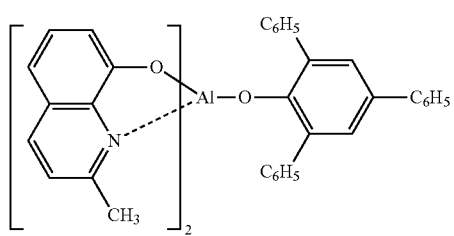
(A-16)
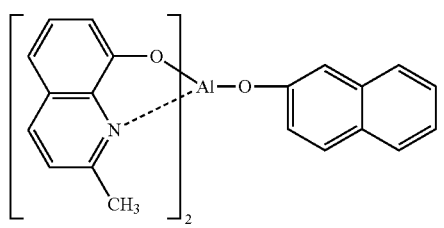
(A-17)
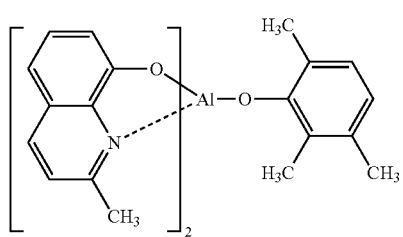
(A-18)
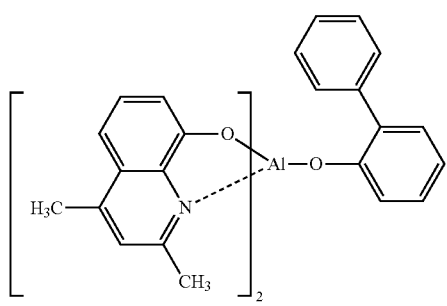
(A-19)
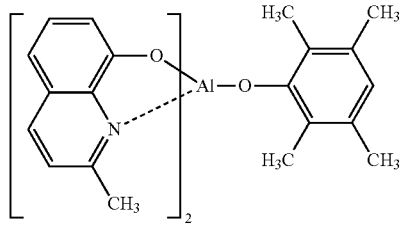
(A-20)
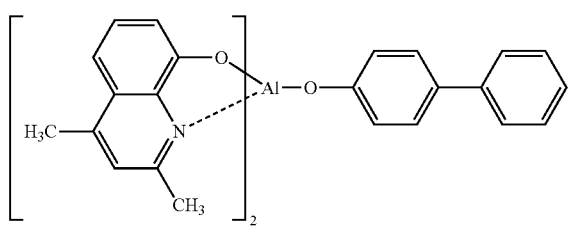
(A-21)
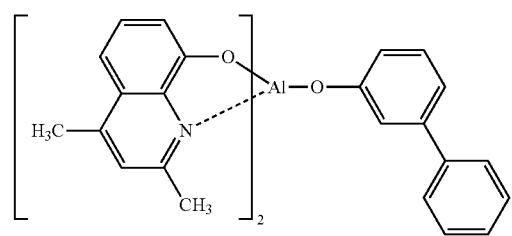
(A-22)
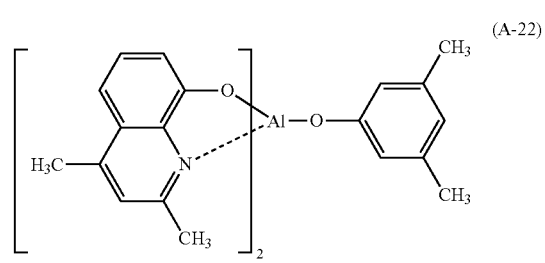
(A-23)
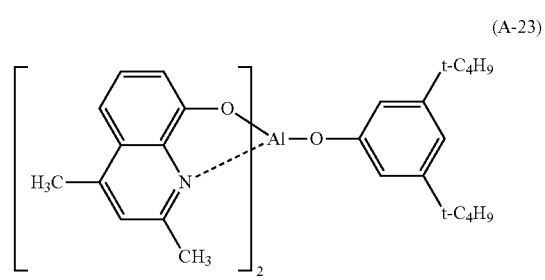
(A-24)
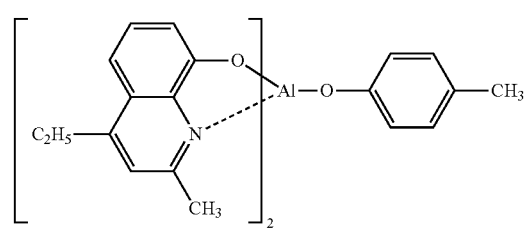
(A-25)
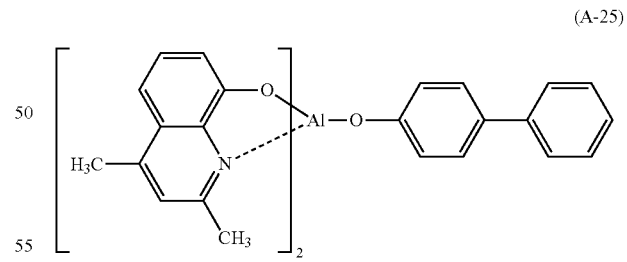
(A-26)
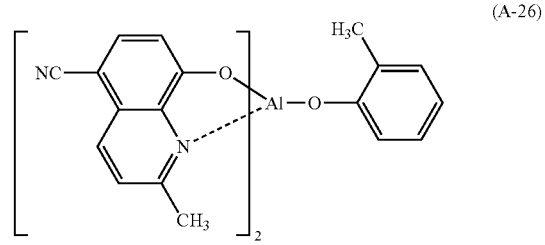

(A-27) 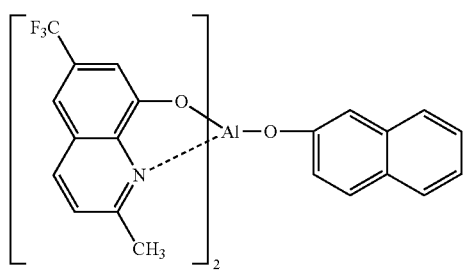

(A-32) 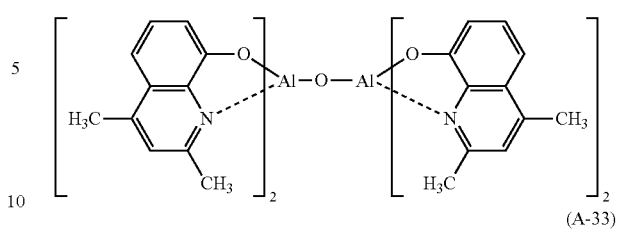

(A-28) 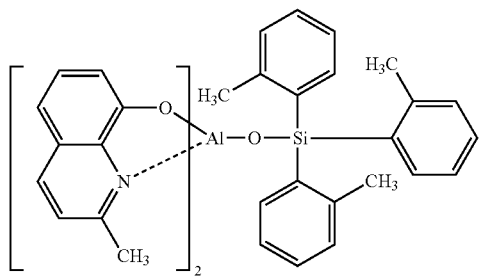

(A-29)

(A-30)

(A-31) 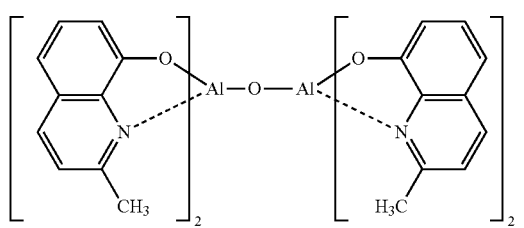

(A-33)

(A-34)

(A-35)

(A-36)

The nitrogen-containing heterocyclic derivative includes as well nitrogen-containing compounds which are nitrogen-containing heterocyclic derivatives comprising organic compounds having the following formulas and which are not metal complexes. It includes, for example, five-membered rings or six-membered rings having a skeleton represented by Formula (a) and derivatives having a structure represented by Formula (b):

(a)

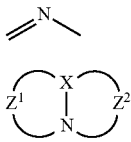

(b)

(in Formula (b), X represents a carbon atom or a nitrogen atom; $Z^1$ and $Z^2$ each are independently an atomic group which can form a nitrogen-containing heterocycle).

The nitrogen-containing heterocyclic derivative is preferably an organic compound having a nitrogen-containing aromatic polycycle comprising a five-membered ring or a six-membered ring. Further, in a case of the above nitrogen-containing aromatic polycycle having plural nitrogen atoms, it is a nitrogen-containing aromatic polycyclic organic compound having a skeleton obtained by combining the structures represented by Formulas (a) and (b) described above.

The nitrogen-containing group of the nitrogen-containing organic compound is selected from, for example, nitrogen-containing heterocyclic groups represented by the following formulas:

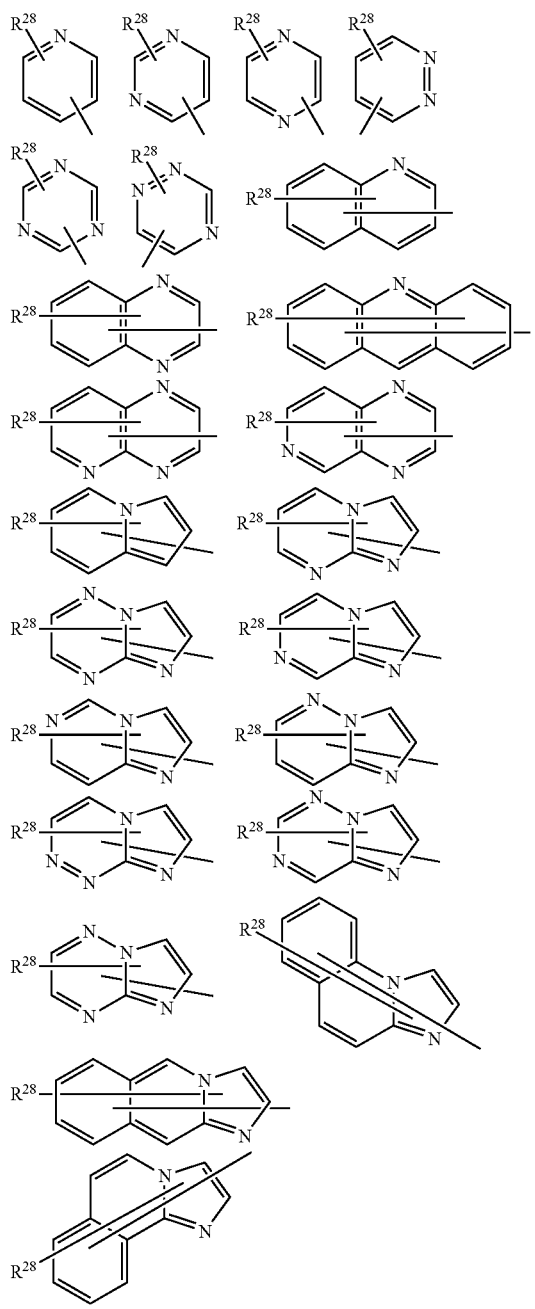

(in the respective formulas, n groups of $R^{28}$ are present, and they are an aryl group having 6 to 40 carbon atoms, a heteroaryl group having 3 to 40 carbon atoms, an alkyl group having 1 to 20 carbon atoms or an alkoxy group having 1 to 20 carbon atoms; n showing the number of $R^{28}$ is an integer of 0 to 5, and when n is an integer of 2 or more, plural $R^{28}$ may be the same as or different from each other).

Further, the preferred specific compounds include nitrogen-containing heterocyclic derivatives represented by the following Formula:

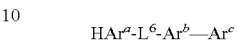

(wherein $HAr^a$ is a nitrogen-containing heterocycle having 3 to 40 carbon atoms which may have a substituent; $L^6$ is a single bond, an arylene group having 6 to 40 carbon atoms which may have a substituent or a heteroarylene group having 3 to 40 carbon atoms may have a substituent; $Ar^b$ is a divalent aromatic hydrocarbon group having 6 to 40 carbon atoms which may have a substituent; and $Ar^c$ is an aryl group having 6 to 40 carbon atoms which may have a substituent or a heteroaryl group having 3 to 40 carbon atoms which may have a substituent).

$HAr^a$ is selected from, for example, the following group:

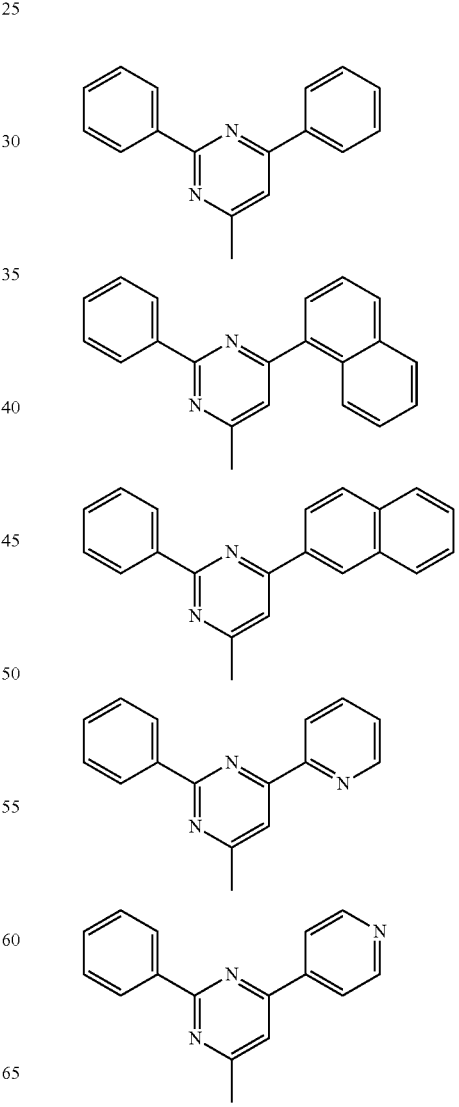

-continued
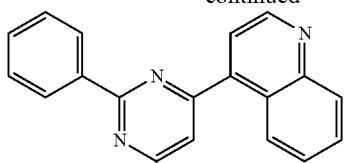
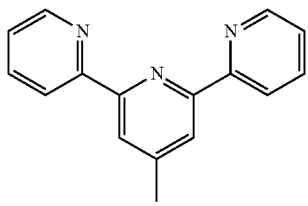
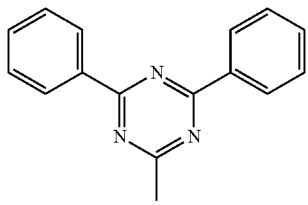 [SMILES: Cc1cc(-c2ccccc2)nc(-c2ccccn2)c1]
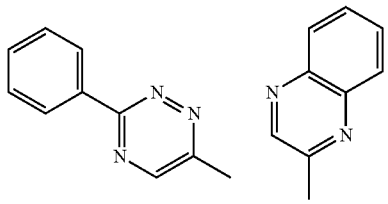
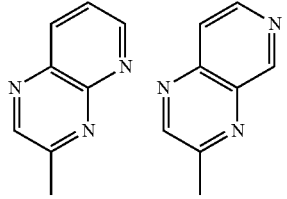
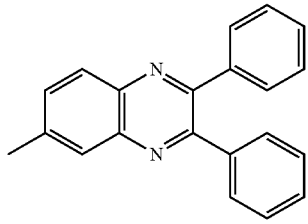
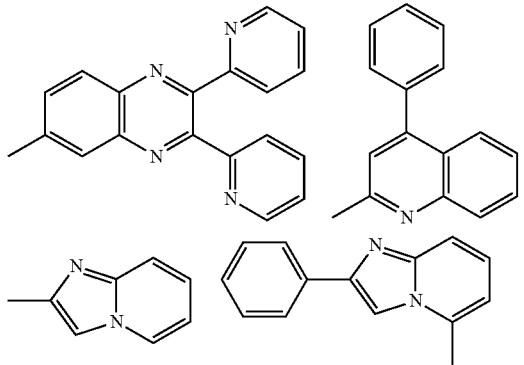
-continued
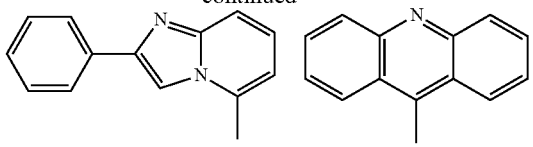
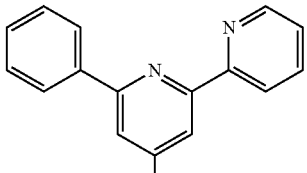
$L^6$ is selected from, for example, the following group:
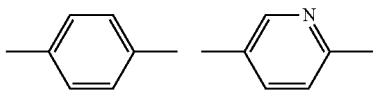
$Ar^c$ is selected from, for example, the following group:
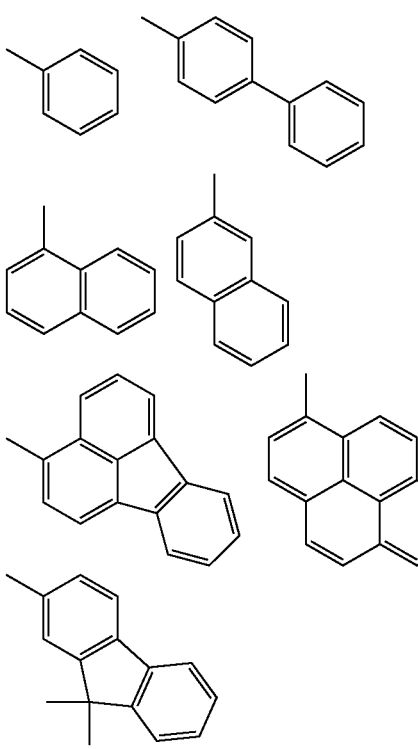
$Ar^b$ is selected from, for example, the following aryl anthranyl groups:
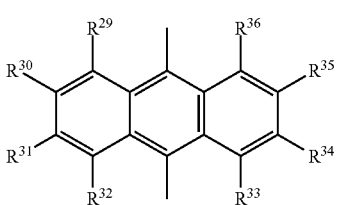

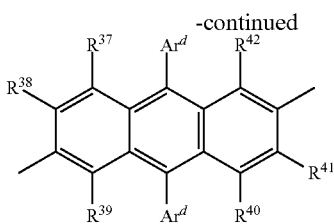

(wherein $R^{29}$ to $R^{42}$ each are independently a hydrogen atom, a halogen atom, an alkyl group having 1 to 20 carbon atoms, an alkoxy group having 1 to 20 carbon atoms, an aryloxy group having 6 to 40 carbon atoms, an aryl group having 6 to 40 carbon atoms which may have a substituent or a heteroaryl group having 3 to 40 carbon atoms; and $Ar^d$ is an aryl group having 6 to 40 carbon atoms which may have a substituent or a heteroaryl group having 3 to 40 carbon atoms).

Also, preferred are the nitrogen-containing heterocyclic derivatives in which all of $R^{29}$ to $R^{36}$ in $Ar^b$ represented by the formula shown above are hydrogen atoms.

In addition to the above compounds, the following compounds (refer to Japanese Patent Application Laid-Open No. 3448/1997) can suitably be used as well:

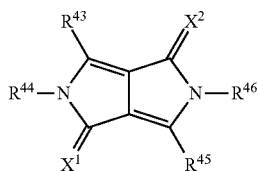

(wherein $R^{43}$ to $R^{46}$ each represent independently a hydrogen atom, a substituted or non-substituted aliphatic group, a substituted or non-substituted alicyclic group, a substituted or non-substituted carbocyclic aromatic group or a substituted or non-substituted heterocyclic group; and $X^1$ and $X^2$ each represent independently an oxygen atom, a sulfur atom or a dicyanomethylene group).

Further, the following compounds (refer to Japanese Patent Application Laid-Open No. 173774/2000) can suitably be used as well:

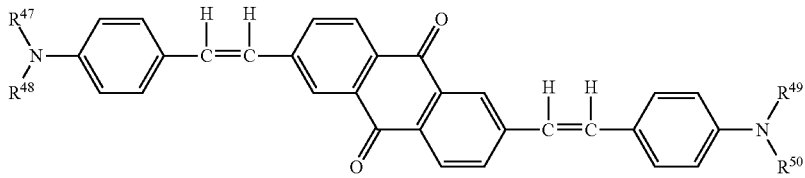

In the formula, $R^{47}$, $R^{48}$, $R^{49}$ and $R^{50}$ are groups which are the same as or different from each other, and they are an aryl group represented by the following formula:

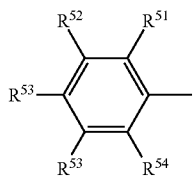

(wherein, $R^{51}$, $R^{52}$, $R^{53}$, $R^{54}$ and $R^{55}$ are groups which are the same as or different from each other, and they are a hydrogen atom or one of them is a saturated or unsaturated alkoxyl group, an alkyl group, an amino group or an alkylamino group).

Further, the nitrogen-containing heterocyclic derivative may be a polymer compound containing the above nitrogen-containing heterocyclic group or nitrogen-containing heterocyclic derivative.

Also, the electron transporting layer contains preferably at least one of nitrogen-containing heterocyclic derivatives represented by the following Formulas (201) to (203):

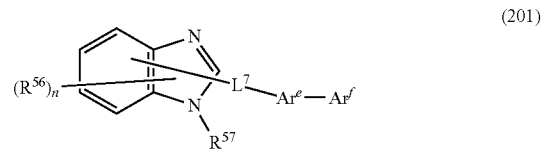

(201)

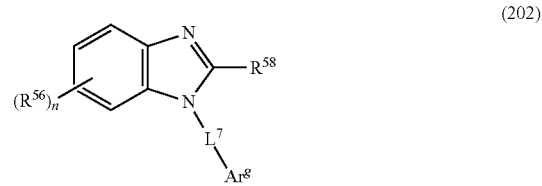

(202)

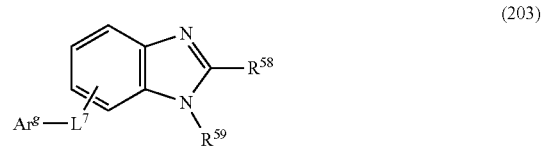

(203)

In Formulas (201) to (203), $R^{56}$ is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; n is an integer of 0 to 4; $R^{57}$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms; $R^{58}$ and $R^{59}$ each are independently a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; $L^7$ is a single bond, an arylene group having 6 to 60 carbon atoms which may have a substituent, a pyridnylene group which may have a substituent, a quinolinylene group which may have a substituent or a fluorenylene group which may have a substituent; $Ar^e$ is an arylene group having 6 to 60 carbon atoms which may have a substituent, a pyridnylene group which may have a substituent or a quinolinylene group which may have a substituent; $Ar^f$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

$Ar^g$ is an aryl group having 6 to 60 carbon atoms which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent or a group represented by —$Ar^e$—$Ar^f$ ($Ar^e$ and $Ar^f$ each are the same as described above).

In Formulas (201) to (203) described above, $R^{56}$ is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The aryl group having 6 to 60 carbon atoms described above is preferably an aryl group having 6 to 40 carbon atoms, more preferably an aryl group having 6 to 20 carbon atoms, and it includes, to be specific, monovalent groups comprising phenyl, naphthyl, anthryl, phenanthryl, naphthacenyl, chrysenyl, pyrenyl, biphenyl, terphenyl, tolyl, t-butylphenyl, (2-phenylpropyl)phenyl, fluoranthenyl, fluorenyl and spirobifluorene, monovalent groups comprising perfluorophenyl, perfluoronaphthyl, perfluoroanthryl, perfluorobiphenyl and 9-phenylanthracene, monovalent groups comprising 9-(1'-naphthyl)anthracene, monovalent groups comprising 9-(2'-naphthyl)anthracene, monovalent groups comprising 6-phenylchrysene, monovalent groups comprising 9-[4-(diphenylamino)phenyl]anthracene and the like, and preferred are phenyl, naphthyl, biphenyl, terphenyl, 9-(10-phenyl)anthryl, 9-[10-(1'-naphthyl)anthryl, 9-[10-(2'-naphthyl)anthryl and the like.

The alkyl group having 1 to 20 carbon atoms is preferably an alkyl group having 1 to 6 carbon atoms, and it includes, to be specific, methyl, ethyl, propyl, butyl, pentyl, hexyl and the like, and in addition thereto, it includes haloalkyl groups such as trifluoromethyl and the like. The alkyl groups having 3 or more carbon atoms may be linear, cyclic or branched.

The alkoxy group having 1 to 20 carbon atoms is preferably an alkoxy group having 1 to 6 carbon atoms, and it includes, to be specific, methoxy, ethoxy, propoxy, butoxy, pentyloxy, hexyloxy and the like, and the alkoxy groups having 3 or more carbon atoms may be linear, cyclic or branched.

The substituents of the respective groups represented by $R^{56}$ include a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent The halogen atom includes fluorine, chlorine, bromine and iodine.

The alkyl group having 1 to 20 carbon atoms, the alkoxy group having 1 to 20 carbon atoms and the aryl group having 6 to 40 carbon atoms include the same groups as described above.

The aryloxy group having 6 to 40 carbon atoms includes, for example, phenoxy, biphenyloxy and the like.

The heteroaryl group having 6 to 40 carbon atoms includes, for example, pyrrolyl, furyl, thienyl, silolyl, pyridyl, quinolyl, isoquinolyl, benzofuryl, imidazolyl, pyrimidyl, carbazolyl, selenophenyl, oxadiazolyl, triazolyl and the like.

The term n is an integer of 0 to 4, preferably 0 to 2.

In Formula (201) described above, $R^{57}$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples, the preferred carbon numbers and the substituents of the above respective groups are the same as those explained for R described above.

In Formulas (202) and (203) described above, $R^{58}$ and $R^{59}$ each are independently a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples, the preferred carbon numbers and the substituents of the above respective groups are the same groups as those explained for $R^{56}$ described above.

In Formulas (201) to (203) described above, $L^7$ is a single bond, an arylene group having 6 to 60 carbon atoms which may have a substituent, a pyridinylene group which may have a substituent, a quinolinylene group which may have a substituent or a fluorenylene group which may have a substituent.

The arylene group having 6 to 60 carbon atoms is preferably an arylene group having 6 to 40 carbon atoms, more preferably an arylene group having 6 to 20 carbon atoms, and it includes, to be specific, divalent groups formed by removing one hydrogen atom from the aryl groups explained for R described above.

The substituents of the respective groups represented by $L^7$ are the same groups as those explained for $R^{56}$ described above.

Further, $L^7$ is preferably a group selected from the group consisting of:

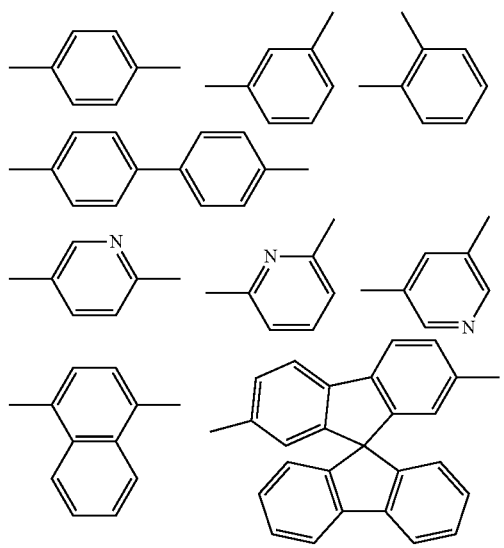

In Formula (201) described above, Ar$^e$ is an arylene group having 6 to 60 carbon atoms which may have a substituent, a pyridinylene group which may have a substituent or a quinolinylene group which may have a substituent. The substituents of the respective groups represented by Ar$^e$ and Ar$^g$ each are the same as those explained for R described above.

Also, Ar$^e$ is preferably any group selected from condensed ring groups represented by the following Formulas (101) to (110):

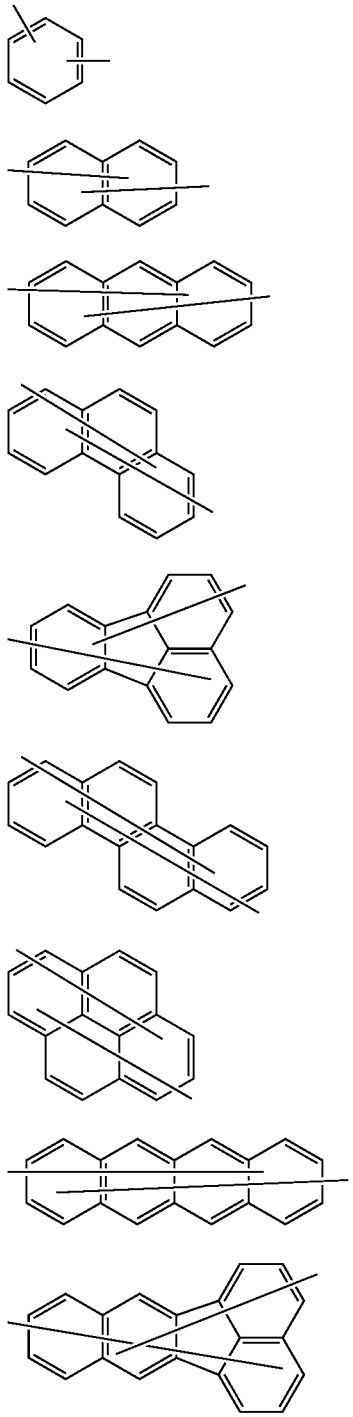

(101)
(102)
(103)
(104)
(105)
(106)
(107)
(108)
(109)

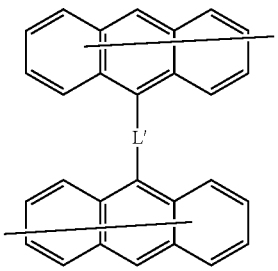

(110)

In Formulas (101) to (110) described above, the respective condensed rings may be combined with a bonding group comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups is present, the above bonding groups may be the same as or different from each other. The specific examples of the above respective groups include the same groups as described above.

In Formula (101) described above, L' is a single bond or a group selected from the group consisting of:

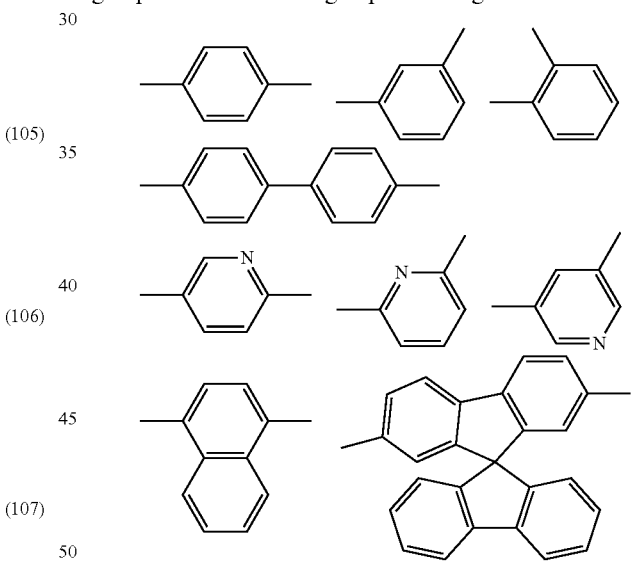

Ar$^e$ represented by Formulas (103) described above is preferably condensed ring groups represented by the following Formulas (111) to (125):

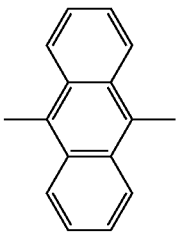

(111)

(112)
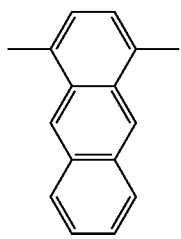
(113)
(114)
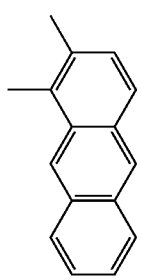
(115)
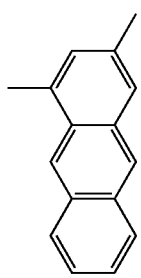
(116)
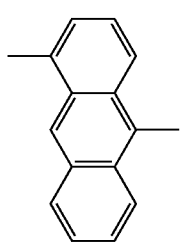
(117)
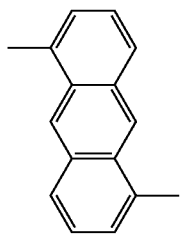
(118)
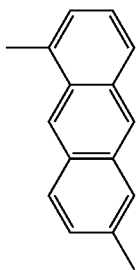
(119)
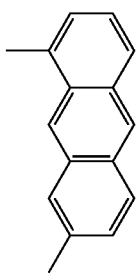
(120)
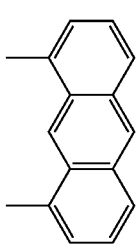
(121)
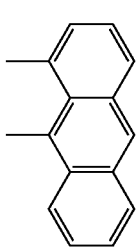
(122)
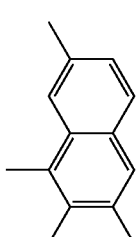
(123)
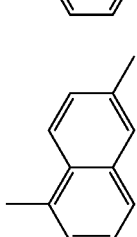

(124)

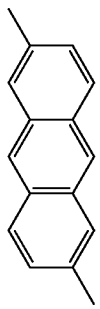

(125)

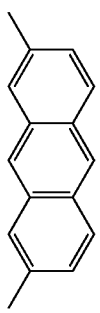

In Formulas (111) to (125) described above, the respective condensed rings may be combined with a bonding group comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups is present, the above bonding groups may be the same as or different from each other. The specific examples of the above respective groups include the same groups as described above.

In Formula (201) described above, $Ar^f$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples, the preferred carbon numbers and the substituents of the above respective groups are the same as those explained for $R^{56}$ described above.

In Formulas (202) and (203) described above, $Ar^g$ is an aryl group having 6 to 60 carbon atoms which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent or a group represented by —$Ar^e$—$Ar^f$ ($Ar^e$ and $Ar^f$ each are the same as described above).

The specific examples, the preferred carbon numbers and the substituents of the above respective groups are the same as those explained for $R^{56}$ described above.

Also, $Ar^g$ is preferably any group selected from condensed ring groups represented by the following Formulas (126) to (135):

(126)

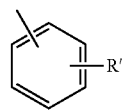

(127)

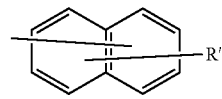

(128)

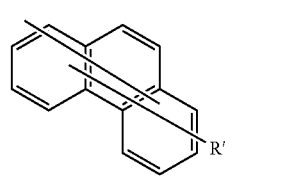

(129)

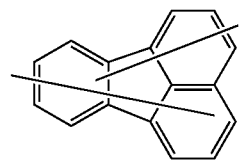

(130)

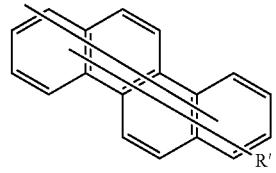

(131)

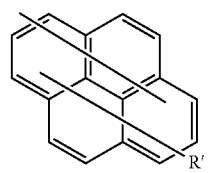

(132)

(133)

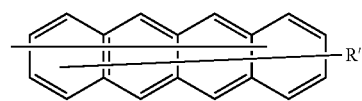

(134)

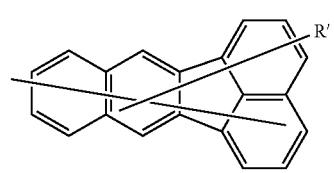

(135)

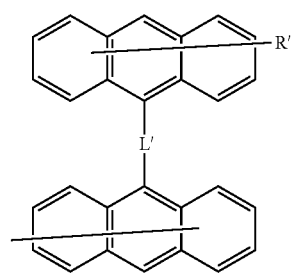

In Formulas (126) to (135) described above, the respective condensed rings may be combined with a bonding group comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups is present, the above bonding groups may be the same as or different from each other. The specific examples of the above respective groups include the same groups as described above.

In Formula (135) described above, L' is the same as described above.

In Formulas (126) to (135) described above, R' is a hydrogen atom, an alkyl group having 1 to 20 carbon atoms which may have a substituent, an aryl group having 6 to 40 carbon atoms which may have a substituent or a heteroaryl group having 3 to 40 carbon atoms which may have a substituent. The specific examples of the above respective groups include the same groups as described above.

Ar$^g$ represented by Formula (128) is preferably condensed ring groups represented by the following Formulas (136) to (158):

(136)

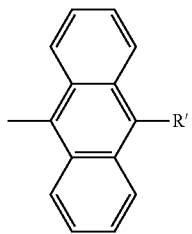
(137)

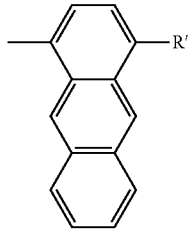
(138)

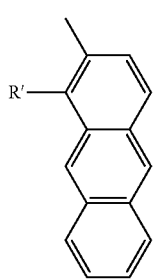
(139)

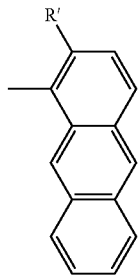
(140)

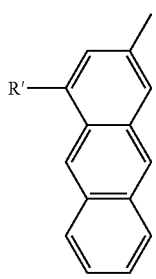
(141)

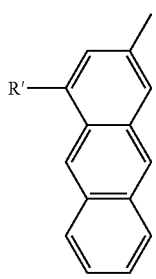
(142)

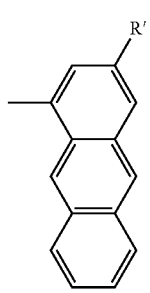
(143)

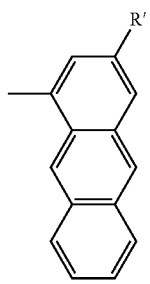
(143)

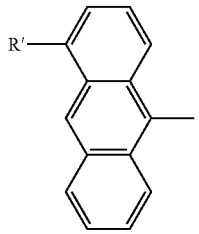
(144)

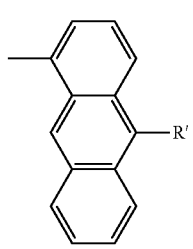

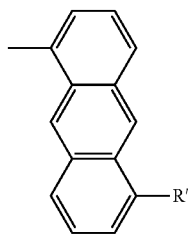
(145)

(146)
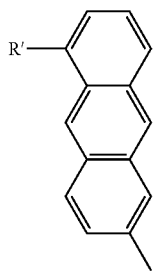
(147)
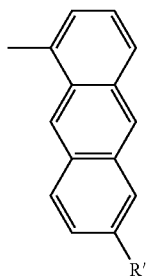
(148)
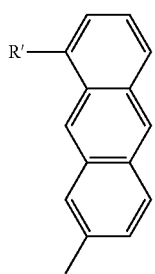
(149)
(150)
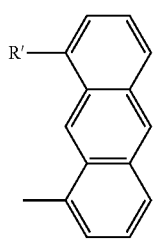
(151)
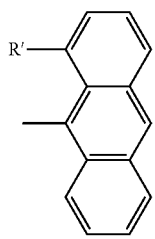
(152)
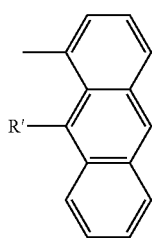
(153)
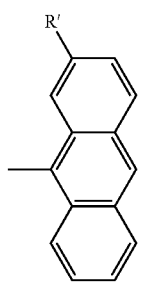
(154)
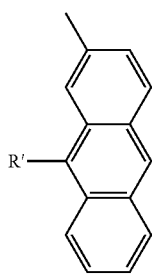
(155)
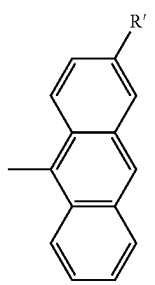
(156)
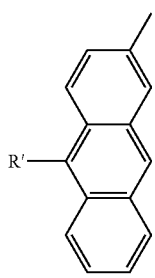

(157)

(158)

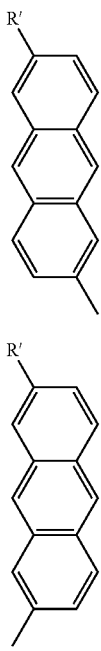

In Formulas (126) to (135) described above, the respective condensed rings may be combined with a bonding group comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups is present, the above bonding groups may be the same as or different from each other. The specific examples of the above respective groups include the same groups as described above. R' is the same as described above.

Further, it is preferred that $Ar^f$ and $Ar^g$ each are independently a group selected from the group consisting of:

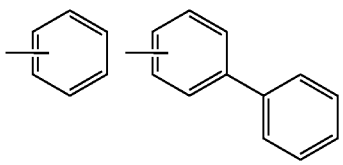

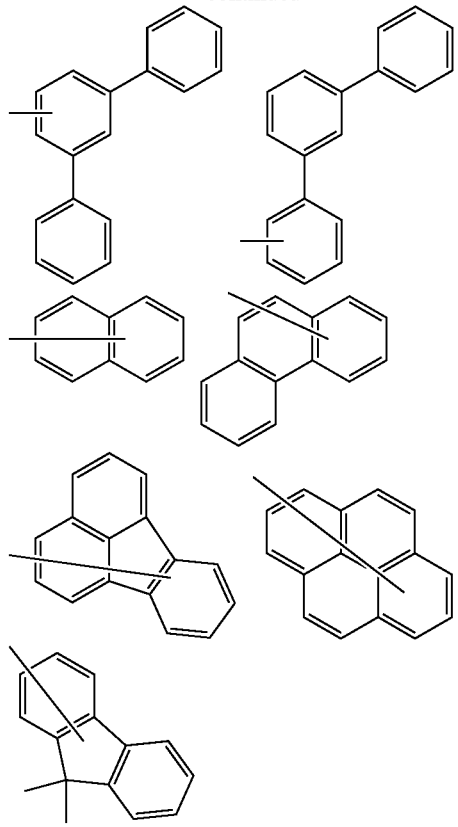

The specific examples of the nitrogen-containing heterocyclic derivative of the present invention represented by Formulas (201) to (203) described above shall be shown below, but the present invention shall not be restricted to these compounds shown as the examples.

In the following tables, HAr represents:

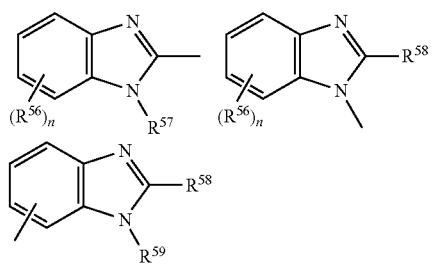

in Formulas (201) to (203) described above.

| | HAr | $L^7$ | $Ar^e$ | $Ar^f$ |
|---|---|---|---|---|
| 1-1 | | | | |

-continued

| HAr | L⁷ | Arᵉ | Arᶠ |
|---|---|---|---|

(Table contents are chemical structures for entries 2–7.)

-continued
| | HAr | L⁷ | Arᵉ | Arᶠ |
|---|---|---|---|---|
| 8 | 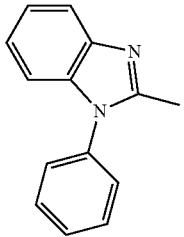 | 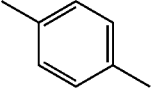 | 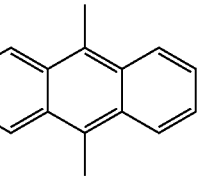 | 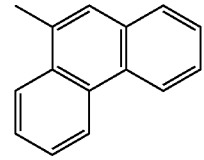 |
| 9 | 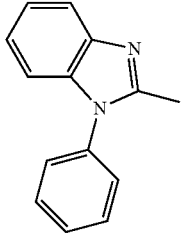 | 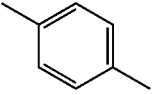 | 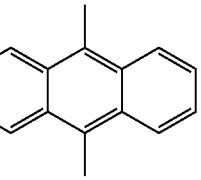 | 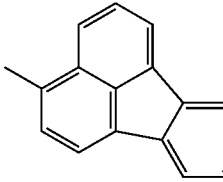 |
| 10 | 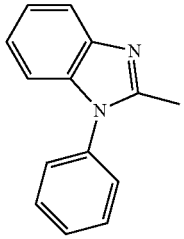 | 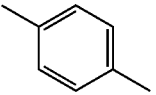 | 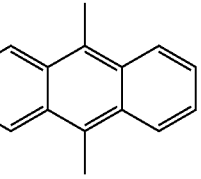 | 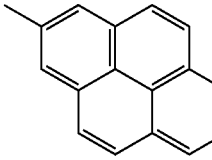 |
| 11 | 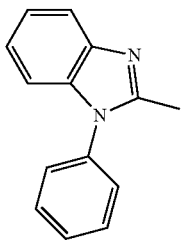 | 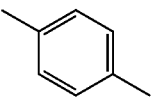 | 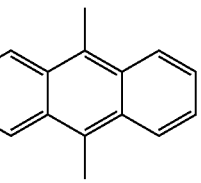 | 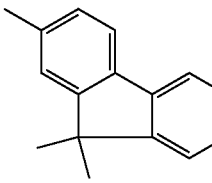 |
| 12 | 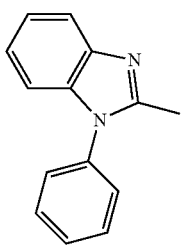 | 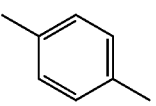 | 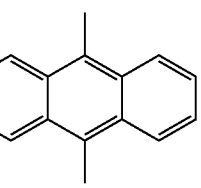 | 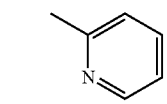 |
| 13 | 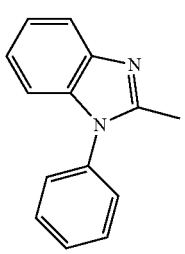 | 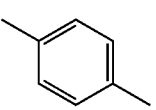 | 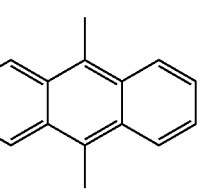 | 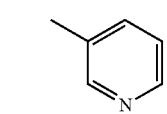 |

-continued
| | HAr—L⁷—Arᵉ—Arᶠ | | | |
|---|---|---|---|---|
| | HAr | L⁷ | Arᵉ | Arᶠ |
| 14 | | | | |
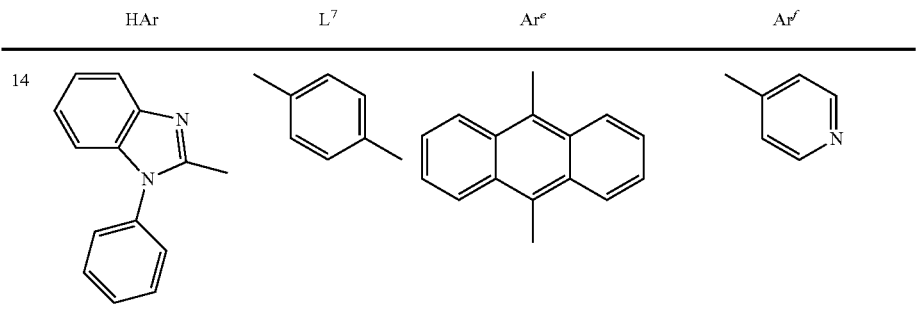
| | HAr—L⁷—Arᵉ—Arᶠ | | | |
|---|---|---|---|---|
| | HAr | L⁷ | Arᵉ | Arᶠ |
| 2-1 | | | | |
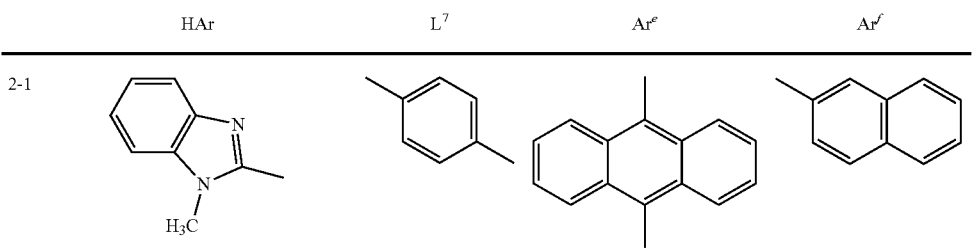
| 2 | | | | |
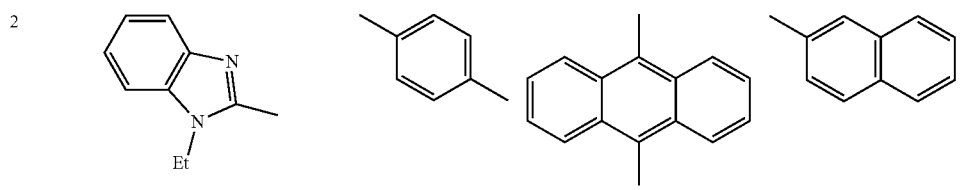
| 3 | | | | |
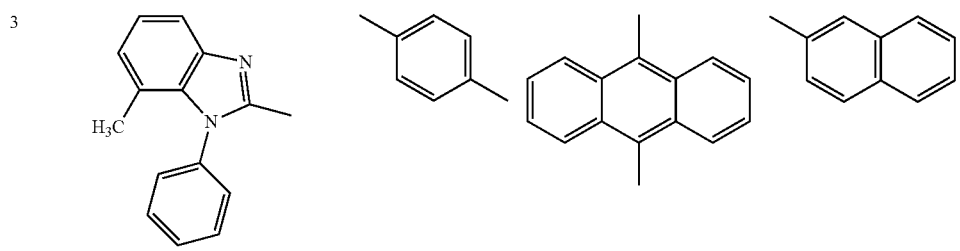
| 4 | | | | |
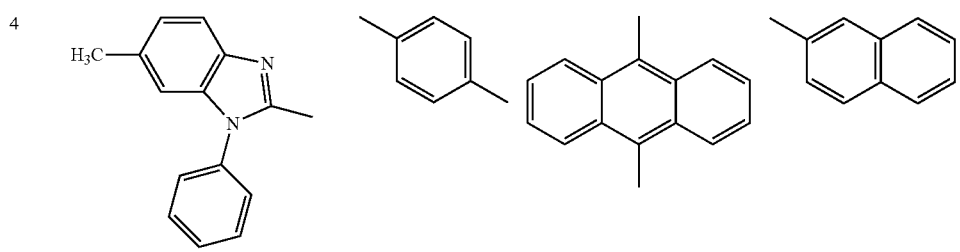

-continued
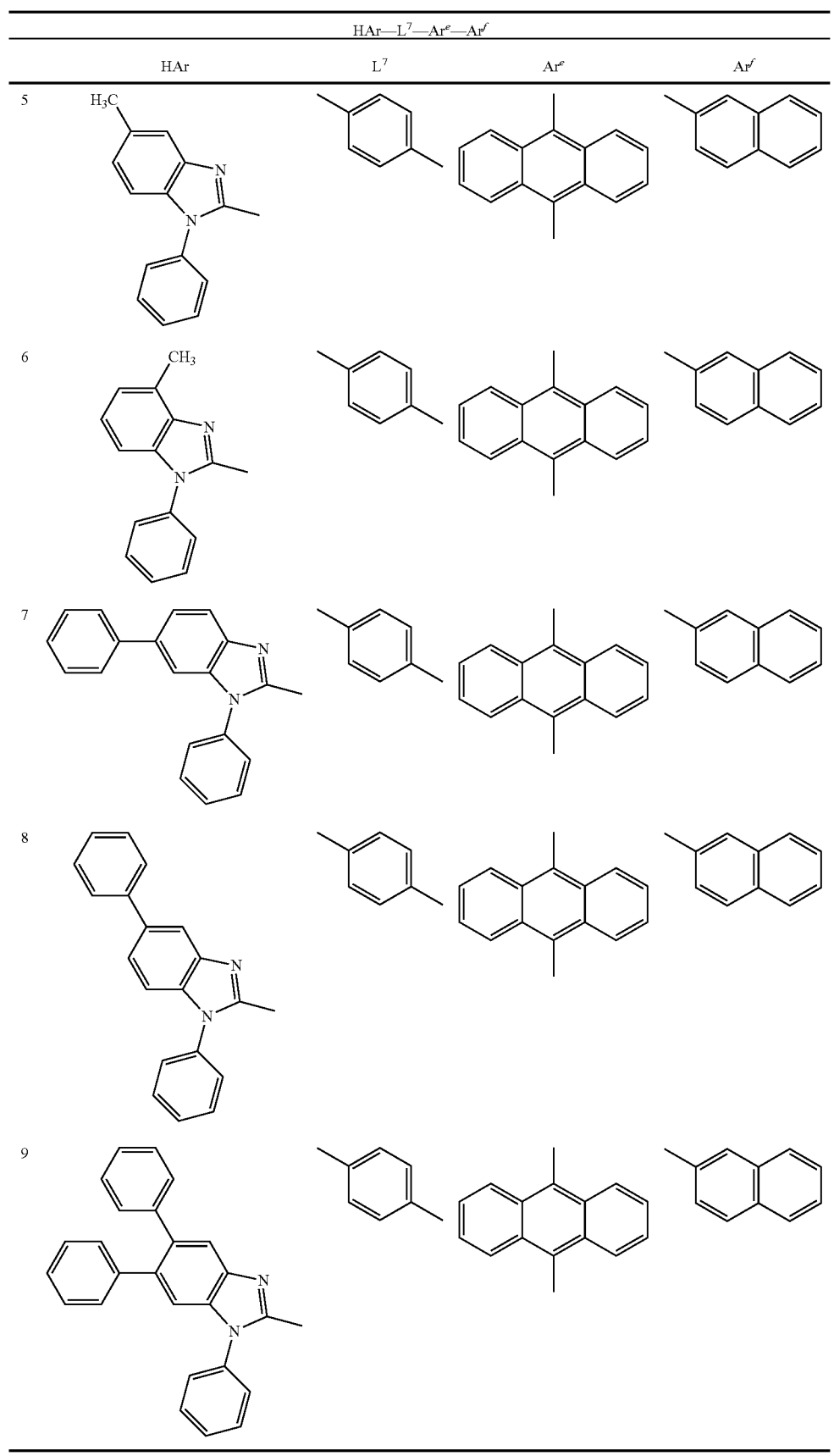

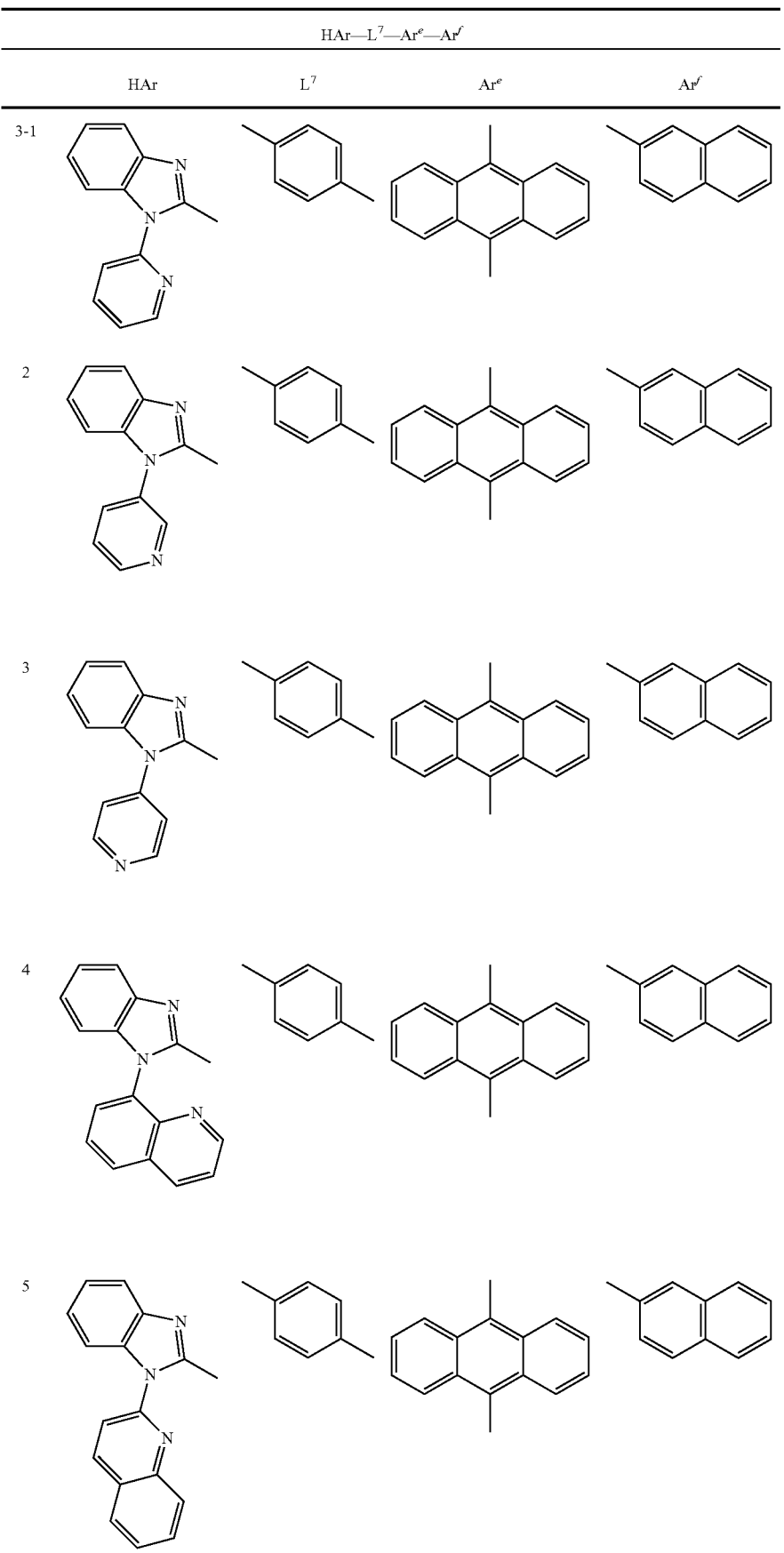

-continued
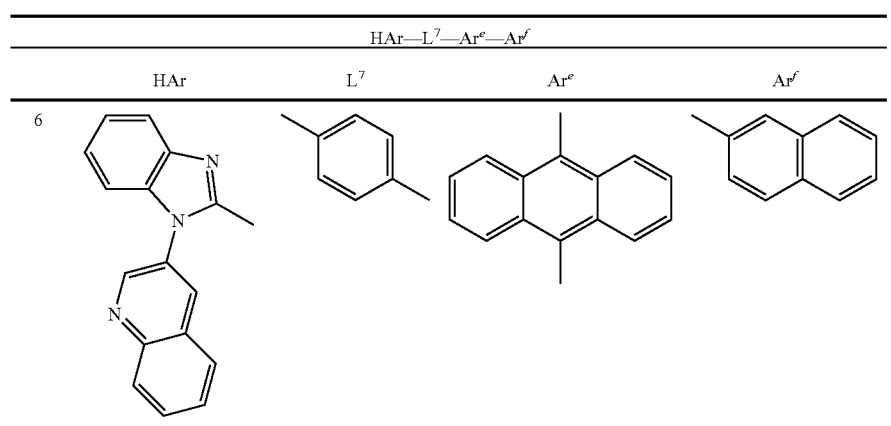
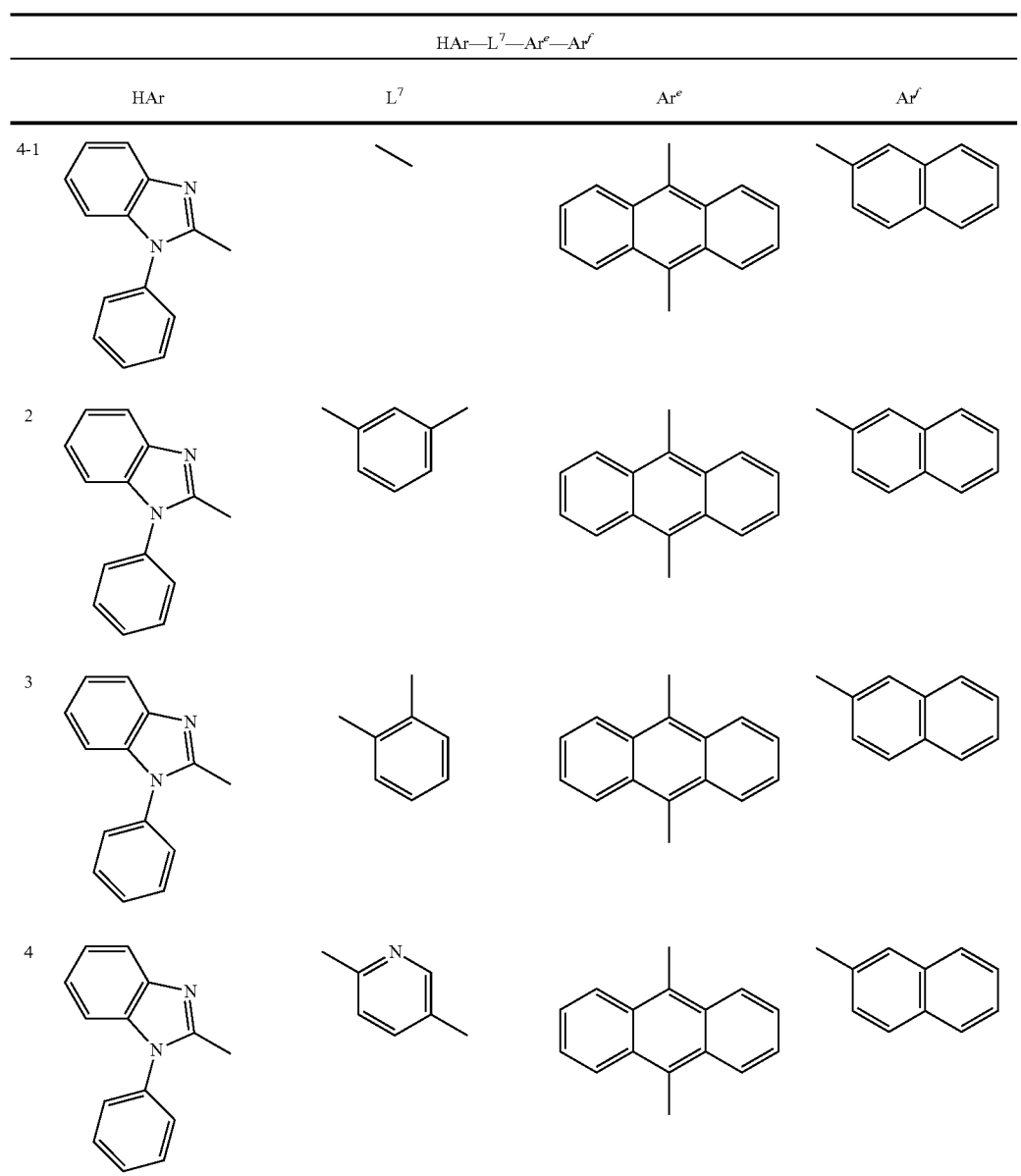

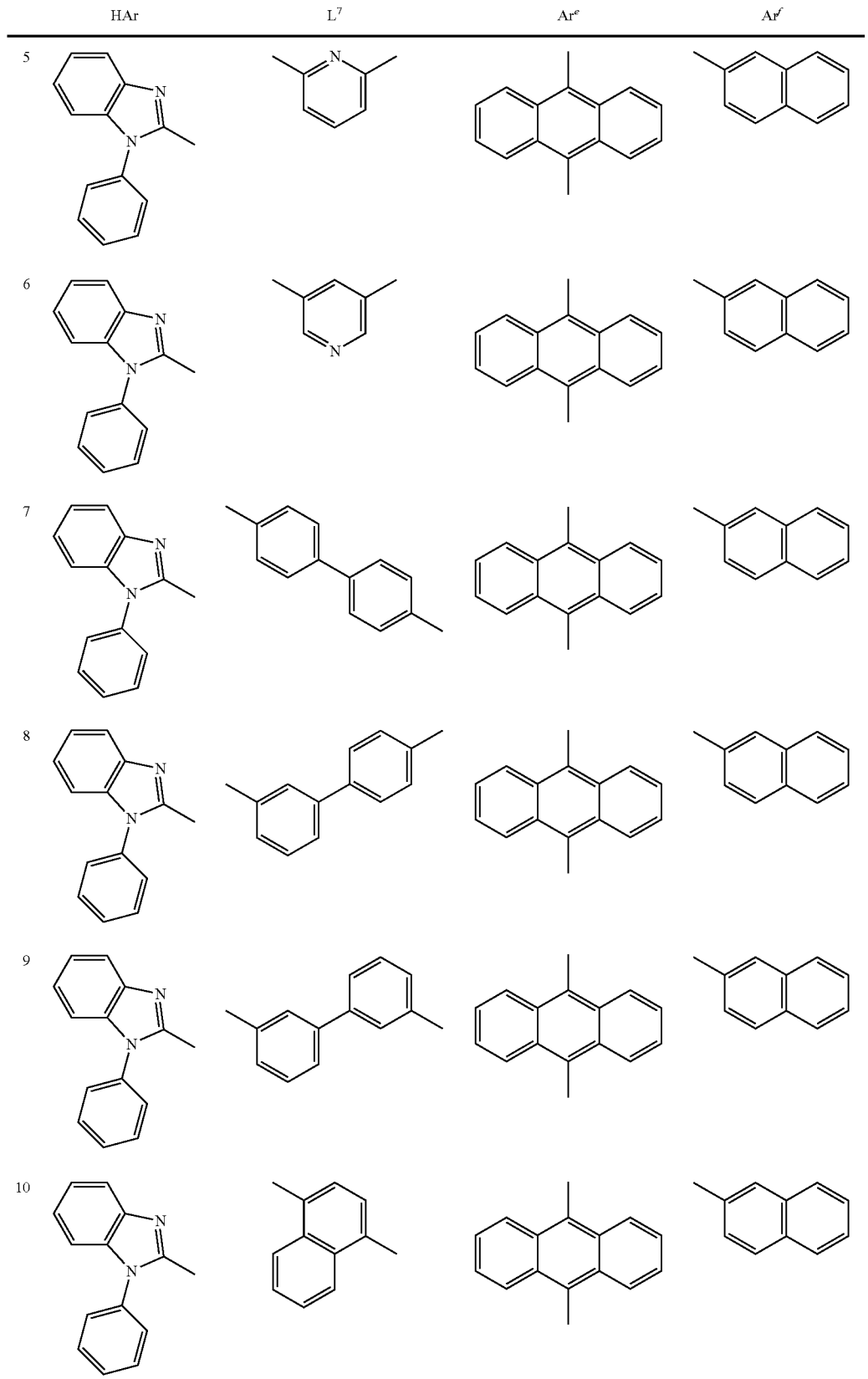

-continued
| | HAr—L⁷—Arᵉ—Arᶠ | | | |
|---|---|---|---|---|
| | HAr | L⁷ | Arᵉ | Arᶠ |
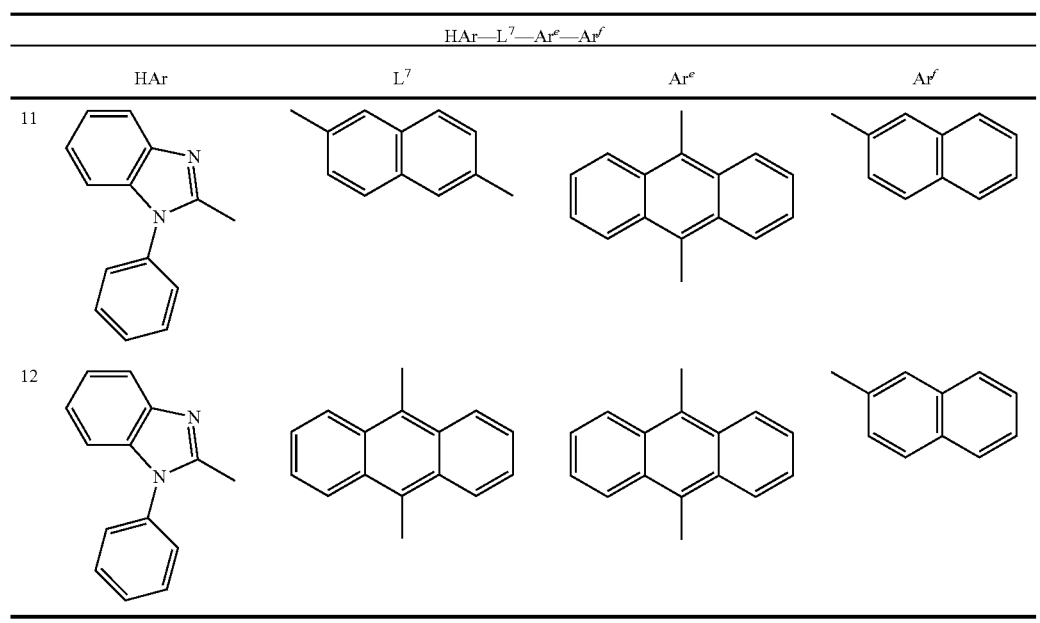
| | HAr—L⁷—Arᵉ—Arᶠ | | | |
|---|---|---|---|---|
| | HAr | L⁷ | Arᵉ | Arᶠ |
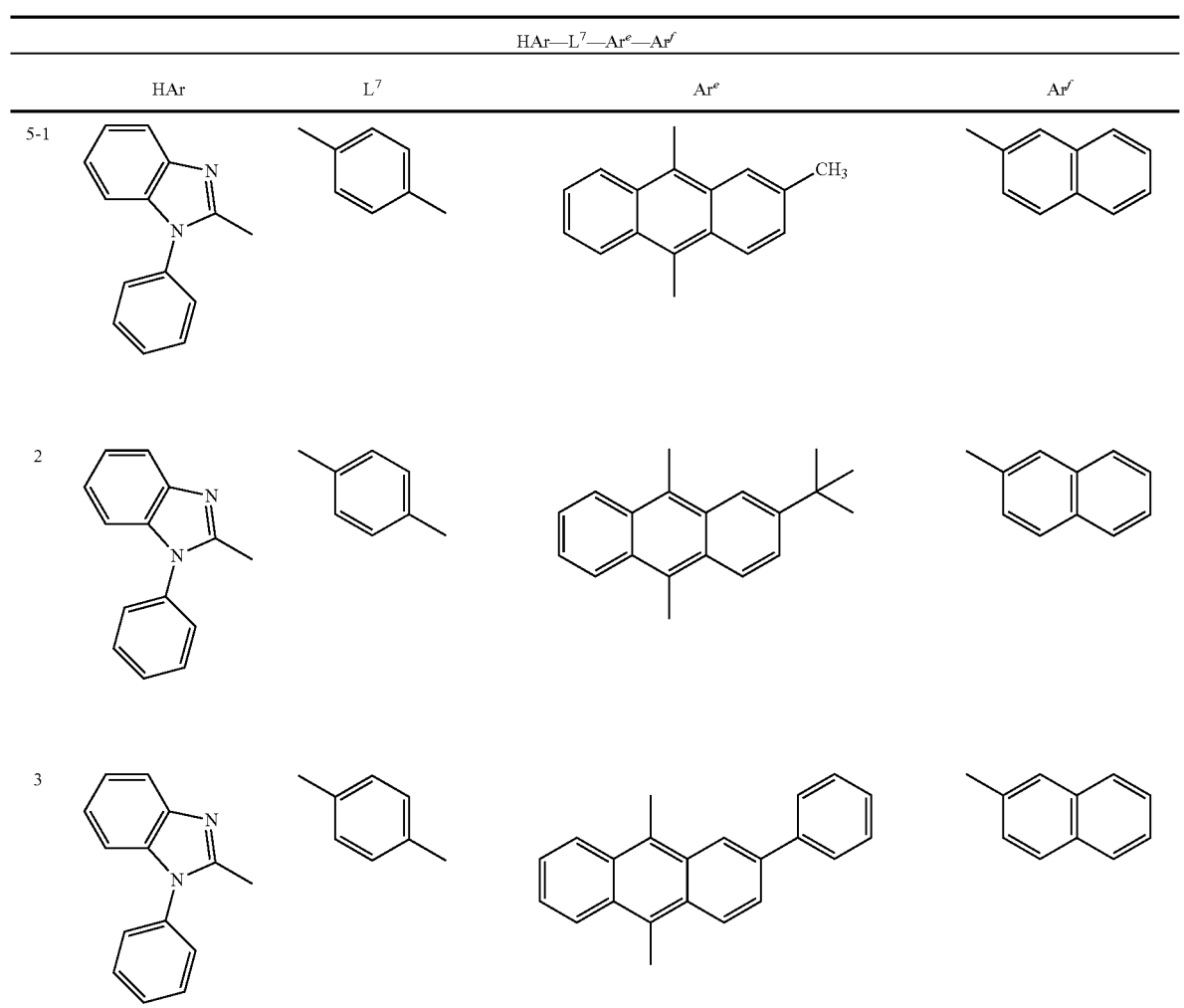

-continued
| | HAr—L⁷—Arᵉ—Ar^f | | | |
|---|---|---|---|---|
| | HAr | L⁷ | Arᵉ | Ar^f |
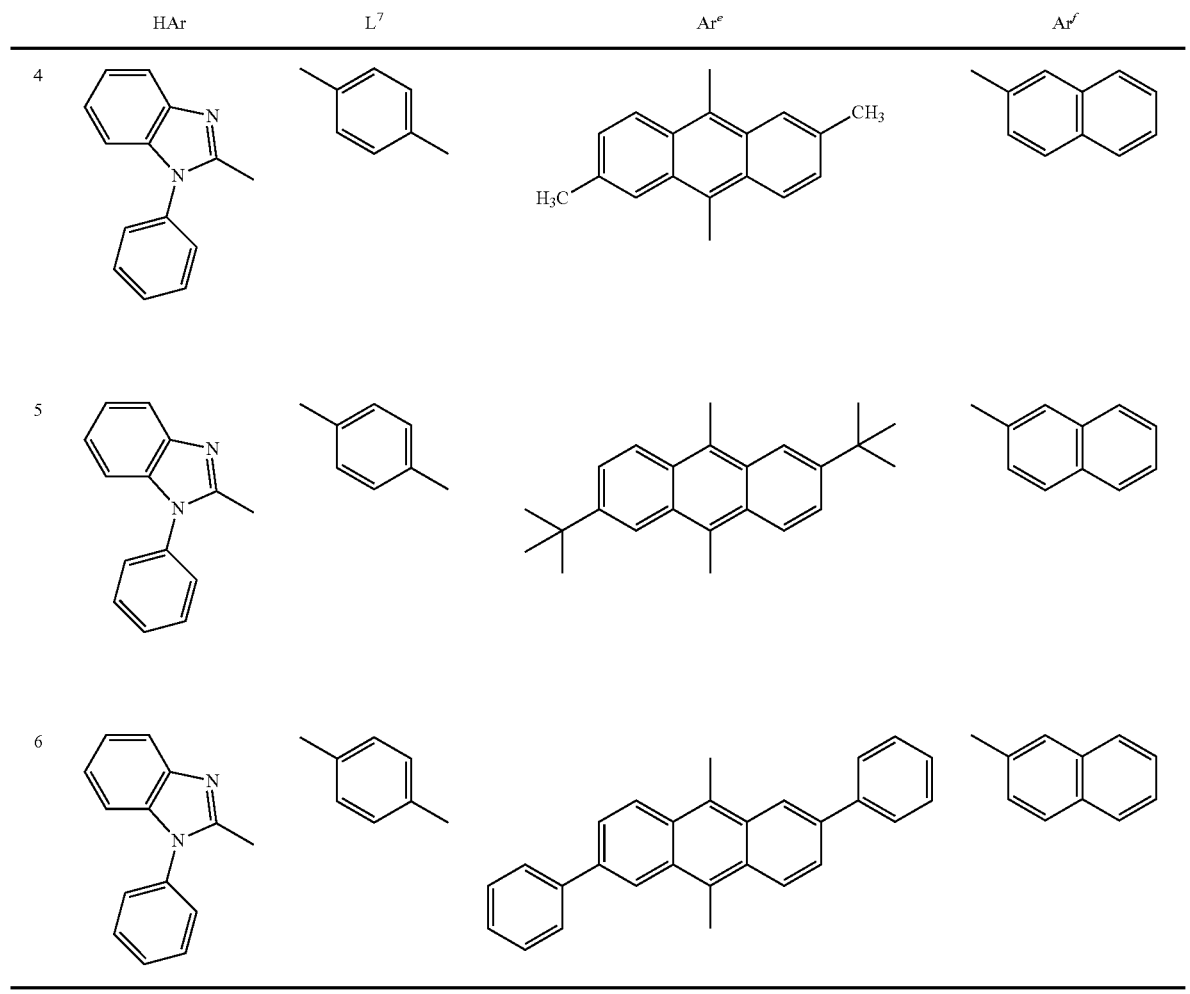
| | HAr—L⁷—Arᵉ—Ar^f | | | |
|---|---|---|---|---|
| | HAr | L⁷ | Arᵉ | Ar^f |
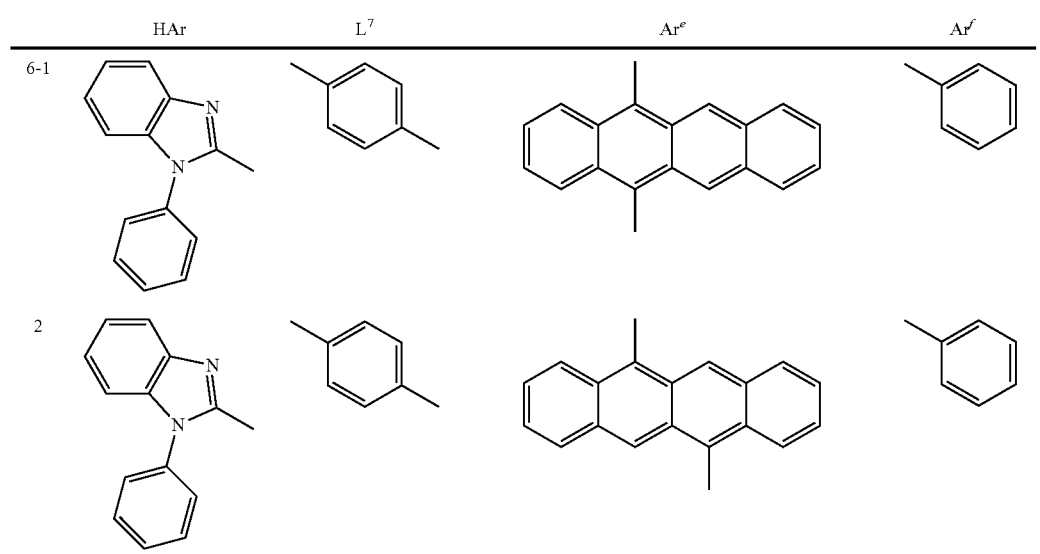

-continued
| HAr—L⁷—Arᵉ—Arᶠ ||||
|---|---|---|---|
| HAr | L⁷ | Arᵉ | Arᶠ |
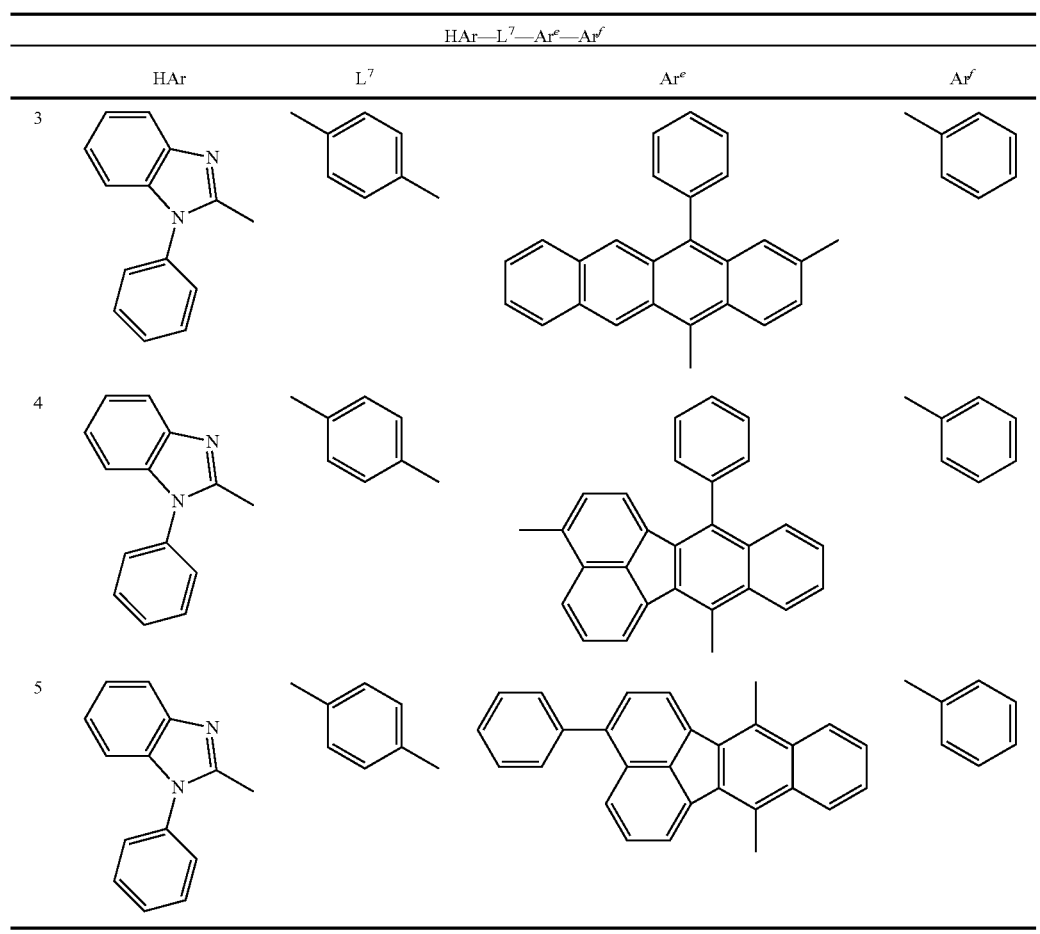
| HAr—L⁷—Arᵉ—Arᶠ ||||
|---|---|---|---|
| HAr | L⁷ | Arᵉ | Arᶠ |
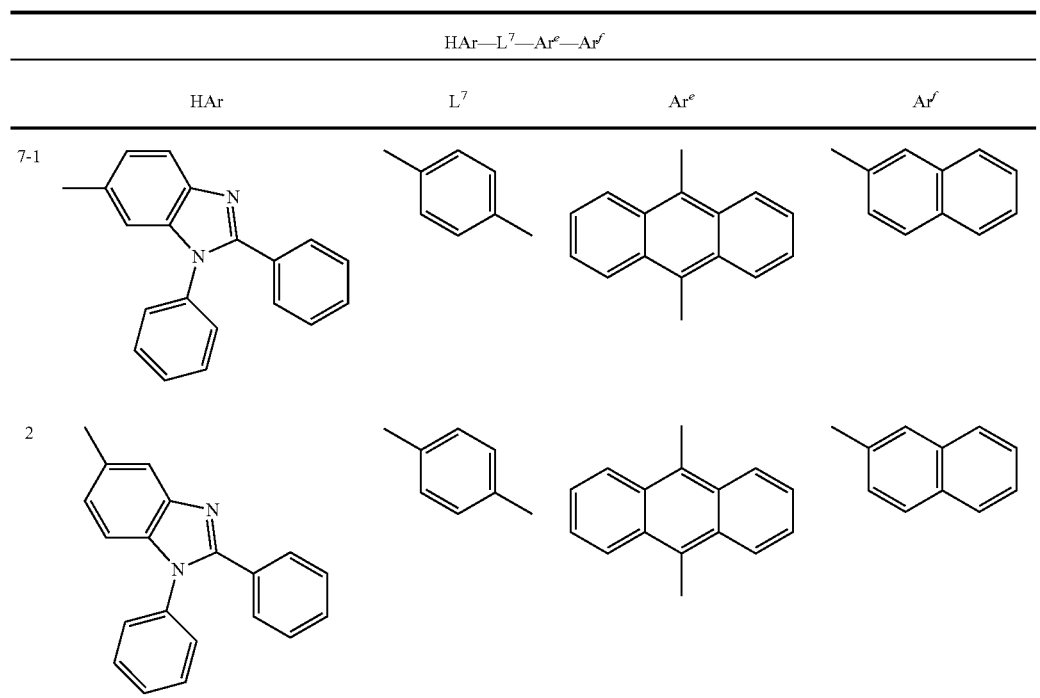

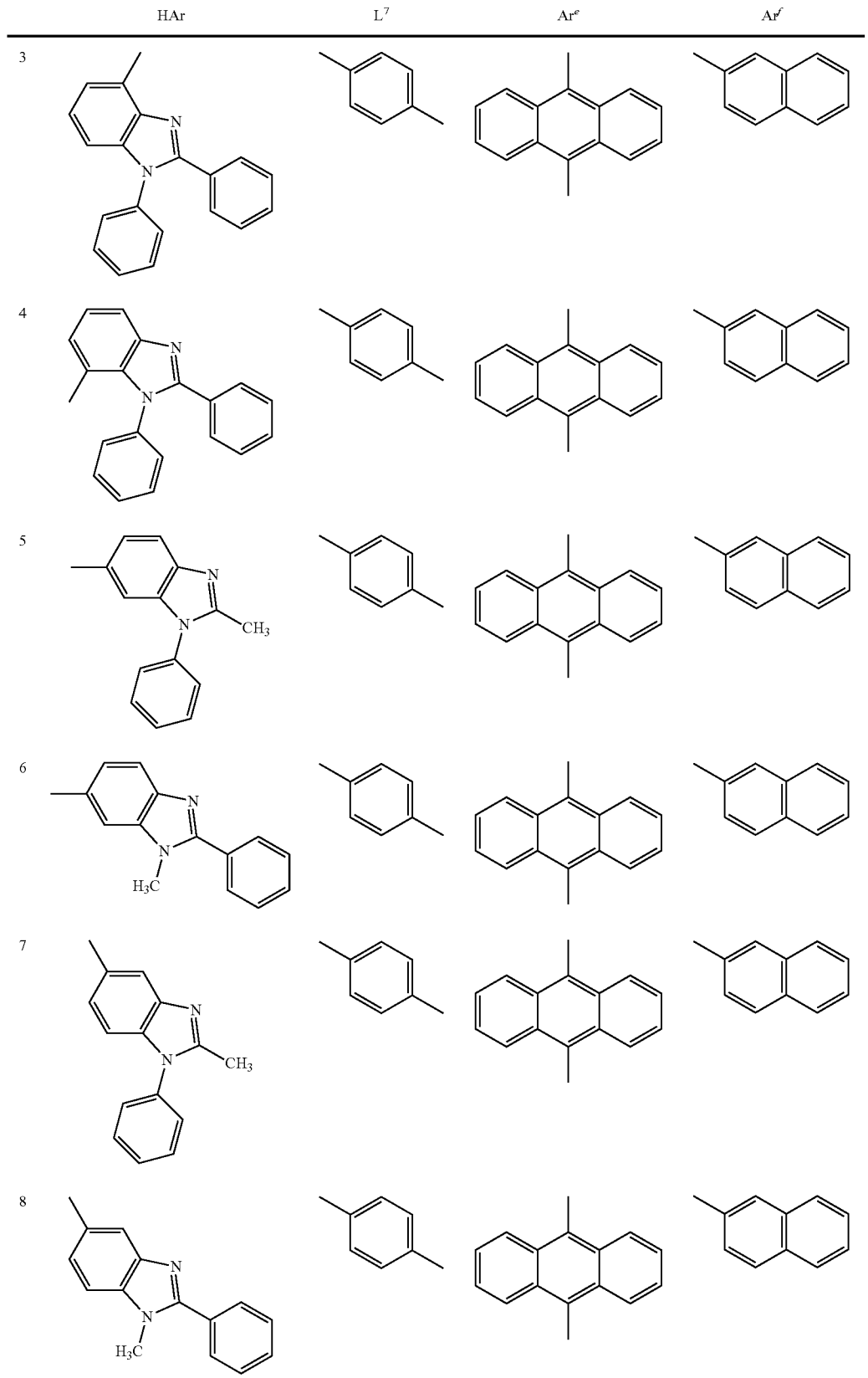

-continued
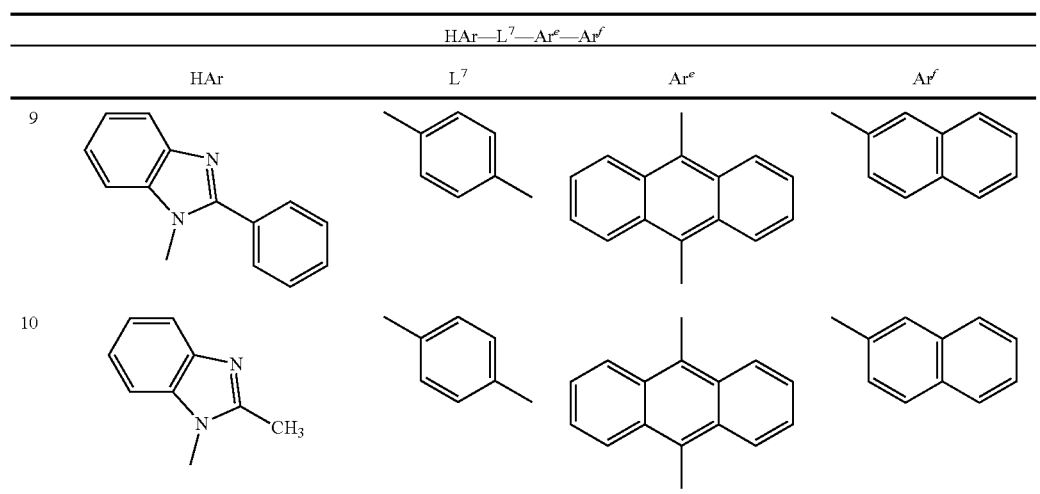
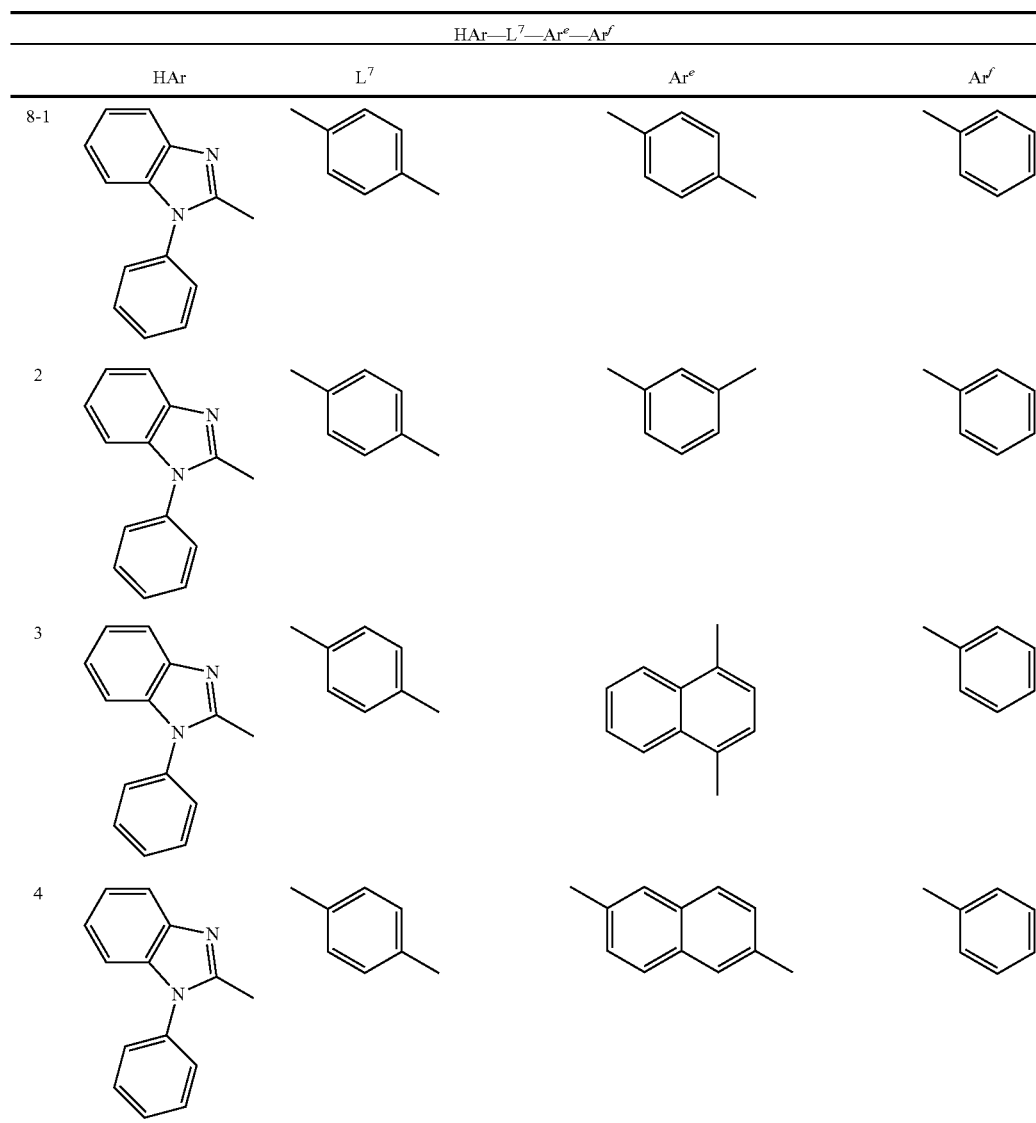

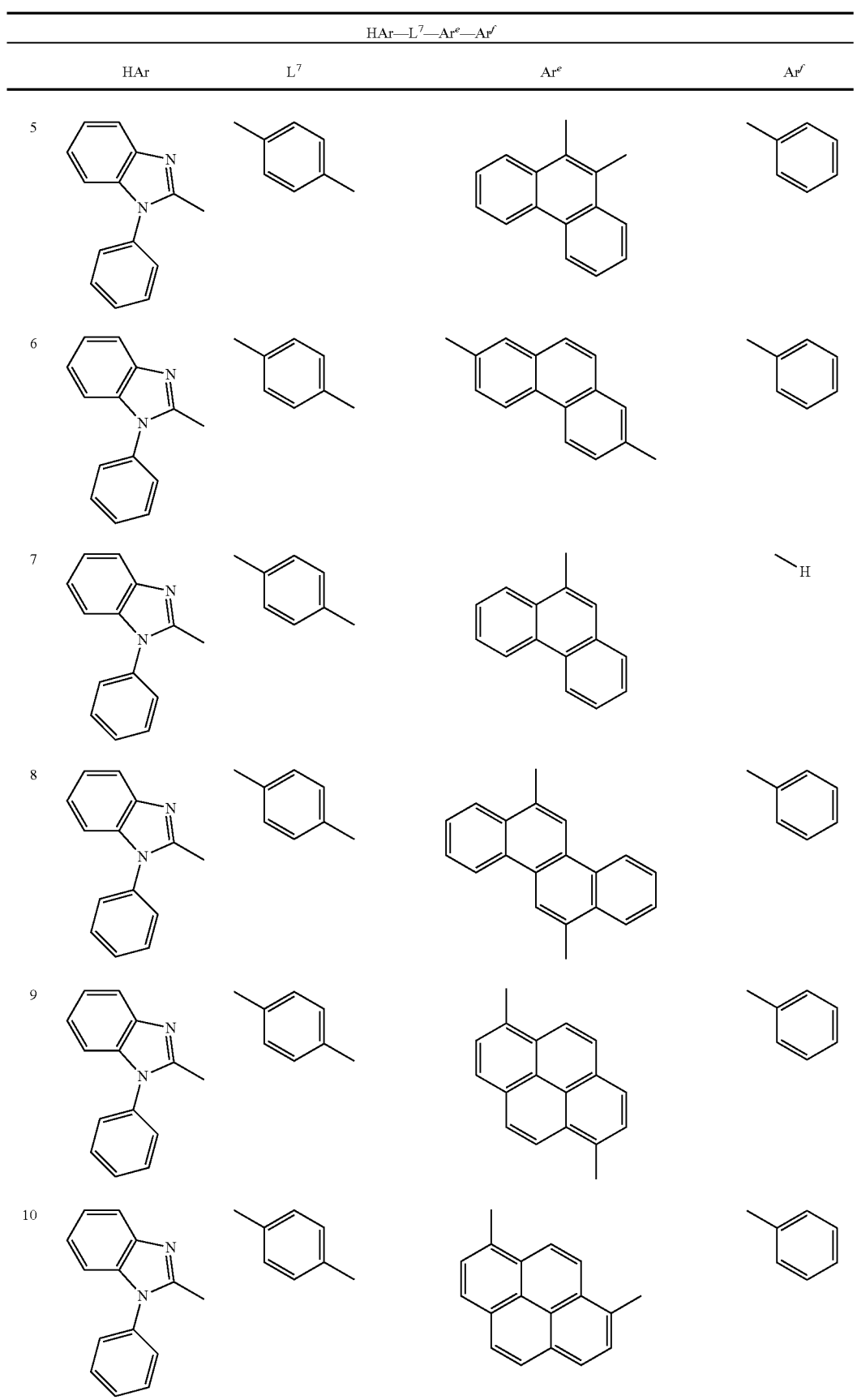

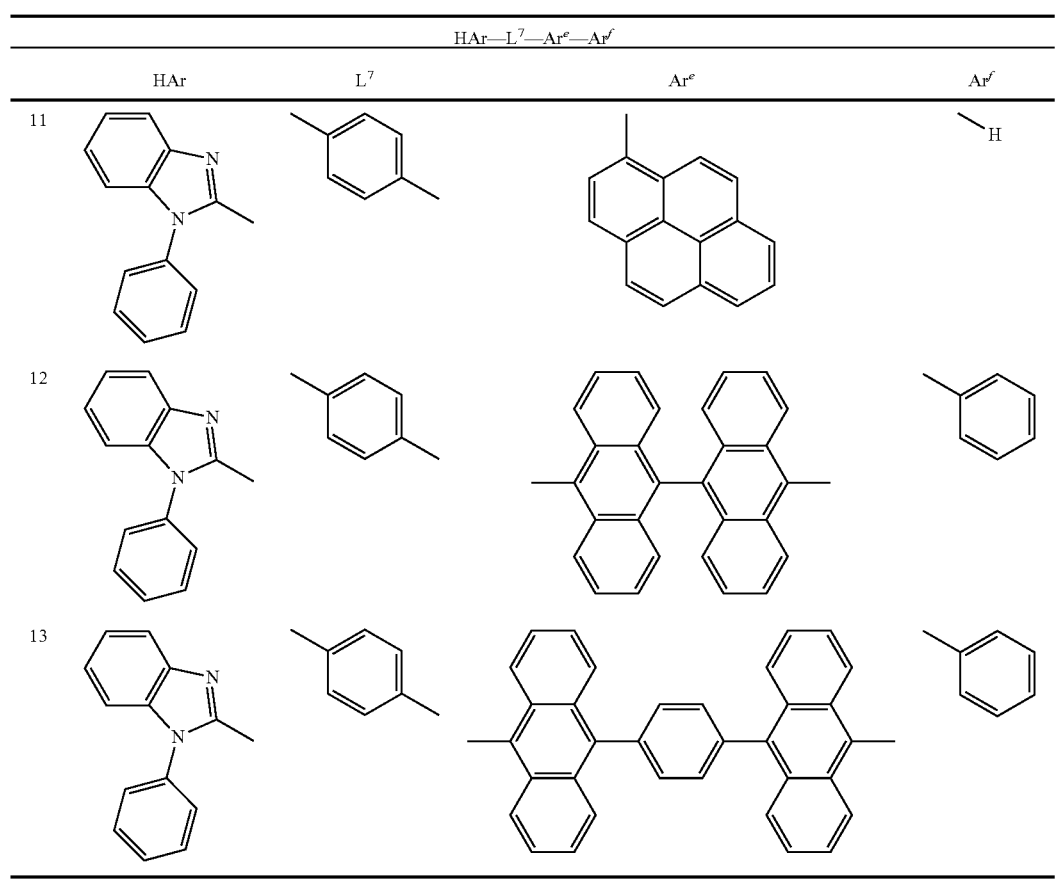
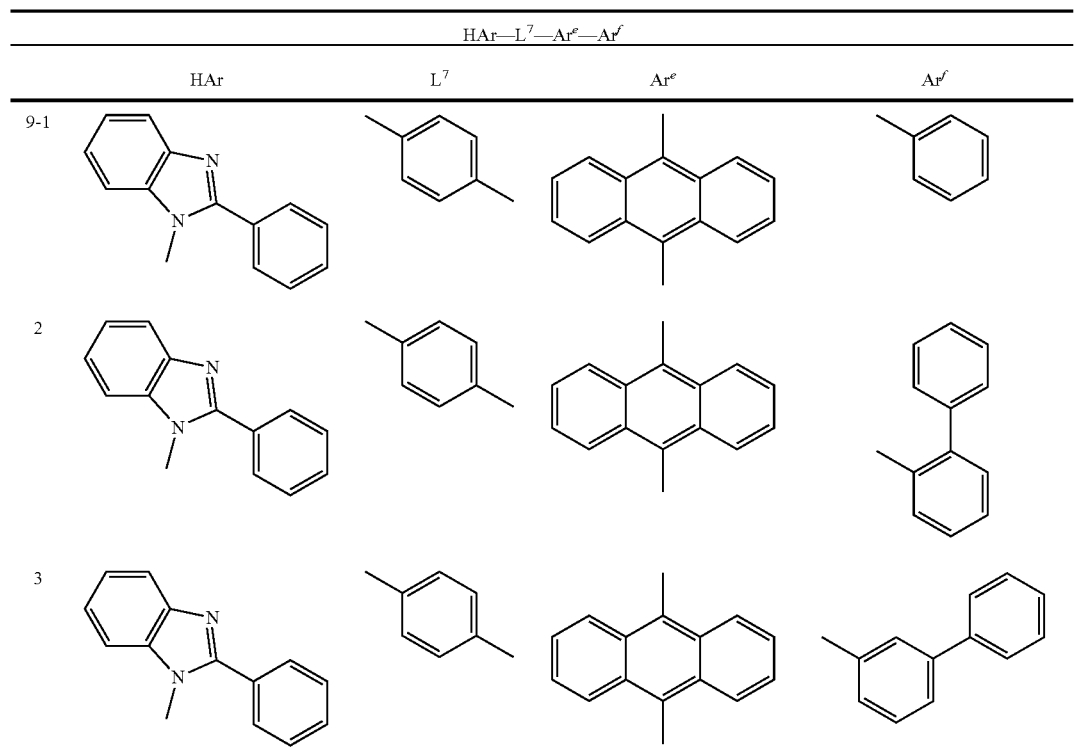

-continued
| | HAr | L⁷ | Arᵉ | Arᶠ |
|---|---|---|---|---|
| 4 | 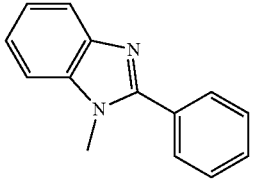 | 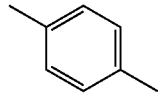 | 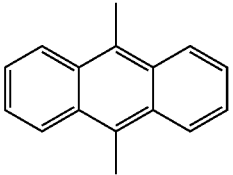 | 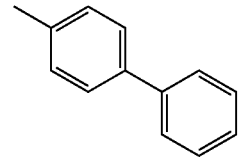 |
| 5 | 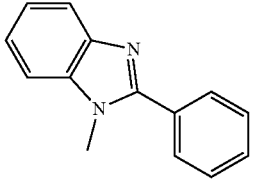 | 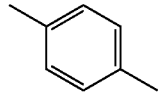 | 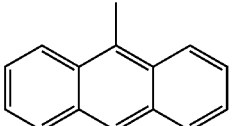 | 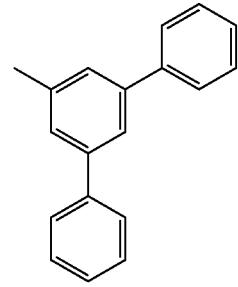 |
| 6 | 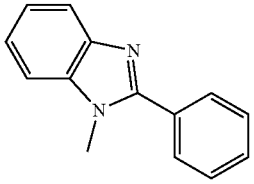 | 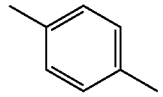 | 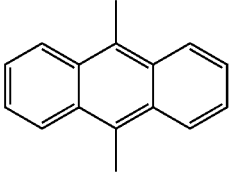 | 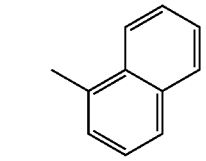 |
| 7 | 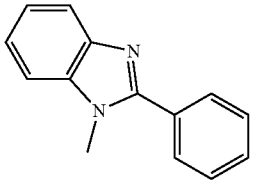 | 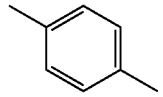 | 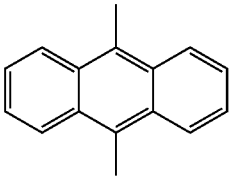 | 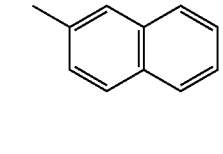 |
| 8 | 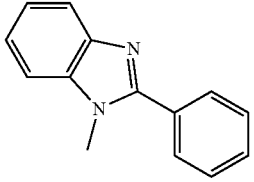 | 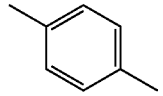 | 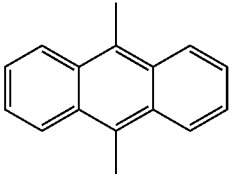 | 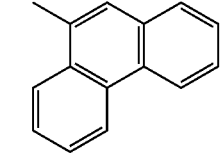 |
| 9 | 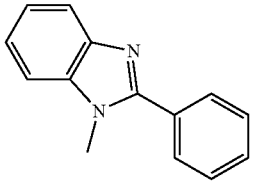 | 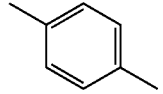 | 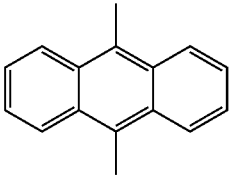 | 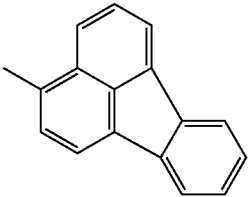 |
| 10 | 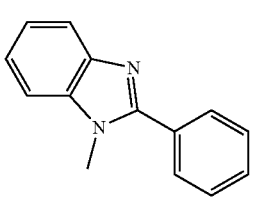 | 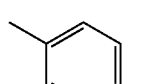 | 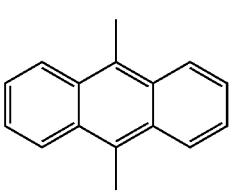 | 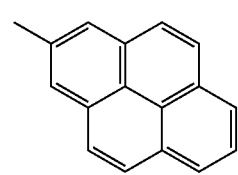 |

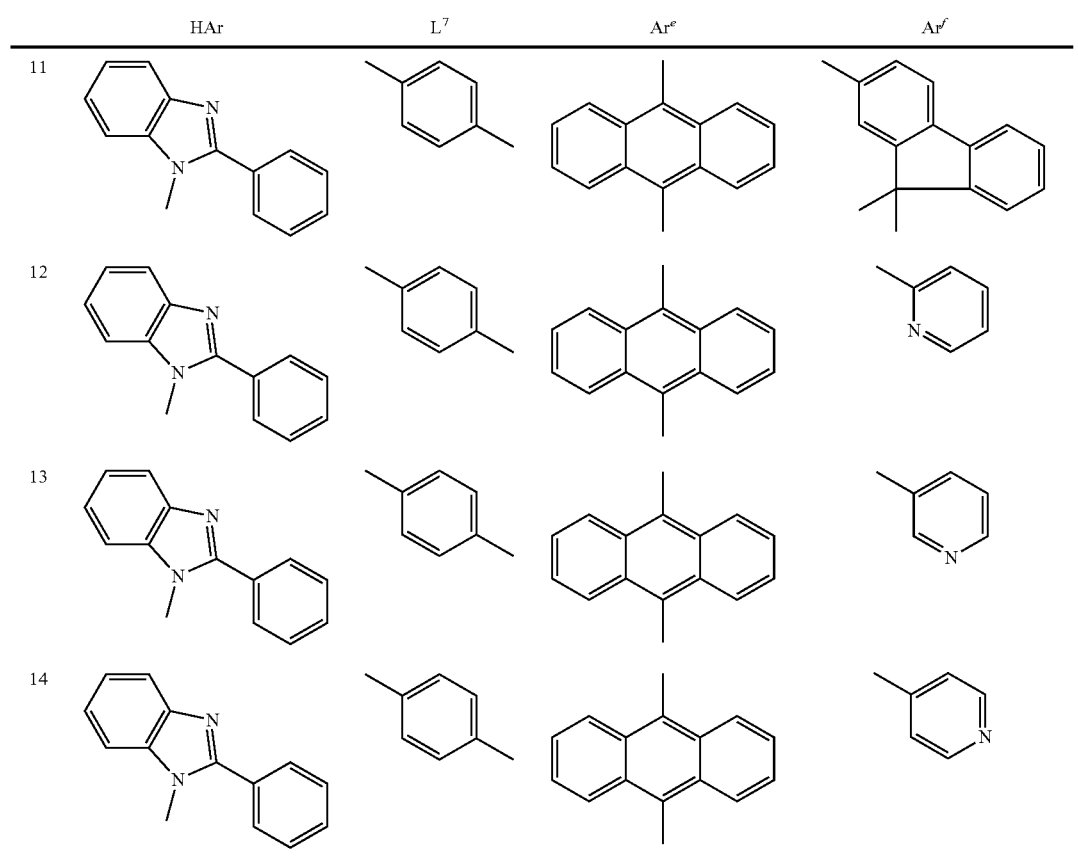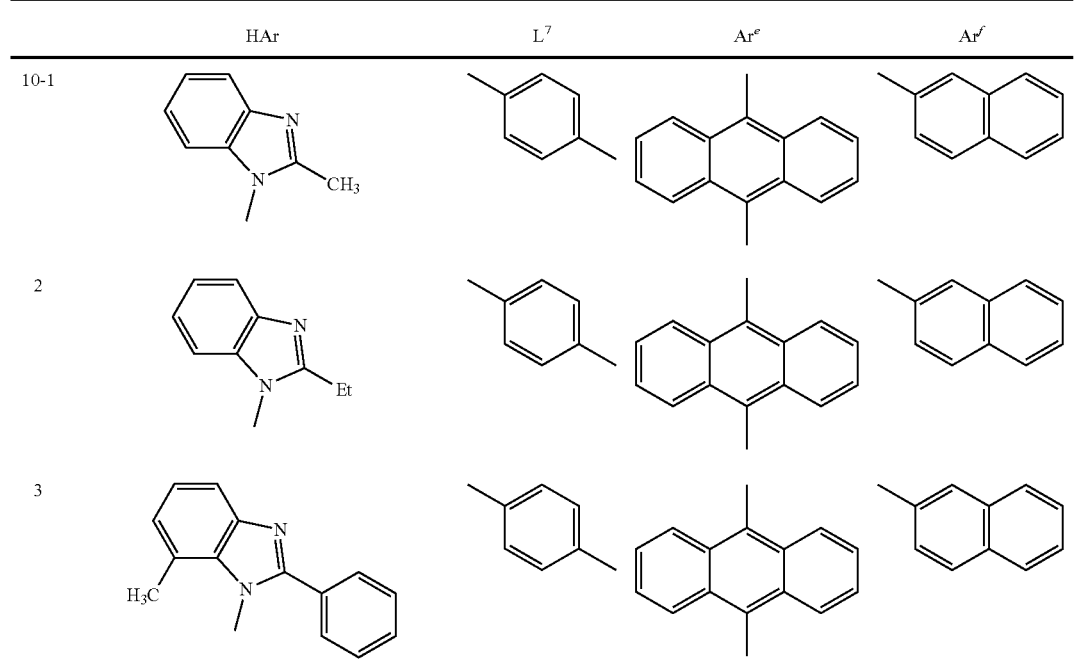

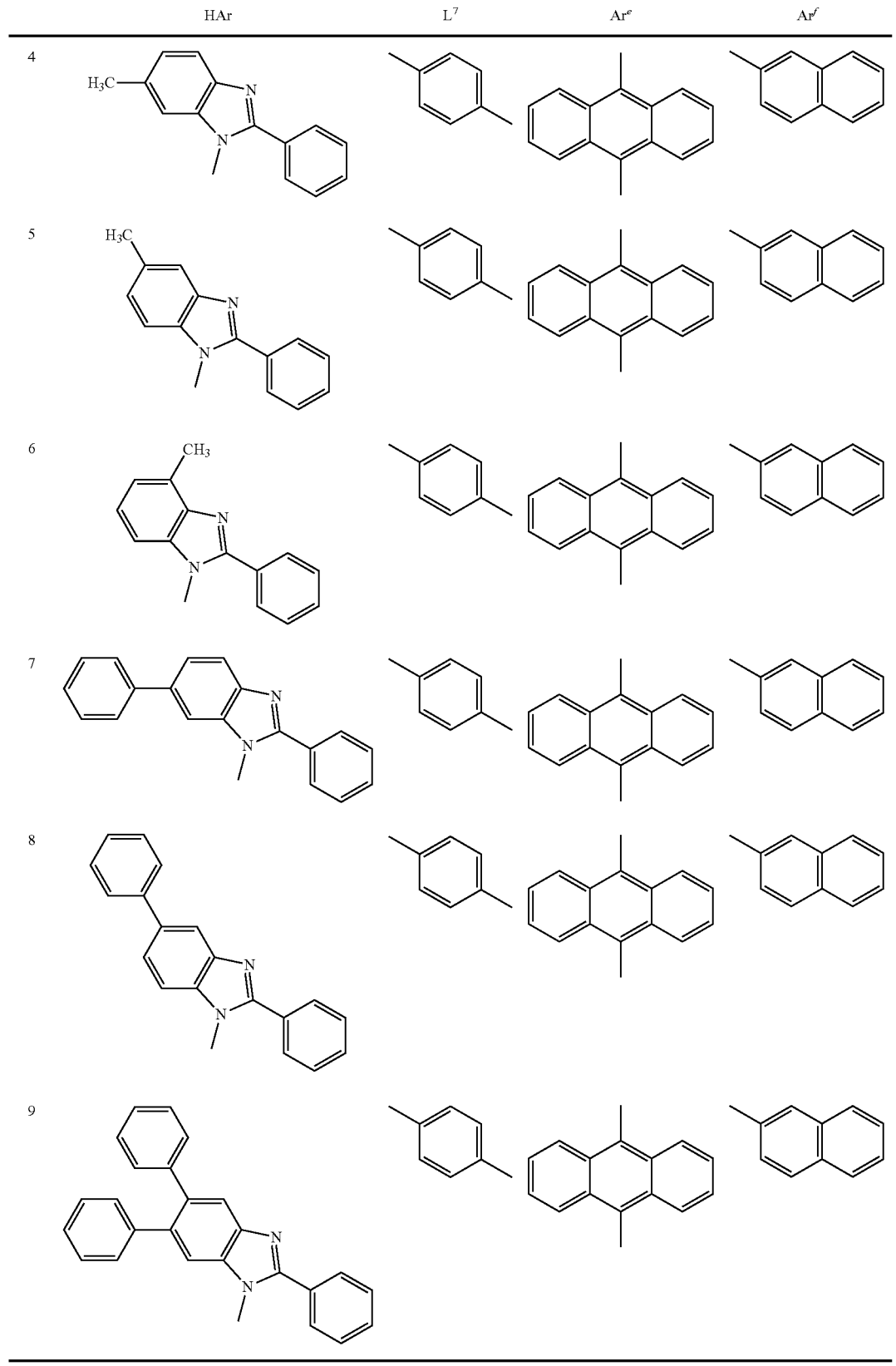

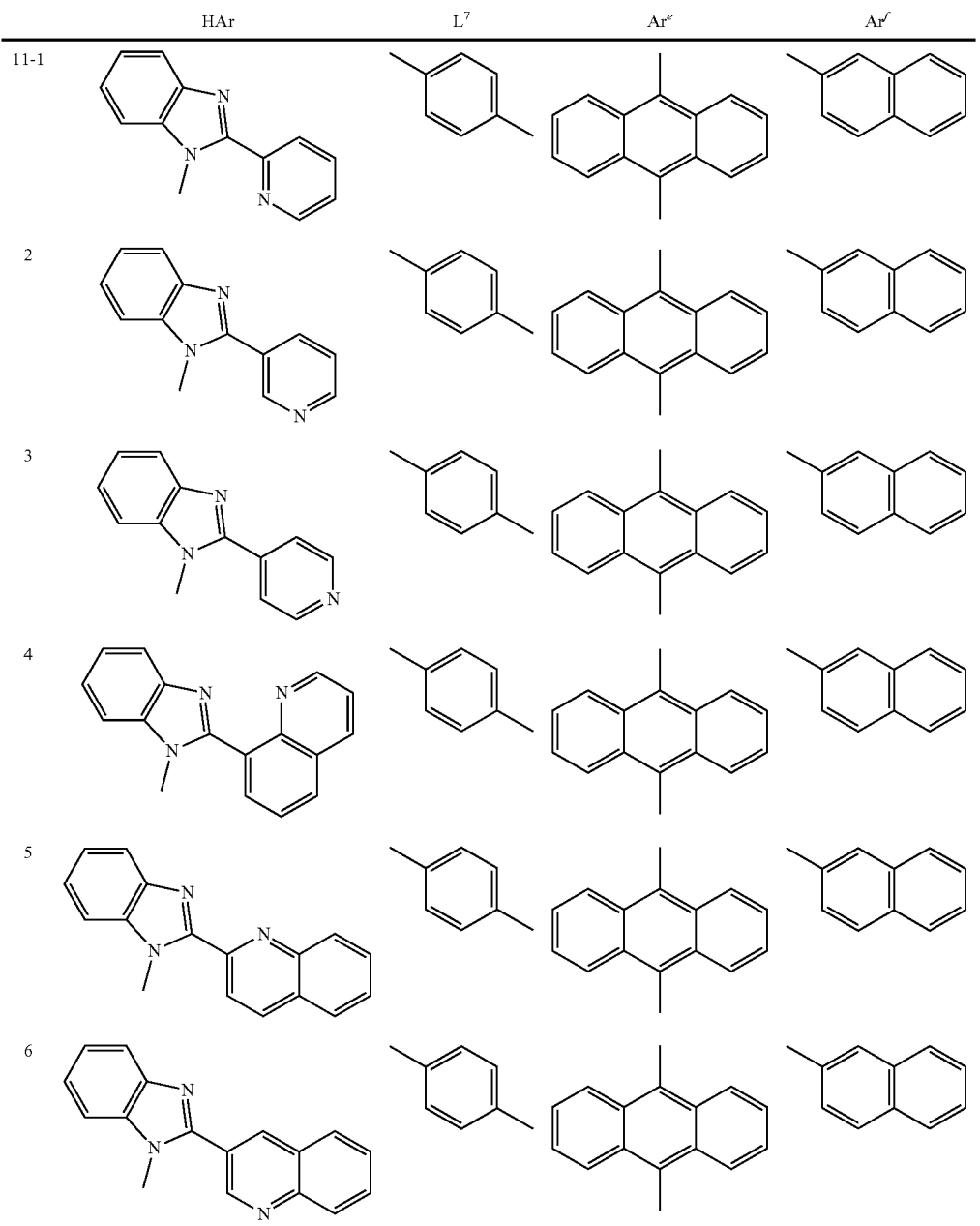
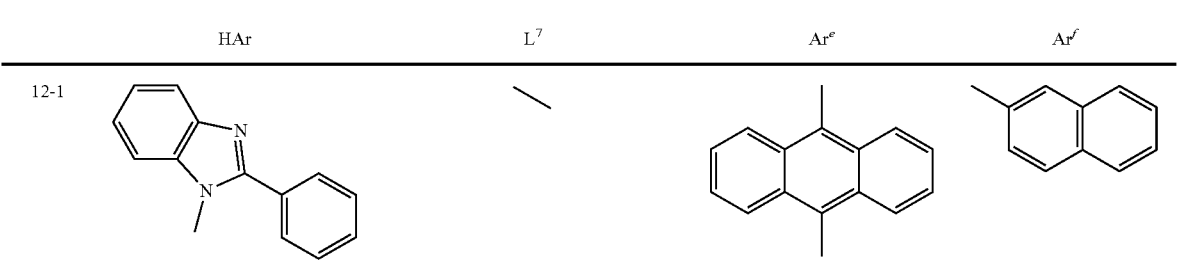

-continued

| | HAr | L⁷ | Arᵉ | Arᶠ |
|---|---|---|---|---|
| 2 | 1-methyl-2-phenyl-benzimidazole | 1,3-phenylene | 9,10-anthracenediyl | 2-naphthyl |
| 3 | 1-methyl-2-phenyl-benzimidazole | 1,2-phenylene | 9,10-anthracenediyl | 2-naphthyl |
| 4 | 1-methyl-2-phenyl-benzimidazole | 2,5-pyridinediyl | 9,10-anthracenediyl | 2-naphthyl |
| 5 | 1-methyl-2-phenyl-benzimidazole | 2,6-pyridinediyl | 9,10-anthracenediyl | 2-naphthyl |
| 6 | 1-methyl-2-phenyl-benzimidazole | 4,4'-biphenylene | 9,10-anthracenediyl | 2-naphthyl |
| 7 | 1-methyl-2-phenyl-benzimidazole | 3,4'-biphenylene | 9,10-anthracenediyl | 2-naphthyl |
| 8 | 1-methyl-2-phenyl-benzimidazole | 3,3'-biphenylene | 9,10-anthracenediyl | 2-naphthyl |
| 9 | 1-methyl-2-phenyl-benzimidazole | 1,4-naphthalenediyl | 9,10-anthracenediyl | 2-naphthyl |

-continued
| | HAr | L⁷ | Arᵉ | Arᶠ |
|---|---|---|---|---|
| 10 | 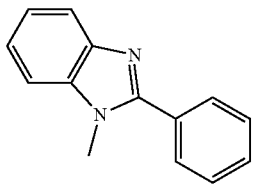 | 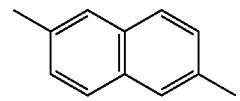 | 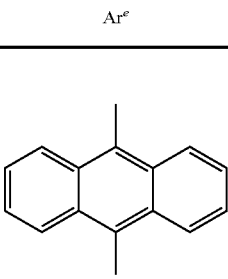 | 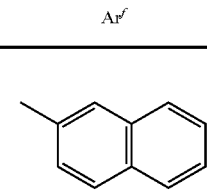 |
| 11 | 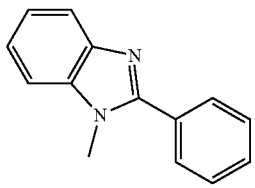 | 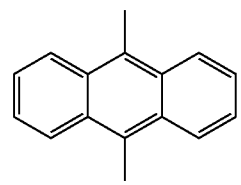 | 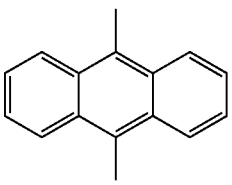 | 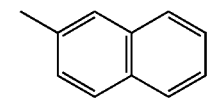 |
| | HAr | L⁷ | Arᵉ | Arᶠ |
|---|---|---|---|---|
| 13-1 | 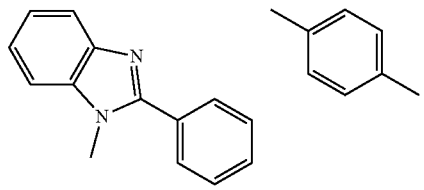 | | 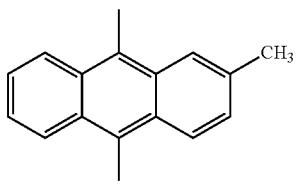 | 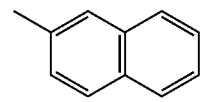 |
| 2 | 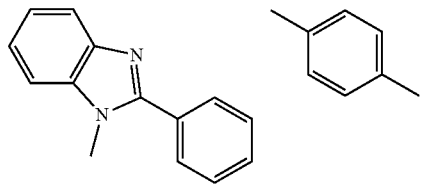 | | 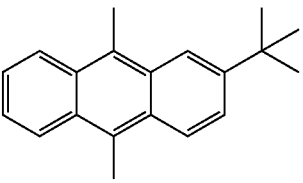 | 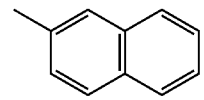 |
| 3 | 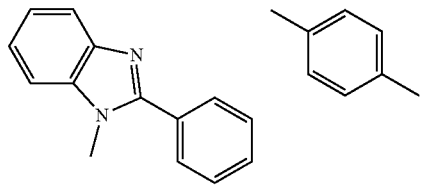 | | 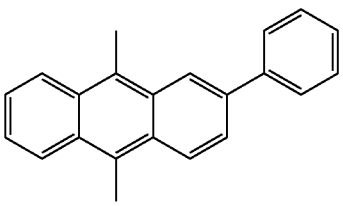 | 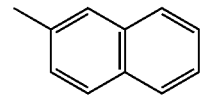 |
| 4 | 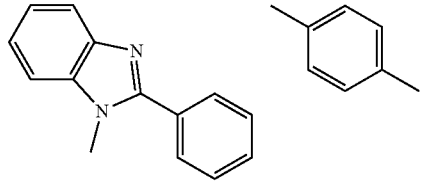 | | 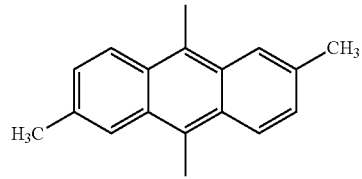 | 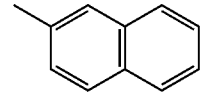 |

-continued
| | HAr—L⁷—Arᵉ—Arᶠ | | | |
|---|---|---|---|---|
| | HAr | L⁷ | Arᵉ | Arᶠ |
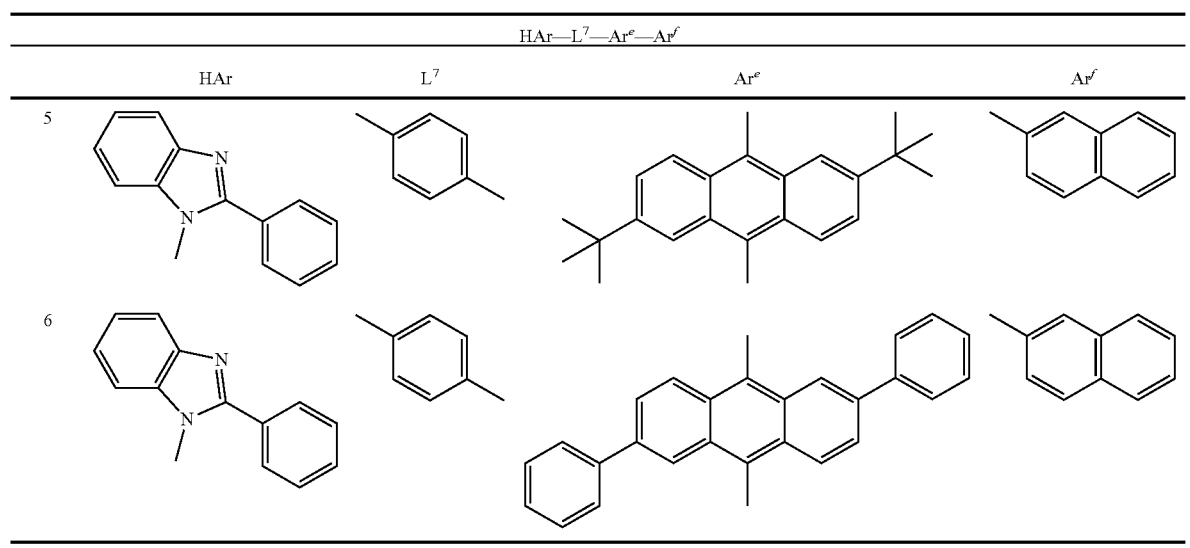
| | HAr—L⁷—Arᵉ—Arᶠ | | | |
|---|---|---|---|---|
| | HAr | L⁷ | Arᵉ | Arᶠ |
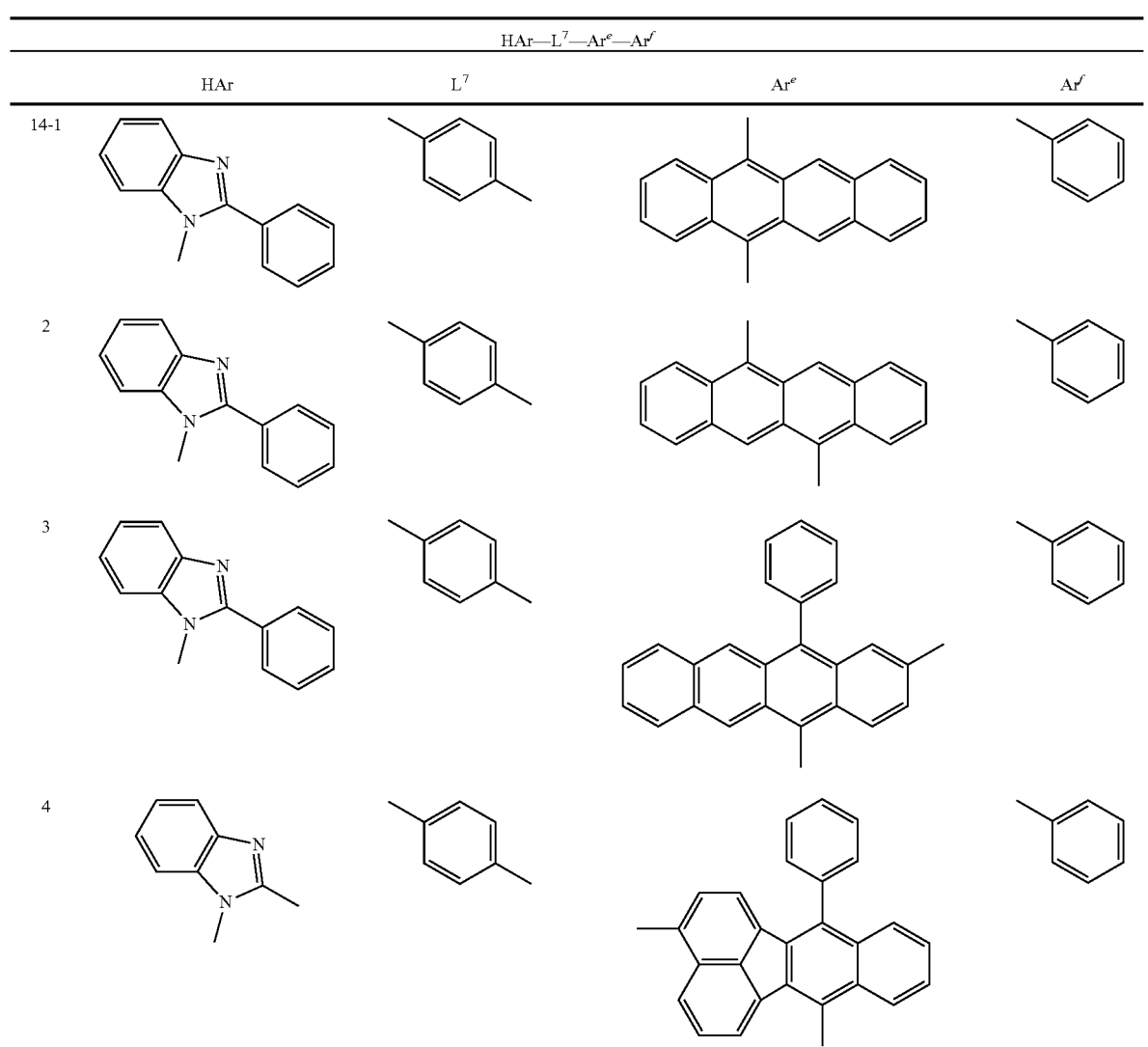

-continued
| HAr—L⁷—Arᵉ—Arᶠ | | | |
|---|---|---|---|
| HAr | L⁷ | Arᵉ | Arᶠ |
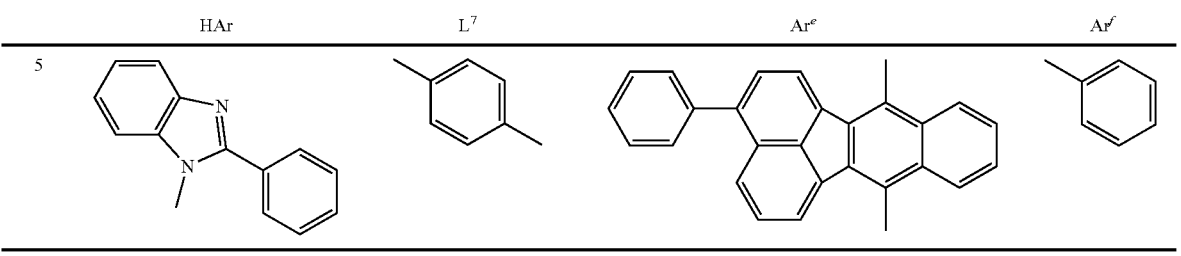
| HAr—L⁷—Arᵉ—Arᶠ | | | |
|---|---|---|---|
| HAr | L⁷ | Arᵉ | Arᶠ |
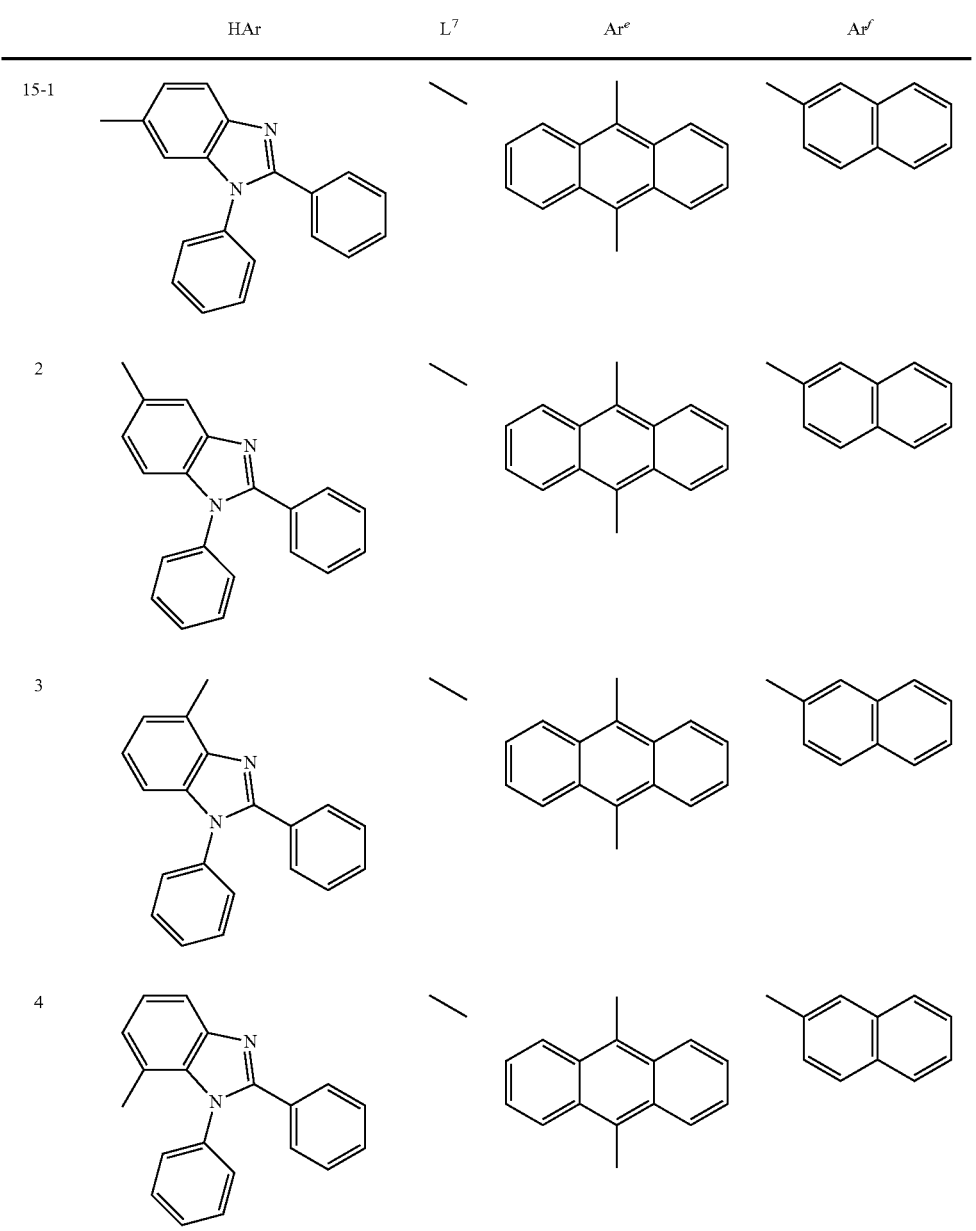

-continued
| | HAr | L7 | Are | Arf |
|---|---|---|---|---|
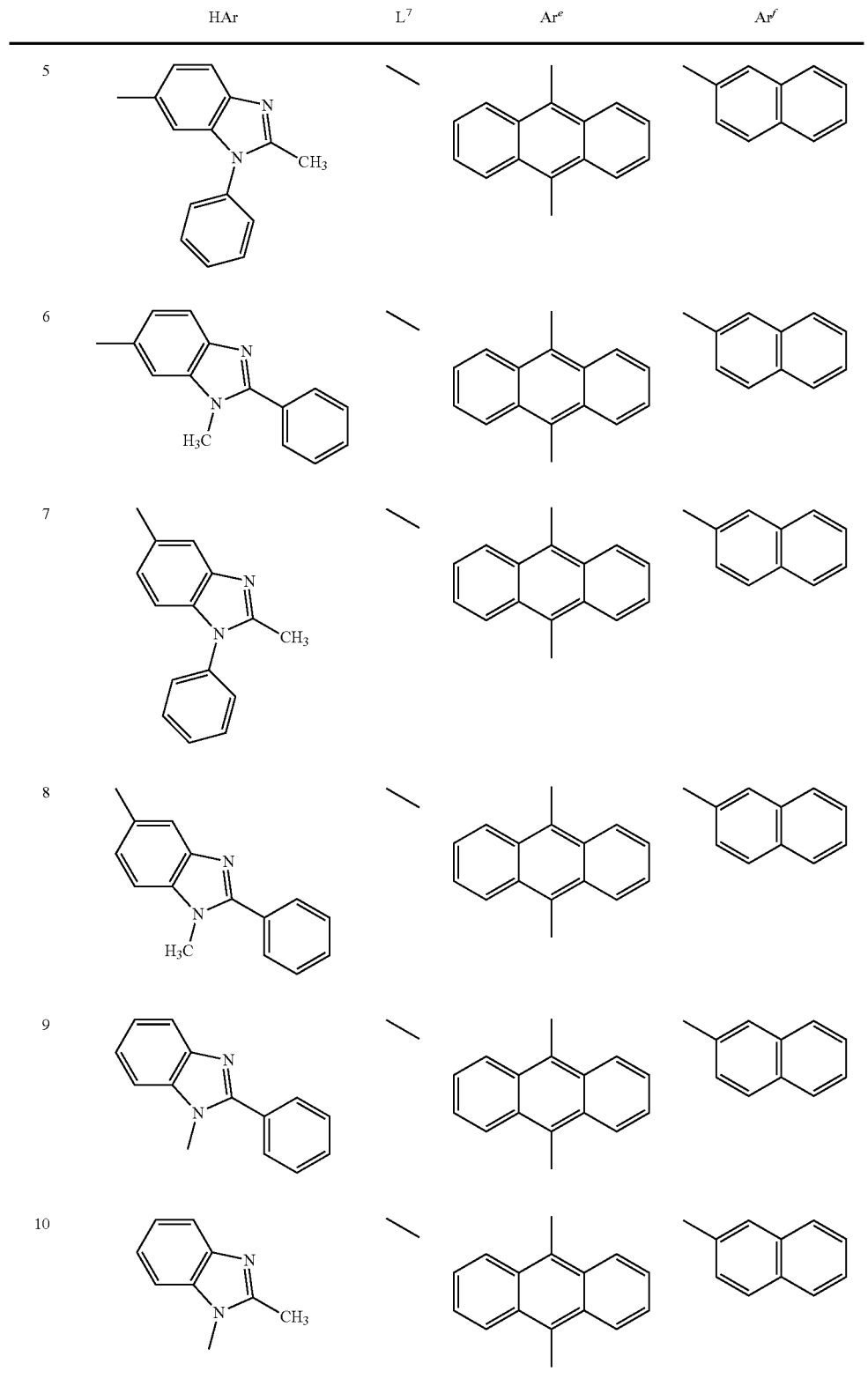

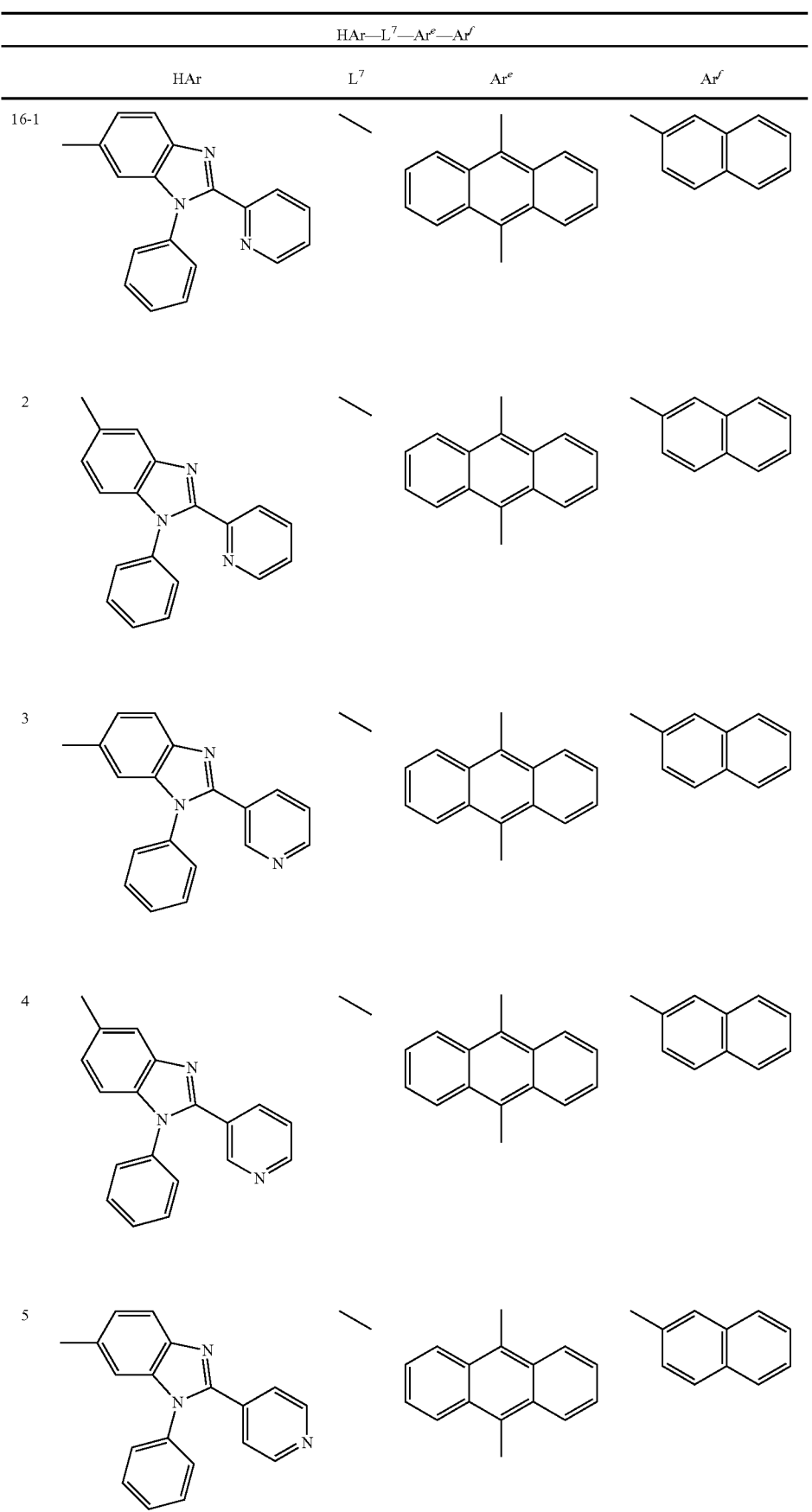

-continued
| HAr—L⁷—Arᵉ—Arᶠ |||||
|---|---|---|---|---|
| | HAr | L⁷ | Arᵉ | Arᶠ |
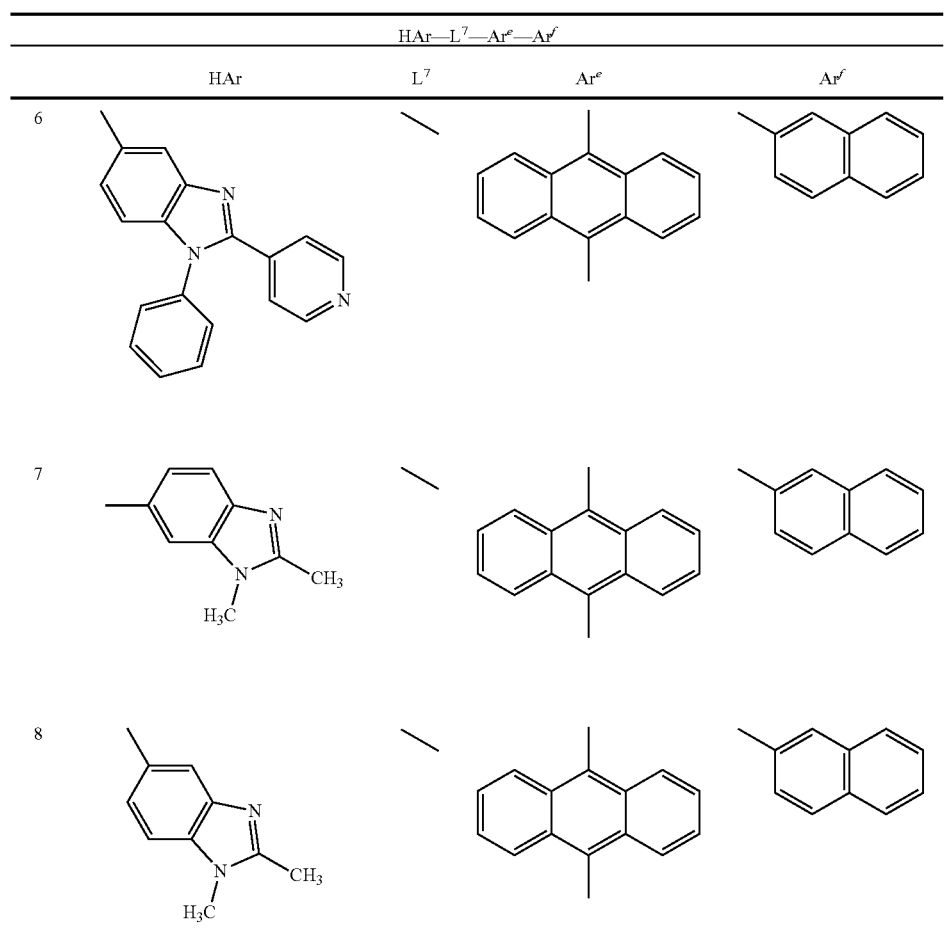
| HAr—L⁷—Arᵉ—Arᶠ |||||
|---|---|---|---|---|
| | HAr | L⁷ | Arᵉ | Arᶠ |
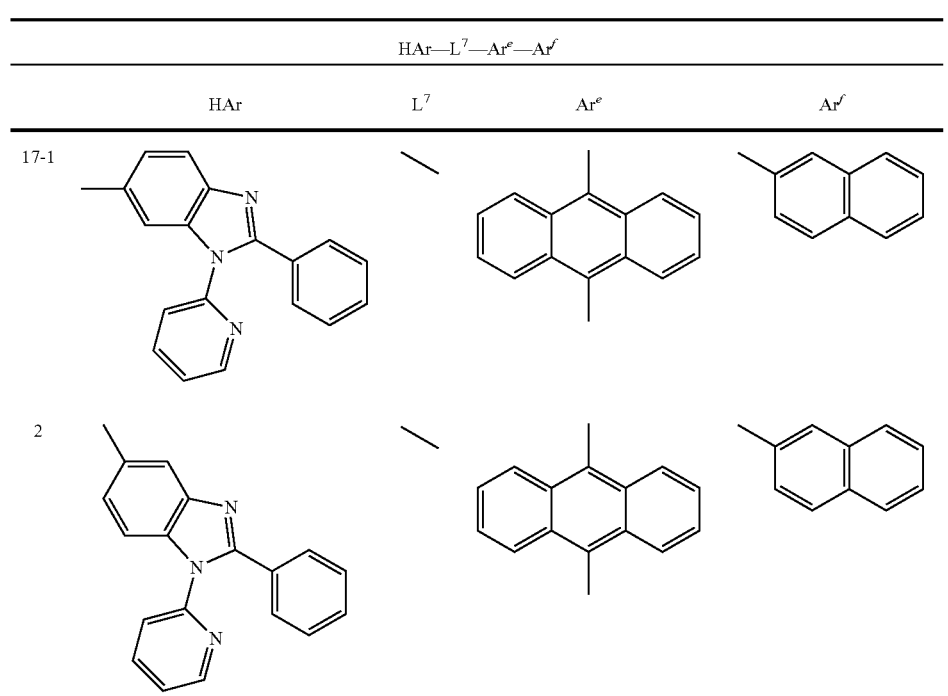

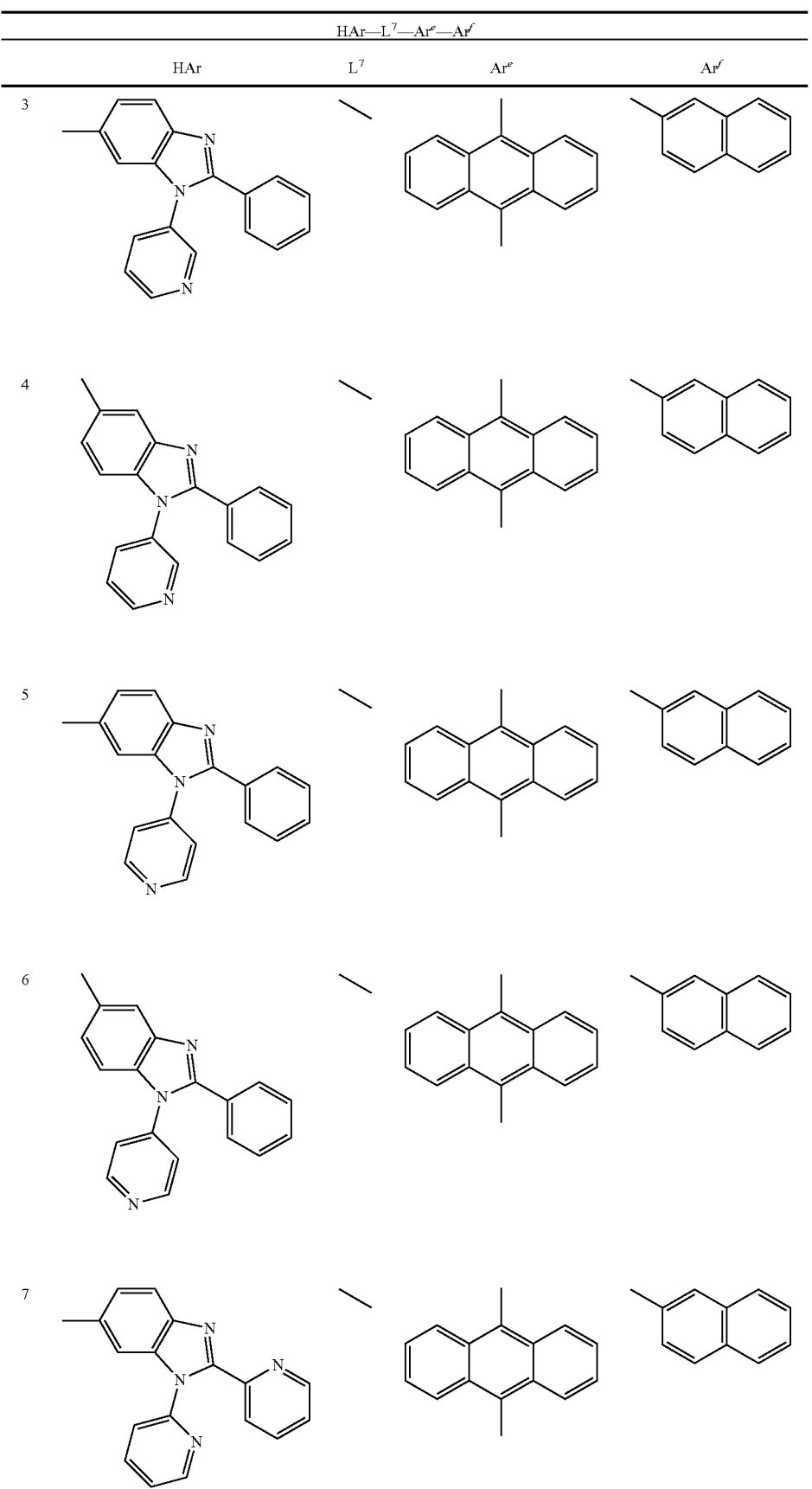

| HAr—L⁷—Arᵉ—Arᶠ | | | |
|---|---|---|---|
| HAr | L⁷ | Arᵉ | Arᶠ |
| 8 | 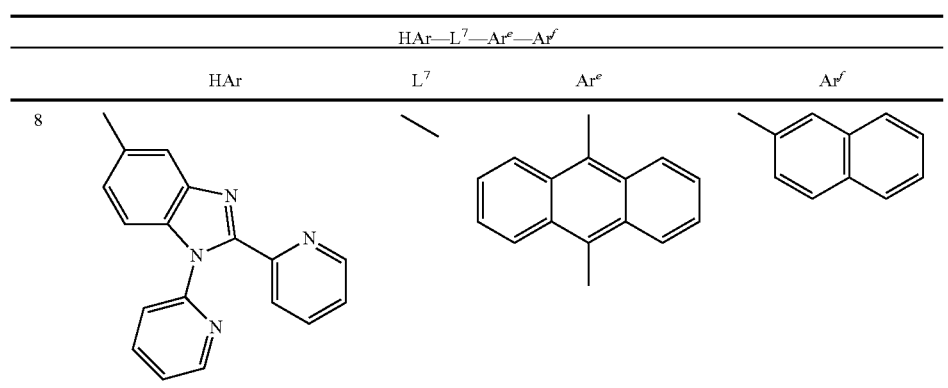 | | |

Among the above specific examples, (1-1), (1-5), (1-7), (2-1), (3-1), (4-2), (4-6), (7-2), (7-7), (7-8), (7-9), (9-1) and (9-7) are particularly preferred.

Further, the nitrogen-containing heterocyclic derivative preferably includes as well nitrogen-containing five-membered ring derivatives. The above five-membered ring includes, for example, an imidazole ring, a triazole ring, a tetrazole ring, an oxazole ring, a thiadiazole ring, an oxatriazole ring, a thiatriazole ring and the like, and the nitrogen-containing five-membered ring derivative includes a benzimidazole ring, a benzotriazole ring, a pyridinoimidazole ring, a pyrimidinoimidazole ring and a pyridazinoimidazole ring. Derivatives represented by the following Formula (B) are particularly preferred.

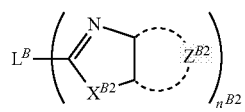
(B)

In Formula (B), $L^B$ represents a divalent or more linkage group and includes, for example, a carbon atom, a silicon atom, a nitrogen atom, a boron atom, an oxygen atom, a sulfur atom, a metal atom (for example, a barium atom, a beryllium atom), an aromatic hydrocarbon ring, an aromatic heterocycle and the like. Among them, a carbon atom, a nitrogen atom, a silicon atom, a boron atom, an oxygen atom, a sulfur atom, an aromatic hydrocarbon ring and an aromatic heterocycle are preferred, and a carbon atom, a silicon atom, an aromatic hydrocarbon ring and an aromatic heterocycle are more preferred.

The aromatic hydrocarbon rings and the aromatic heterocycles represented by $L^B$ may have substituents, and the above substituents are preferably an alkyl group, an alkenyl group, an alkynyl group, an aryl group, an amino group, an alkoxy group, an aryloxy group, an acyl group, an alkoxycarbonyl group, an aryloxycarbonyl group, an acylxoy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group and an aromatic heterocycle, more preferably an alkyl group, an aryl group, an alkoxy group, an aryloxy group, a halogen atom, a cyano group and an aromatic heterocycle, further preferably an alkyl group, an aryl group, an alkoxy group, an aryloxy group and an aromatic heterocycle and particularly preferably an alkyl group, an aryl group, an alkoxy group and an aromatic heterocycle.

The specific examples of $L^B$ include groups shown below:

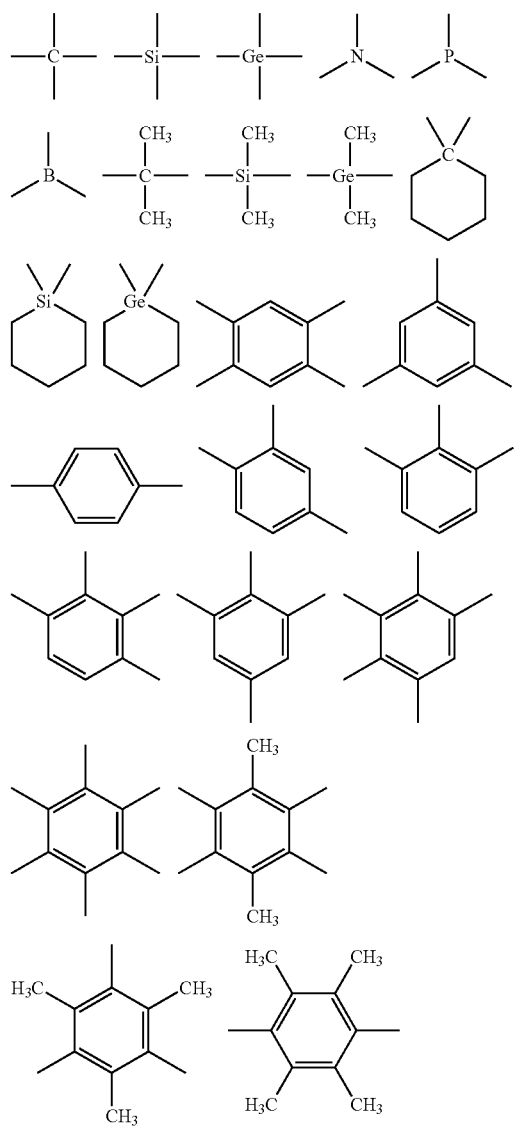

-continued

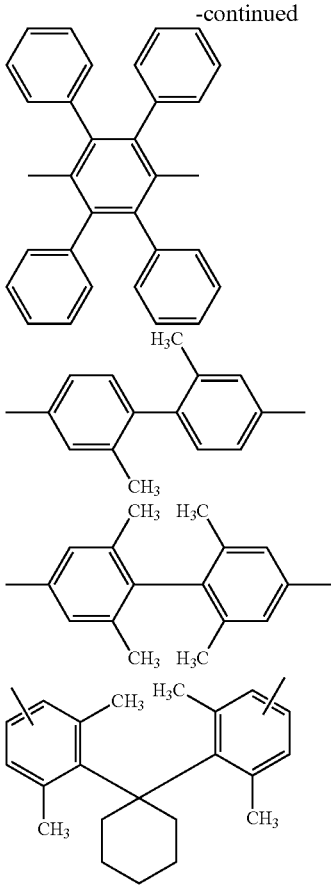

$X^{B2}$ in Formula (B) represents —O—, —S— or —N($R^{B2}$)—. $R^{B2}$ represents a hydrogen atom, an aliphatic hydrocarbon group, an aryl group or a heterocyclic group.

The aliphatic hydrocarbon group represented by $R^{B2}$ is a linear or branched alkyl group (it is an alkyl group having preferably 1 to 20 carbon atoms, more preferably 1 to 12 carbon atoms and particularly preferably 1 to 8 carbon atoms and includes, for example, methyl, ethyl, isopropyl, t-butyl, n-octyl, n-decyl, n-hexadecyl and the like), a cycloalkyl group (it has preferably 3 to 10 ring carbon atoms and includes, for example, cyclopropyl, cyclopentyl, cyclohexyl and the like), an alkenyl group (it is an alkenyl group having preferably 2 to 20 carbon atoms, more preferably 2 to 12 carbon atoms and particularly preferably 2 to 8 carbon atoms and includes, for example, vinyl, allyl, 2-butenyl, 3-pentenyl and the like) and an alkynyl group (it is an alkynyl group having preferably 2 to 20 carbon atoms, more preferably 2 to 12 carbon atoms and particularly preferably 2 to 8 carbon atoms and includes, for example, propargyl, 3-pentynyl and the like), and alkyl groups are preferred.

The aryl group represented by $R^{B2}$ is a single ring or a condensed ring, and it is preferably an aryl group having preferably 6 to 30 ring carbon atoms, more preferably 6 to 20 ring carbon atoms and further preferably 6 to 12 ring carbon atoms. It includes, for example, phenyl, 2-methylphenyl, 3-methylphenyl, 4-methylphenyl, 2-methoxyphenyl, 3-trifluoromethylphenyl, pentafluorophenyl, 1-naphthyl, 2-naphthyl and the like, and phenyl and 2-methylphenyl are preferred.

The heterocyclic group represented by $R^{B2}$ is a single ring or a condensed ring, and it is preferably a heterocyclic group having preferably 1 to 20 ring carbon atoms, more preferably 1 to 12 ring carbon atoms and further preferably 2 to 10 ring carbon atoms and is an aromatic heterocyclic group containing at least one hetero atom of a nitrogen atom, an oxygen atom, a sulfur atom and a selenium atom. The examples of the above heterocyclic group include, for example, groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzomidazole, benzoxazole, benzothiazole, benzotriazole, tetrazaindene, carbazole, azepine and the like, and they are preferably groups derived from furan, thiophene, pyridine, pyrazine, pyrimidine, pyridazine, triazine, quinoline, phthalazine, naphthyridine, quinoxaline and quinazoline, more preferably groups derived from furan, thiophene, pyridine and quinoline. It is further preferably quinolinyl.

The aliphatic hydrocarbon group, the aryl group and the heterocyclic group each represented by $R^{B2}$ may have substituents, and the above substituents are preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group and an aromatic heterocycle, more preferably an alkyl group, an aryl group, an alkoxy group, an aryloxy group, a halogen atom, a cyano group and an aromatic heterocycle, further preferably an alkyl group, an aryl group, an alkoxy group, an aryloxy group and an aromatic heterocycle and particularly preferably an alkyl group, an aryl group, an alkoxy group and an aromatic heterocycle.

$R^{B2}$ is preferably an aliphatic hydrocarbon group, an aryl group or a heterocyclic group, more preferably an aliphatic hydrocarbon group (the group having preferably 6 to 30 carbon atoms, more preferably 6 to 20 carbon atoms and further preferably 6 to 12 carbon atoms) or an aryl group and further preferably an aliphatic hydrocarbon group (the group having preferably 1 to 20 carbon atoms, more preferably 1 to 12 carbon atoms and further preferably 2 to 10 carbon atoms).

$X^{B2}$ is preferably —O— or —N($R^{B2}$)—, more preferably —N($R^{B2}$)—.

$Z^{B2}$ represents an atomic group necessary for forming an aromatic ring. The aromatic ring formed by $Z^{B2}$ may be any of an aromatic hydrocarbon ring and an aromatic heterocycle, and the specific examples thereof include, for example, a benzene ring, a pyridine, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tetrazole ring, a thiadiazole ring, an oxadiazole ring, a pyrazole ring and the like, and they are preferably a benzene ring, a pyridine, a pyrazine ring, a pyrimidine ring and a pyridazine ring, more preferably a benzene ring, a pyridine ring and a pyrazine ring, further preferably a benzene ring and a pyridine ring and particularly preferably a pyridine ring.

The aromatic ring formed by $Z^{B2}$ may further form condensed rings with other rings and may have a substituent. The substituents are the same as the groups listed as the substituents of the groups represented by $L^B$ described above, and they are preferably an alkyl group, an alkenyl group, an alkynyl group, an aryl group, an amino group, an alkoxy group, an aryloxy group, an acyl group, an alkoxycarbonyl group, an aryloxycarbonyl group, an acylxoy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group and an aromatic heterocycle, more preferably an alkyl group, an aryl group, an alkoxy group, an aryloxy group, a halogen atom, a cyano group and an aromatic heterocycle, further preferably an alkyl group, an aryl group, an alkoxy group, an aryloxy group and an aromatic heterocycle and particularly preferably an alkyl group, an aryl group, an alkoxy group and an aromatic heterocycle.

The term $n^{B2}$ is an integer of 1 to 4, preferably 2 to 3.

Among the nitrogen-containing five-membered ring derivatives represented by Formula (B) described above, derivatives represented by Formula (B') shown below are more preferred:

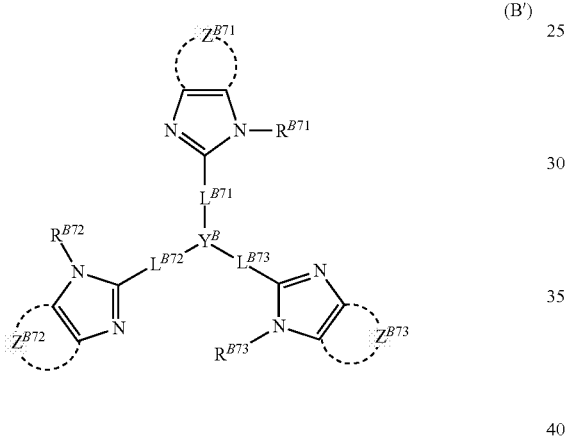

(B')

In Formula (B'), $R^{B71}$, $R^{B72}$ and $R^{B73}$ each are the same as $R^{B2}$ in Formula (B), and the preferred ranges are the same as well.

$Z^{B71}$, $Z^{B72}$, and $Z^{B73}$ each are the same as $Z^{B2}$ in Formula (B), and the preferred ranges are the same as well.

$L^{B71}$, $L^{B72}$, and $L^{B73}$ each represent a linkage group and include groups obtained by turning the examples of $L^B$ in Formula (B) into divalent groups, and they are preferably linkage groups comprising a single bond, a divalent aromatic hydrocarbon ring group, a divalent aromatic heterocyclic group and combinations thereof, more preferably single bonds. $L^{B71}$, $L^{B72}$ and $L^{B73}$ may have substituents. The above substituents are the same as the groups listed as the substituents of the groups represented by $L^B$ in Formula (B) described above, and the preferred substituents are the same as well.

$Y^B$ represents a nitrogen atom, a 1,3,5-benzenetoluoyl group or a 2,4,6-triazinetoluoyl group. The 1,3,5-benzenetoluoyl group may have substituents at 2, 4 and 6-positions, and the substituents include, for example, an alkyl group, an aromatic hydrocarbon ring group, a halogen atom and the like.

The specific examples of the nitrogen-containing five-membered ring derivative represented by Formula (B) or Formula (B') shall be shown below, but they shall not be restricted to these compounds shown as the examples:

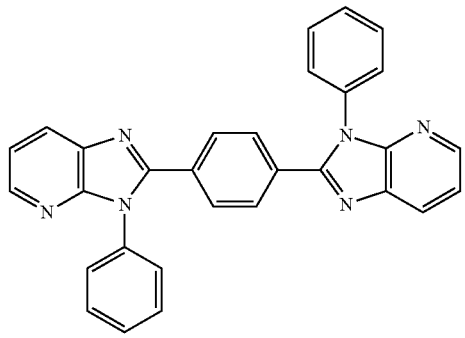

(B-1)

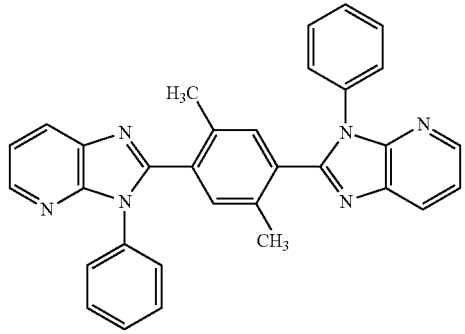

(B-2)

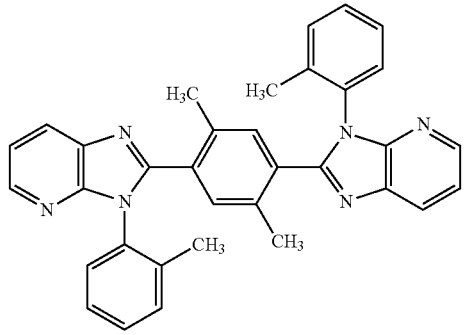

(B-3)

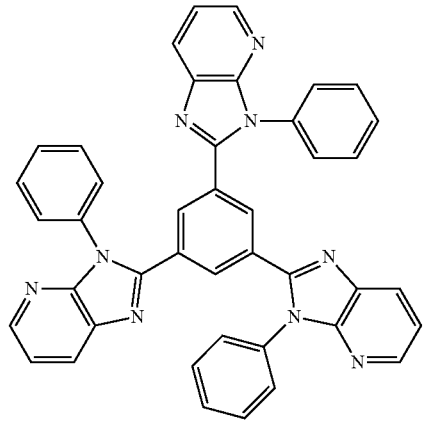

(B-4)

(B-5) 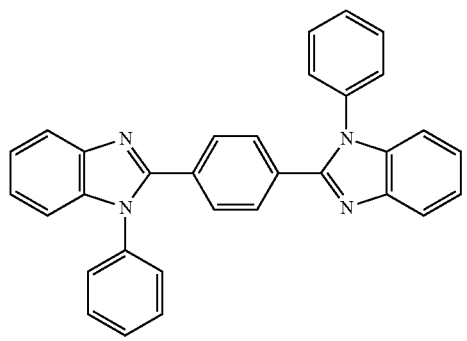
(B-6) 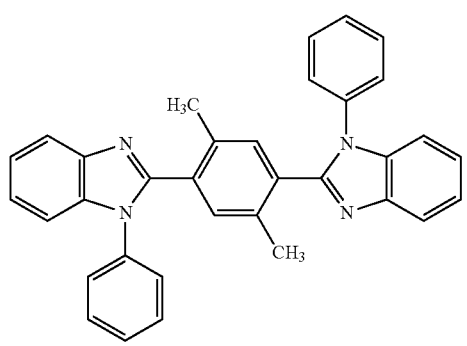
(B-7) 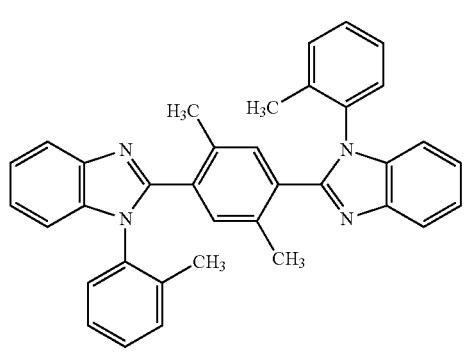
(B-8) 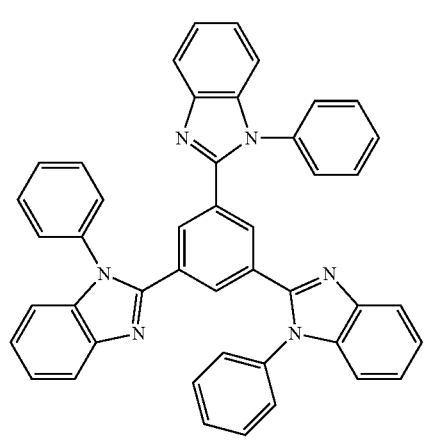
(B-9) 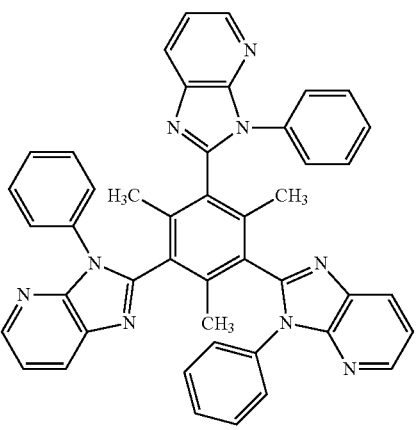
(B-10) 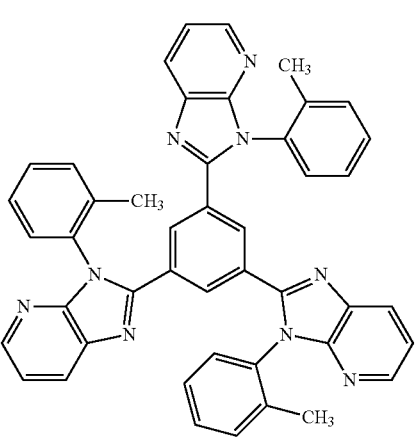
(B-11) 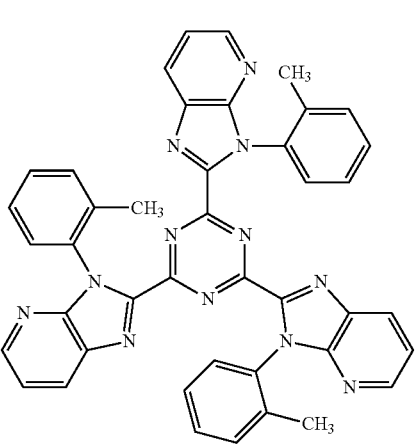

(B-12)

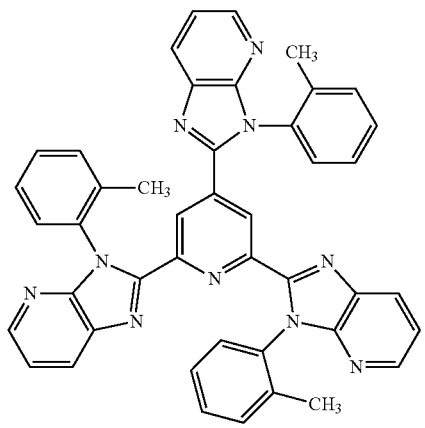

(B-13)

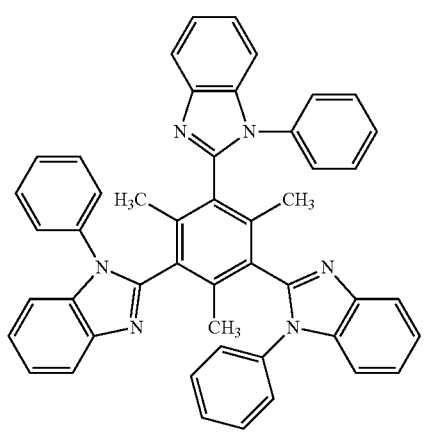

(B-14)

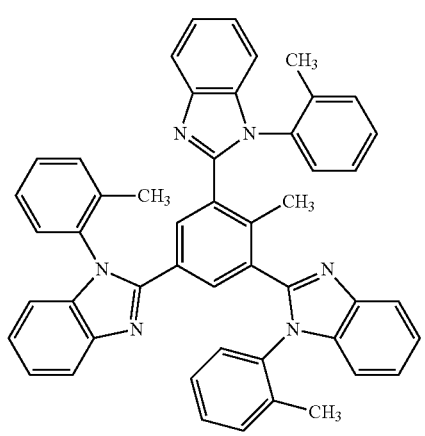

(B-15)

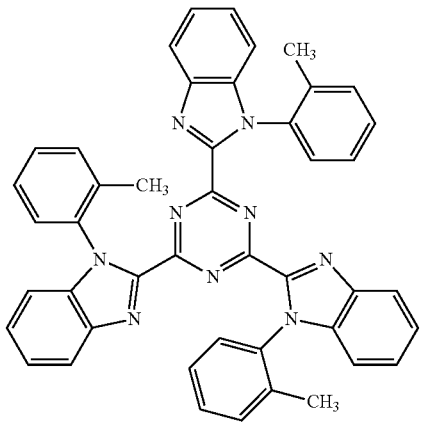

(B-16)

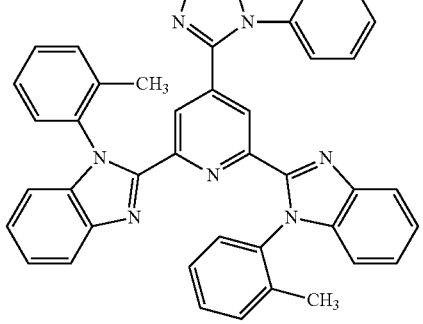

The compounds constituting the electron injecting layer and the electron transporting layer include as well compounds having a structure in which an electron deficient nitrogen-containing five-membered ring or an electron deficient nitrogen-containing six-membered ring skeleton is combined with a substituted or non-substituted indole skeleton, a substituted or non-substituted carbazole skeleton and a substituted or non-substituted azacarbazole skeleton. Also, the suitable electron deficient nitrogen-containing five-membered ring or electron deficient nitrogen-containing six-membered ring skeleton includes, for example, pyridine, pyrimidine, pyrazine, triazine, triazole, oxadiazole, pyrazole, imidazole, quinoxaline and pyrrole skeletons and molecular skeletons such as benzimidazole, imidazopyridine and the like each obtained by combining the above skeletons with each other. Among the above combinations, they include preferably combinations of pyridine, pyrimidine, pyrazine and triazine skeletons with carbazole, indole, azacarbazole and quinoxaline skeletons. The skeletons described above may be either substituted or non-substituted.

The specific examples of the electron transporting compound shall be shown below but shall not be restricted to these compounds:

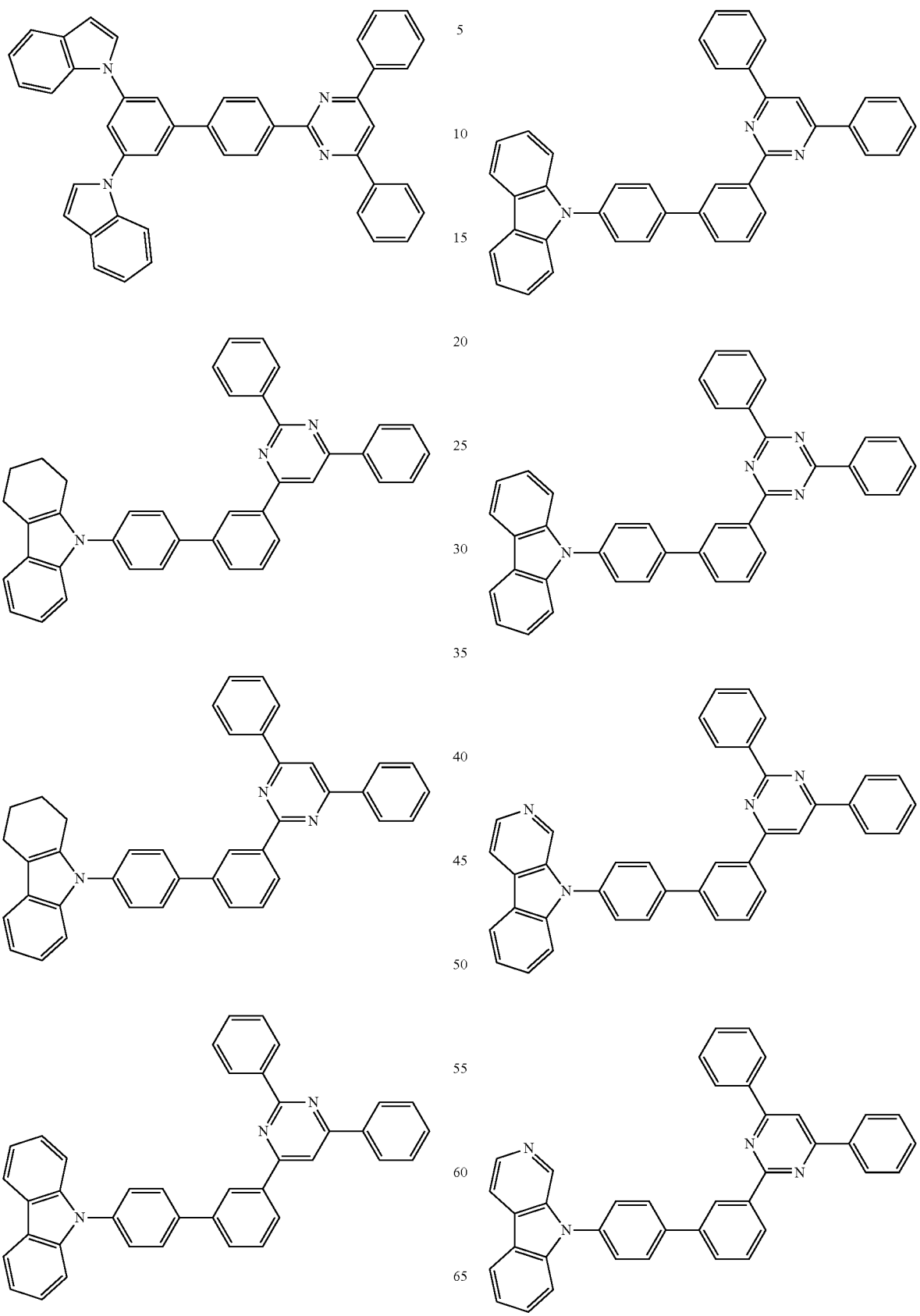

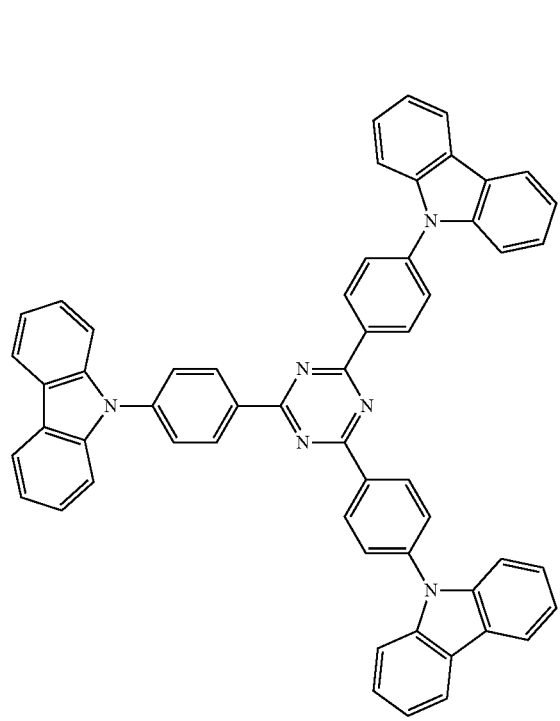
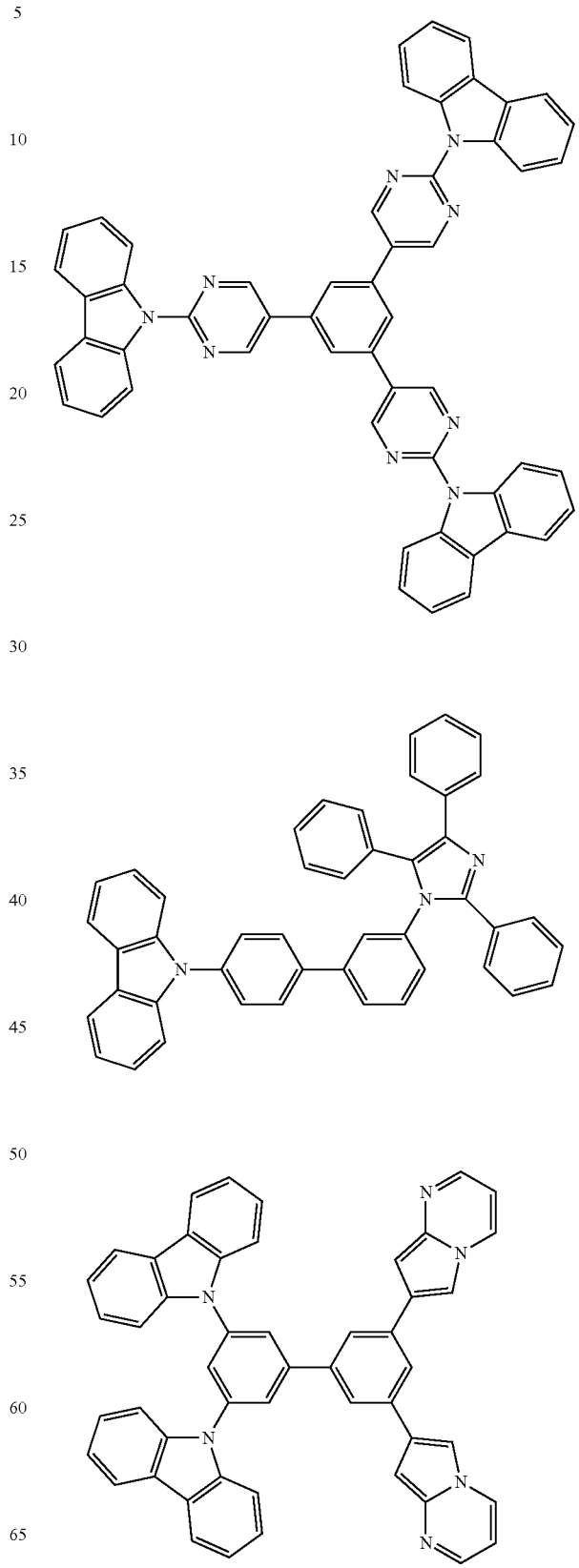

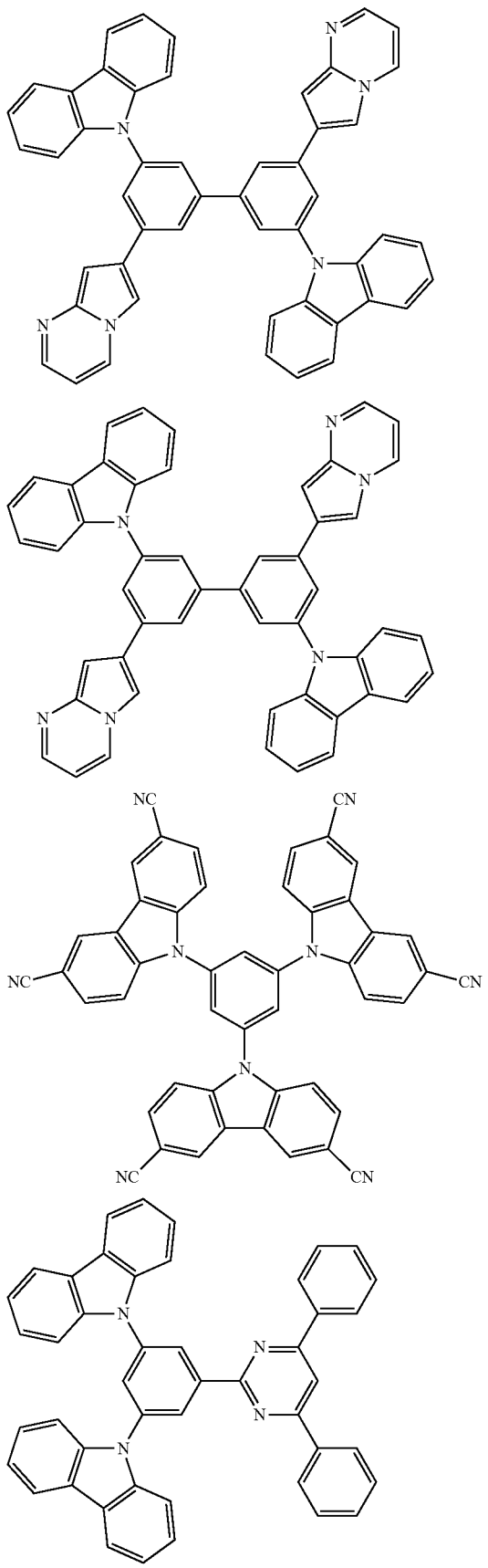

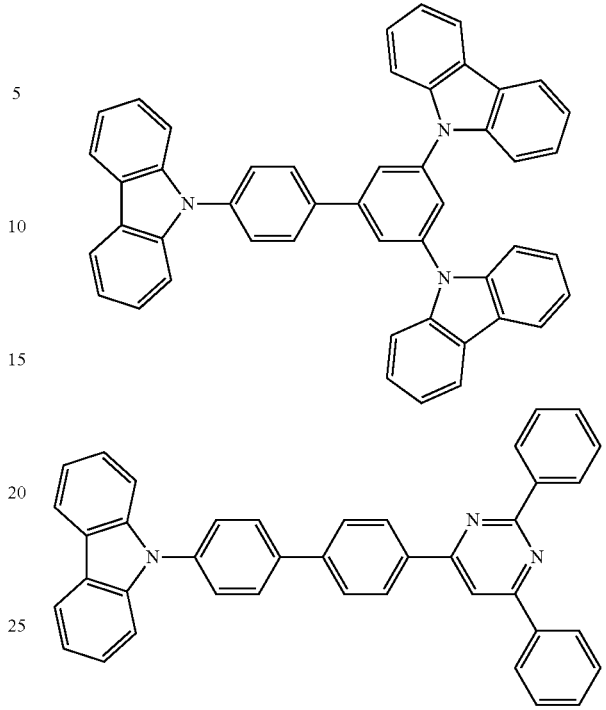

The electron injecting layer and the electron transporting layer may have either a single layer structure comprising at least one of the materials described above or a multilayer structure comprising plural layers having the same composition or different compositions. The materials of the above layers have preferably a π electron deficient nitrogen-containing heterocyclic group.

Further, an insulator or a semiconductor in addition to the nitrogen-containing ring derivative is preferably used as a constituent for the electron injecting layer. If the electron injecting layer is constituted from an insulator and a semiconductor, an electric current can effectively be prevented from leaking to enhance the electron injecting property.

Preferably used as the above insulator is at least one metal compound selected from the group consisting of alkali metal chalcogenides, alkaline earth metal chalcogenides, halides of alkali metals and halides of alkaline earth metals. If the electron injecting layer is constituted from the above alkali metal chalcogenides and the like, it is preferred in terms of making it possible to enhance further the electron injecting property. To be specific, the preferred alkali metal chalcogenides include, for example, $Li_2O$, $K_2O$, $Na_2S$, $Na_2Se$ and $Na_2O$, and the preferred alkaline earth metal chalcogenides include, for example, CaO, BaO, SrO, BeO, BaS and CaSe. Further, the preferred halides of alkali metals include, for example, LiF, NaF, KF, LiCl, KCl, NaCl and the like. Also, the preferred halides of alkaline earth metals include, for example, fluorides such as $CaF_2$, $BaF_2$, $SrF_2$, $Mg_2$, $BeF_2$ and the like and halides other than the fluorides.

The semiconductor includes, for example, oxides, nitrides and oxynitrides each containing at least one element selected from the group consisting of Ba, Ca, Sr, Yb, Al, Ga, In, Li, Na, Cd, Mg, Si, Ta, Sb and Zn, and they may be used alone or in combination of two or more kinds thereof. Also, the inorganic compound constituting the electron injecting layer is preferably a fine crystalline or amorphous insulating thin film. If the electron injecting layer is constituted from the above insulating thin film, the more homogeneous thin film is formed, and therefore pixel defects such as dark spots and the like can be reduced. The above inorganic compound includes, for example, alkali metal chalcogenides, alkaline earth metal chalcogenides, halides of alkali metals and halides of alkaline earth metals.

Further, the reducing dopant described above can preferably be added to the electron injecting layer in the present invention.

A film thickness of the electron injecting layer or the electron transporting layer shall not specifically be restricted, and it is preferably 1 to 100 nm.

An aromatic amine compound, for example, an aromatic amine derivative represented by Formula (I) is suitably used in the hole injecting layer or the hole transporting layer (including the hole injecting transporting layer):

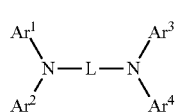
(I)

In Formula (I), $Ar^1$ to $Ar^4$ represent a substituted or non-substituted aryl group having 6 to 50 ring carbon atoms or a substituted or non-substituted heterocyclic group having 5 to 50 ring atoms.

The substituted or non-substituted aryl group having 6 to 50 ring carbon atoms includes, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl and the like.

The substituted or non-substituted heterocyclic group having 5 to 50 ring atoms includes, for example, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like. It includes preferably phenyl, naphthyl, biphenyl, anthranyl, phenanthryl, pyrenyl, chrysenyl, fluoranthenyl, fluorenyl and the like.

L is a linkage group. To be specific, it is a substituted or non-substituted arylene group having 6 to 50 ring carbon atoms, a substituted or non-substituted heteroarylene group having 5 to 50 ring atoms or a divalent group obtained by combining two or more arylene groups or heteroarylene groups with a single bond, an ether bond, a thioether bond, an alkylene group having 1 to 20 carbon atoms, an alkenylene group having 2 to 20 carbon atoms and an amino group. The arylene group having 6 to 50 ring carbon atoms includes, for example, 1,4-phenylene, 1,2-phenylene, 1,3-phenylene, 1,4-naphthylene, 2,6-naphthylene, 1,5-naphthylene, 9,10-anthranylene, 9,10-phenanthrenylene, 3,6-phenanthrenylene, 1,6-pyrenylene, 2,7-pyrenylene, 6,12-chrysenylene, 4,4'-biphenylene, 3,3'-biphenylene, 2,2'-biphenylene, 2,7-fluorenylene and the like. The heteroarylene group having 5 to 50 ring atoms includes, for example, 2,5-thiophenylene, 2,5-siloylene, 2,5-oxadiazolylene and the like. Preferred are 1,4-phenylene, 1,2-phenylene, 1,3-phenylene, 1,4-naphthylene, 9,10-anthranylene, 6,12-chrysenylene, 4,4'-biphenylene, 3,3'-biphenylene, 2,2'-biphenylene and 2,7-fluorenylene.

When L is a linkage group comprising two or more arylene groups or heteroarylene groups, the adjacent arylene groups or heteroarylene groups may be combined with each other via a divalent group to form a new ring. The examples of the divalent group for forming the ring includes tetramethylene, pentamethylene, hexamethylene, diphenylmethane-2,2'-diyl, diphenylmethane-3,3'-diyl, diphenylpropane-4,4'-diyl and the like.

The substituents of $Ar^1$ to $Ar^4$ and L are a substituted or non-substituted aryl group having 6 to 50 ring carbon atoms, a substituted or non-substituted heterocyclic group having 5 to 50 ring atoms, a substituted or non-substituted alkyl group having 1 to 50 carbon atoms, a substituted or non-substituted cycloalkyl group having 3 to 50 carbon atoms, a substituted or non-substituted alkoxy group having 1 to 50 carbon atoms, a substituted or non-substituted aralkyl group having 7 to 50 carbon atoms, a substituted or non-substituted aryloxy group having 6 to 50 ring carbon atoms, a substituted or non-substituted heteroaryloxy group having 5 to 50 ring atoms, a substituted or non-substituted arylthio group having 6 to 50 ring carbon atoms, a substituted or non-substituted heteroarylthio group having 5 to 50 ring atoms, a substituted or non-substituted alkoxycarbonyl group having 2 to 50 carbon atoms, an amino group substituted with a substituted or non-substituted aryl group having 6 to 50 ring carbon atoms or a substituted or non-substituted heterocyclic group having 5 to 50 ring atoms, a halogen group, a cyano group, a nitro group, a hydroxyl group and the like.

The examples of the substituted or non-substituted aryl group having 6 to 50 ring carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4''-t-butyl-p-terphenyl-4-yl, fluoranthenyl, fluorenyl and the like.

The examples of the substituted or non-substituted heterocyclic group having 5 to 50 ring atoms include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The examples of the substituted or non-substituted alkyl group having 1 to 50 carbon atoms include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The examples of the substituted or non-substituted cycloalkyl group having 3 to 50 carbon atoms include cyclopropyl, cyclobutyl, cyclopentyl, cyclohexyl, 4-methylcyclohexyl, 1-adamantyl, 2-adamantyl, 1-norbornyl, 2-norbornyl and the like.

The substituted or non-substituted alkoxy group having 1 to 50 carbon atoms is a group represented by —OY. The examples of Y include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The examples of the substituted or non-substituted aralkyl group having 7 to 50 carbon atoms include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The substituted or non-substituted aryloxy group having 6 to 50 ring carbon atoms is represented by —OY', and the examples of Y' include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4''-t-butyl-p-terphenyl-4-yl and the like.

The substituted or non-substituted heteroaryloxy group having 5 to 50 ring atoms is represented by —OZ', and the examples of Z' include 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The substituted or non-substituted arylthio group having 6 to 50 ring carbon atoms is represented by —SY'', and the examples of Y'' include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4''-t-butyl-p-terphenyl-4-yl and the like.

The substituted or non-substituted heteroarylthio group having 5 to 50 ring atoms is represented by —SZ'', and the examples of Z'' include 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8- phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The substituted or non-substituted alkoxycarbonyl group having 2 to 50 carbon atoms is represented by —COOZ, and the examples of Z include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The amino group substituted with a substituted or non-substituted aryl group having 6 to 50 ring carbon atoms or a substituted or non-substituted heterocyclic group having 5 to 50 ring atoms is represented by —NPQ, and the examples of P and Q include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The specific examples of the compound represented by Formula (I) shall be shown below but shall not be restricted to them:

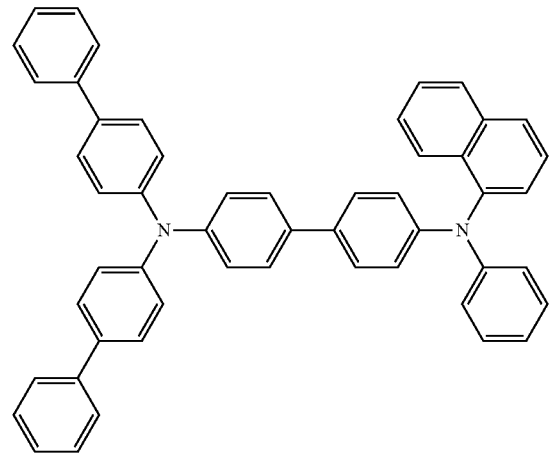

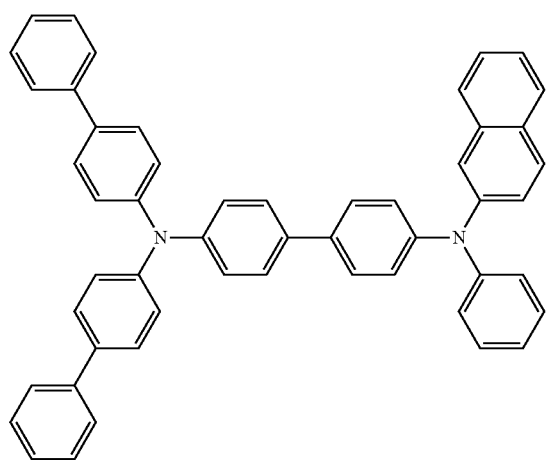
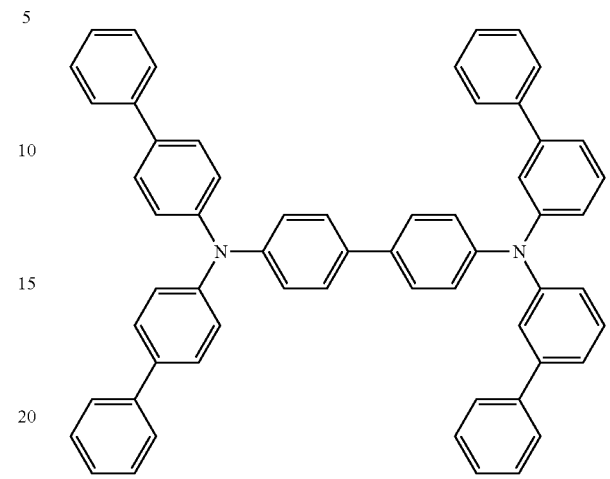
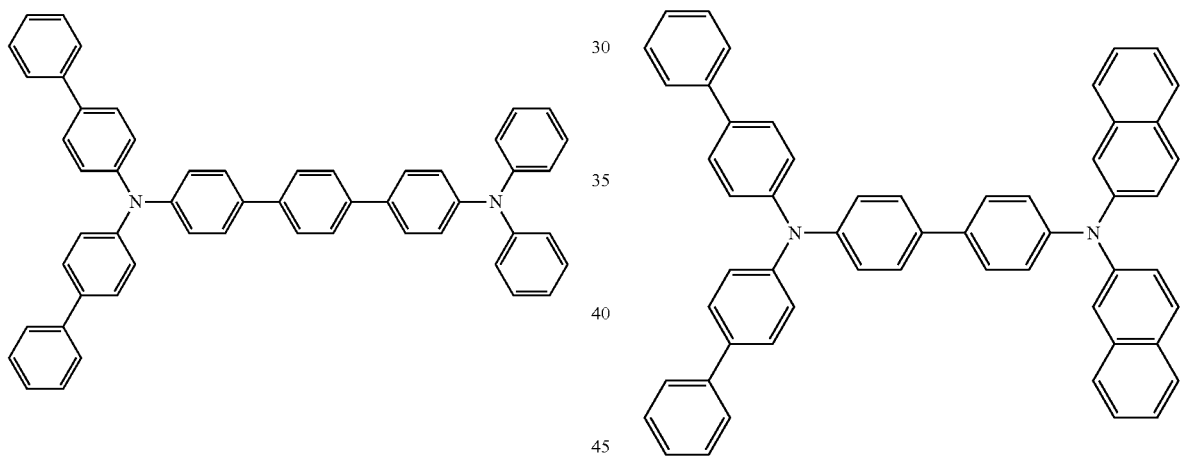
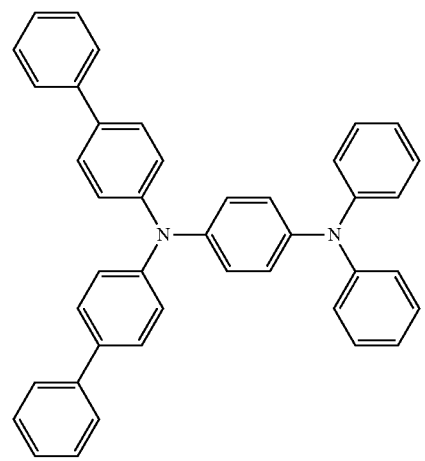

159
-continued
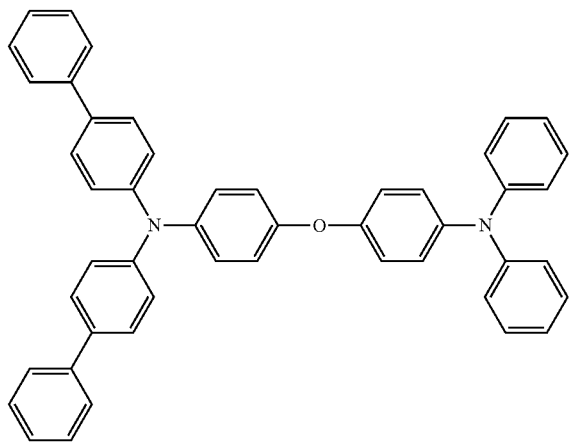
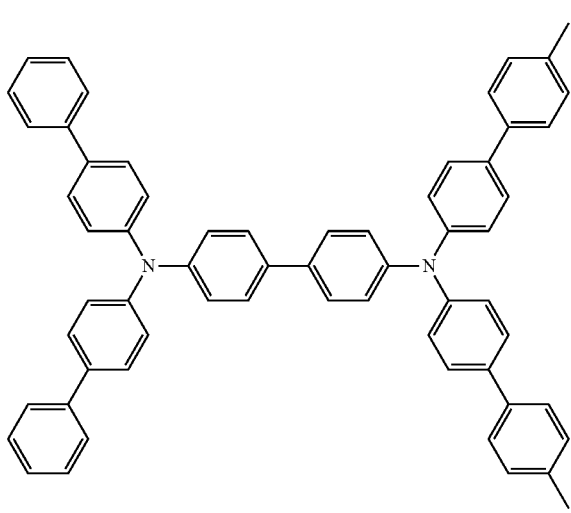
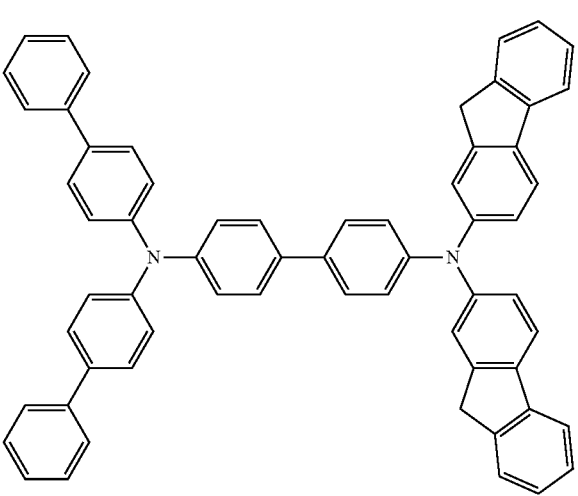
160
-continued
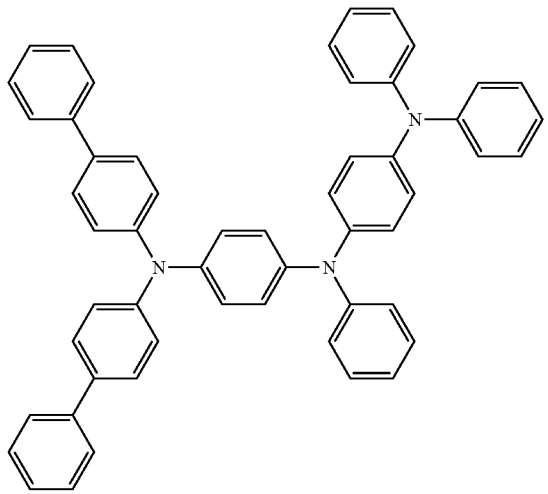
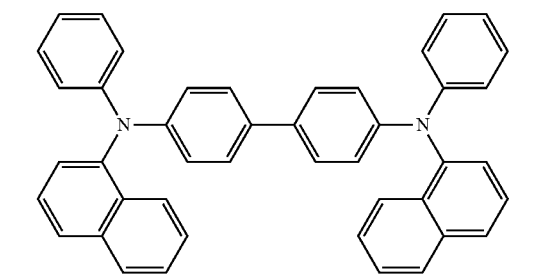
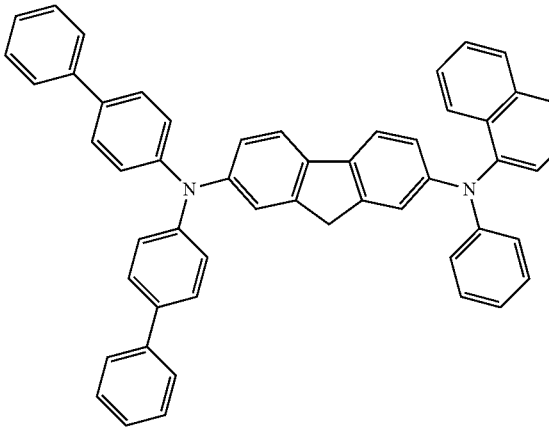
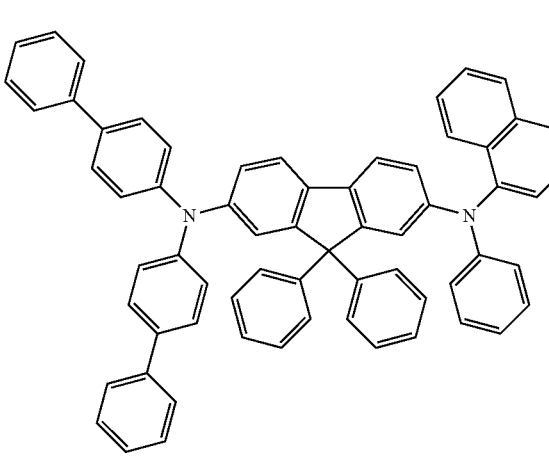

161
-continued
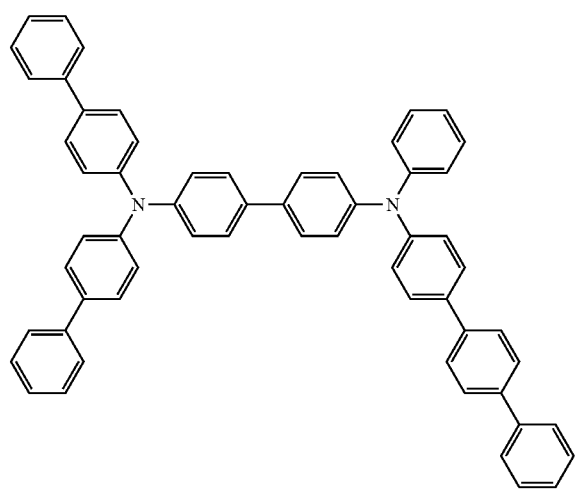
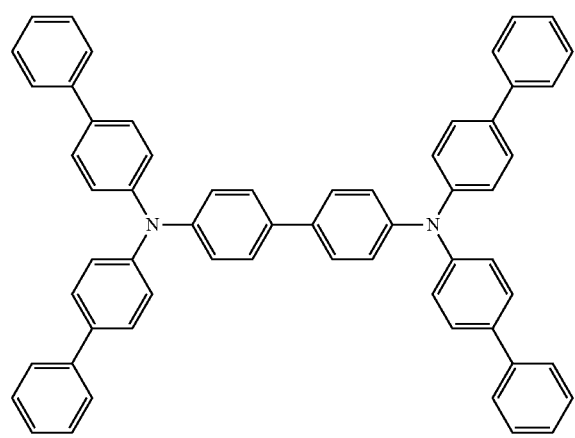
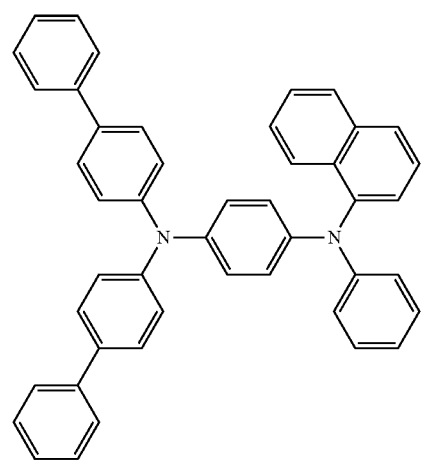
162
-continued
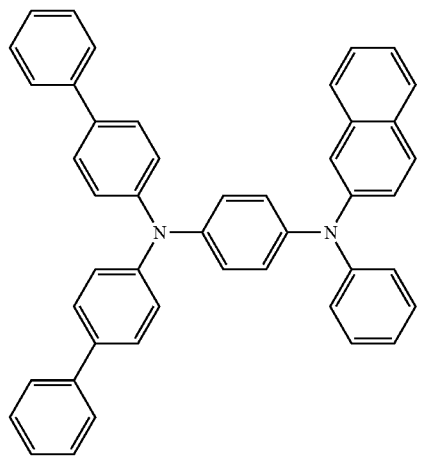
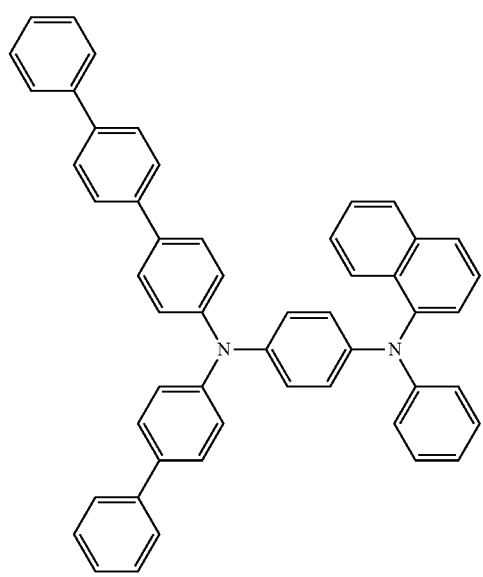
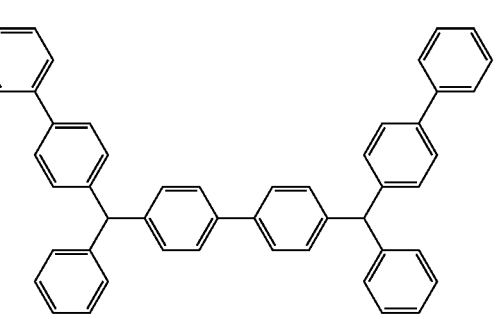

-continued

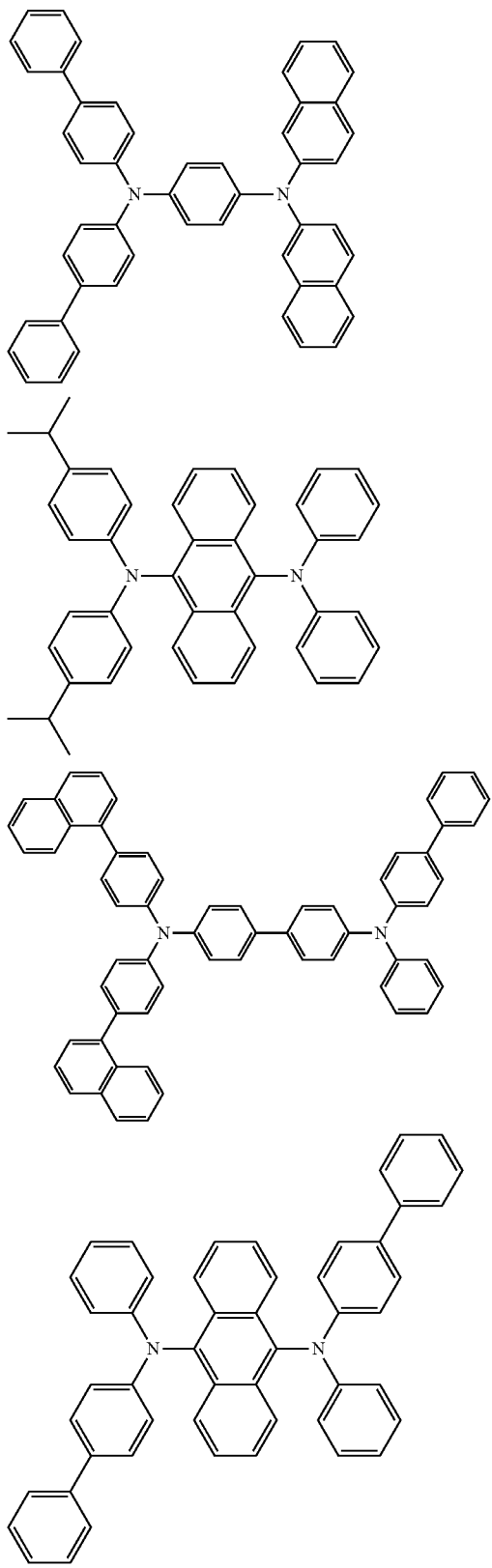

Further, an aromatic amine represented by Formula (II) shown below is suitably used as well for forming the hole injecting layer or the hole transporting layer:

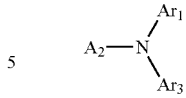
(II)

In Formula (II), the definitions of $Ar_1$ to $Ar_3$ are the same as those of $Ar^1$ to $Ar^4$ in Formula (I) described above. The specific examples of the compound represented by Formula (II) shall be shown below but shall not be restricted to them:

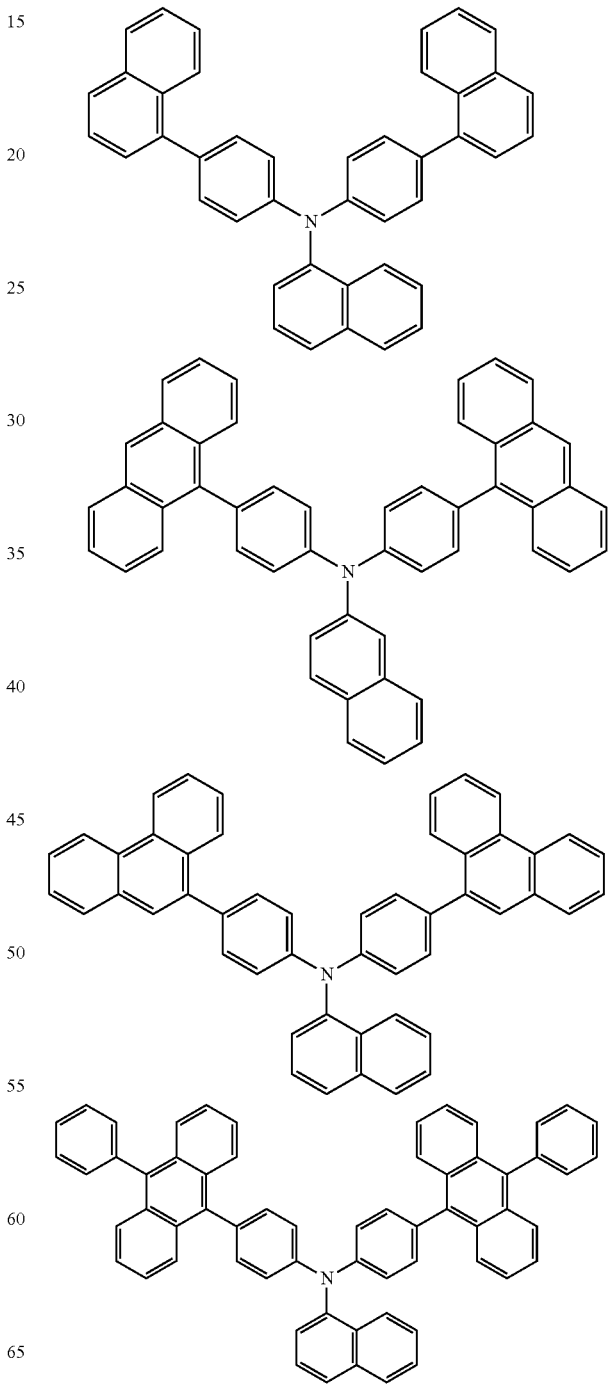

165
-continued
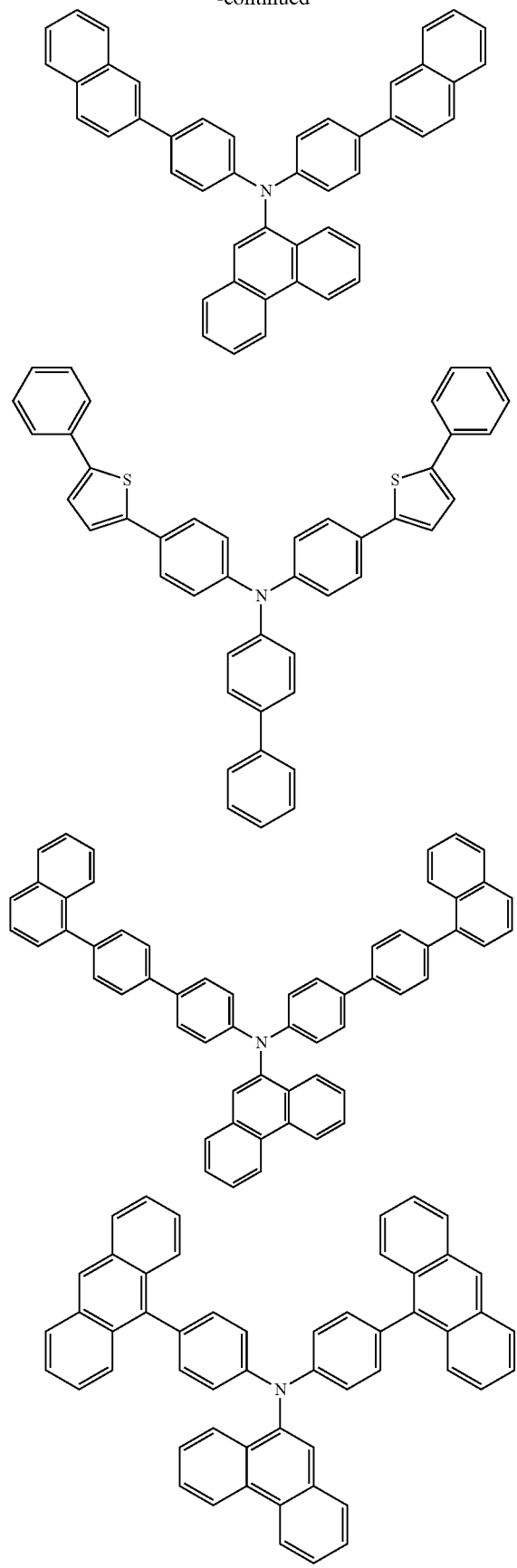
166
-continued
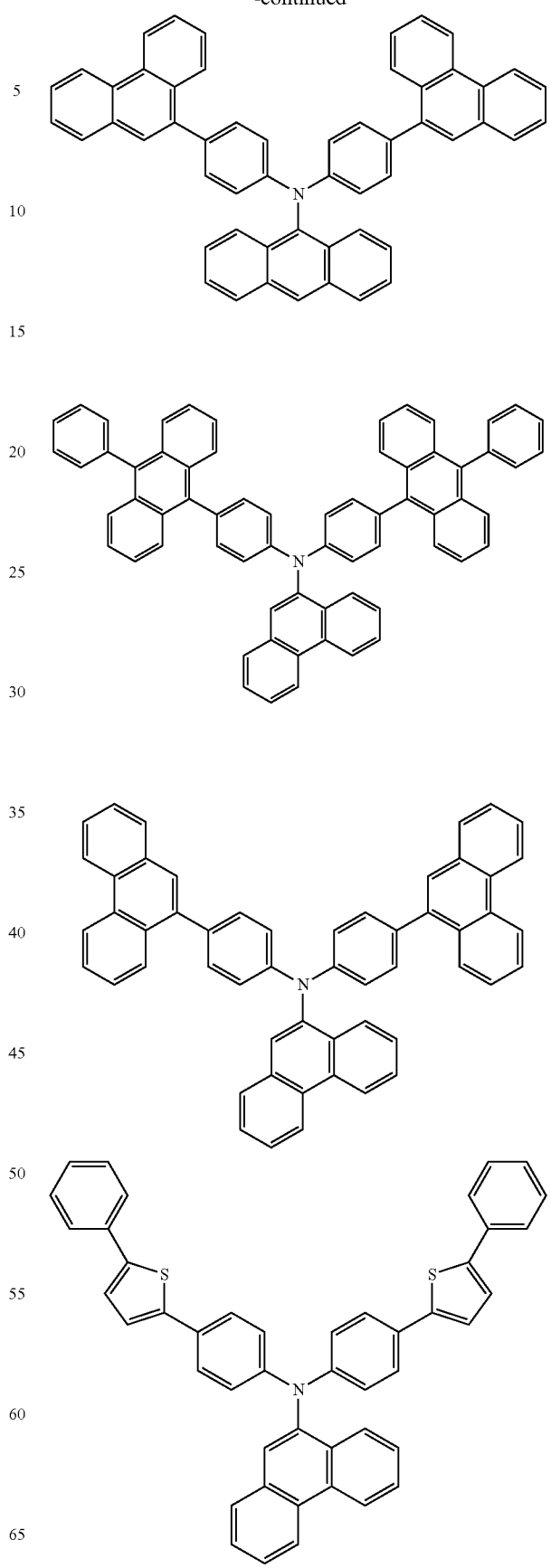

-continued

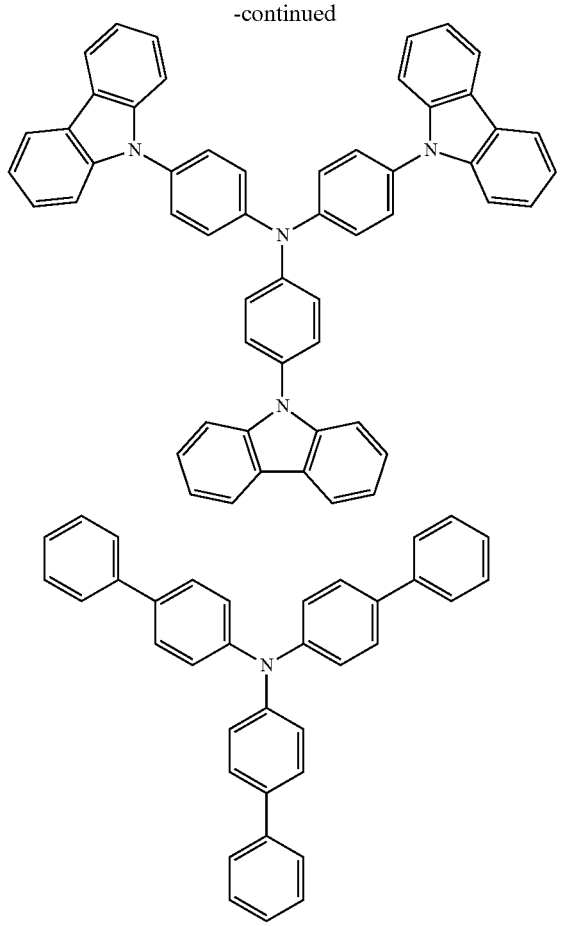

In the present invention, an anode of the organic EL device assumes a role of injecting holes into the hole transporting layer or the light emitting layer and has effectively a work function of 4.5 eV or more. Indium tin oxide alloy (ITO), tin oxide (NESA), gold, silver, platinum, copper and the like can be applied as the specific examples of the anode material used in the present invention. Also, a material of the cathode has preferably a small work function for the purpose of injecting electrons into the electron injecting layer or the light emitting layer. The cathode material shall not specifically be restricted, and capable of being used are, to be specific, indium, aluminum, magnesium, magnesium-indium alloy, magnesium-aluminum alloy, aluminum-lithium alloy, aluminum-scandium-lithium alloy, magnesium-silver alloy and the like.

The forming methods of the respective layers in the organic EL device of the present invention shall not specifically be restricted, and forming methods carried out by a vacuum vapor deposition method, a spin coating method and the like which have so far publicly been known can be used. The organic thin film layer containing the compound represented by Formula (1) described above which is used for the organic EL device of the present invention can be formed by a publicly known method carried out by a vacuum vapor deposition method, a molecular beam evaporation method (MBE method) and a coating method such as a dipping method, a spin coating method, a casting method, a bar coating method and a roll coating method each using a solution prepared by dissolving the compound in a solvent.

The film thicknesses of the respective organic layers in the organic EL device of the present invention shall not specifically be restricted, and in general, if the film thicknesses are too small, defects such as pinholes and the like are liable to be caused. On the other hand, if they are too large, a high voltage has to be applied, and the efficiency is deteriorated, so that they fall usually in a range of preferably several nm to 1 μm.

EXAMPLES

Next, the present invention shall be explained in further details with reference to synthetic examples and examples, but the present invention shall not be restricted to the synthetic examples and the examples shown below.

The evaluation methods of the organic EL device shall be described below.

(1) External Quantum Efficiency (%):

The external quantum efficiency in a luminance of 1000 cd/m$^2$ was measured at 23° C. under nitrogen gas atmosphere by means of a luminance meter (spectroradiometer CS-1000, manufactured by Konica Minolta Sensing, Inc.).

(2) Half Life (Hour):

A continuous power supply test (direct current) was carried out at an initial luminance of 1000 cd/m$^2$ to measure time passing until the initial luminance was reduced by half.

(3) Voltage (V):

A voltage was applied to the electrically wired device under dry nitrogen gas atmosphere by means of KEITHLY 236 SOURCE MEASURE UNIT to allow the device to emit light, and a voltage applied to wiring resistance other than the device was deducted to measure a voltage applied to the device.

Synthetic Example 1

Synthesis of Compound (1)

(1) Synthesis of Compound (1-a):

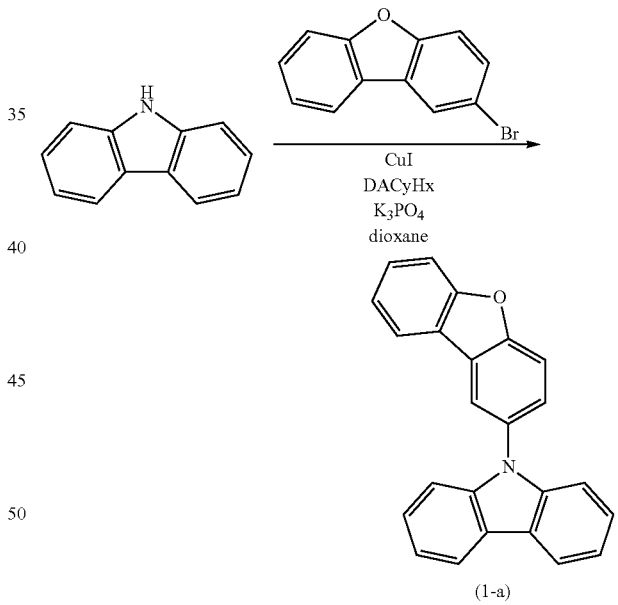

A three neck flask was charged with 40.1 g (240 mmol) of carbazole, 49.4 g (200 mmol) of 2-bromodibenzofuran, 3.81 g (20 mmol) of copper iodide, 84.91 g (400 mmol) of potassium phosphate, 7.21 ml (60 mmol) of trans-1,2-diaminocyclohexane and 100 ml of 1,4-dioxane under nitrogen atmosphere, and the mixture was refluxed for 24 hours. After finishing the reaction, the mixture was cooled down to room temperature and then diluted with 400 ml of toluene. The inorganic salts and the like were removed by filtration under reduced pressure, and the filtrate was passed through a short column of silica gel, and then concentrated. It was washed with an ethyl acetate/methanol mixed solvent to obtain a white solid matter (compound (1-a)). Amount: 54.0 g and yield: 81%

(2) Synthesis of Compound (1-b):

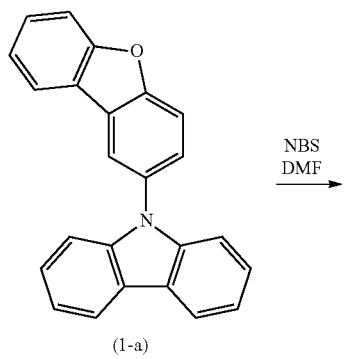

(1-a)

A Kjeldahl flask was charged with 26.7 g (80 mmol) of the compound (1-a) and 160 ml of N,N-dimethylformamide under air to dissolve the sample, and the flask was cooled down to 0° C. on an ice and water bath. To a solution, N-bromosuccinimide 14.2 g (80 mmol) dissolved in 80 ml of N,N-dimethylformamide was slowly dropwise added over a 10 minutes. The solution was stirred at 0° C. for 3 hours and then left standing at room temperature for a night. After finishing the reaction, 200 ml of toluene was added thereto, and the solution was washed twice with water by means of a separating funnel. It was dried on anhydrous magnesium sulfate and then filtrated and concentrated. The concentrate was recrystallized from hexane to obtain a white solid matter (compound (1-b)). Amount: 25.6 g and yield: 78%

(3) Synthesis of Compound (1-c):

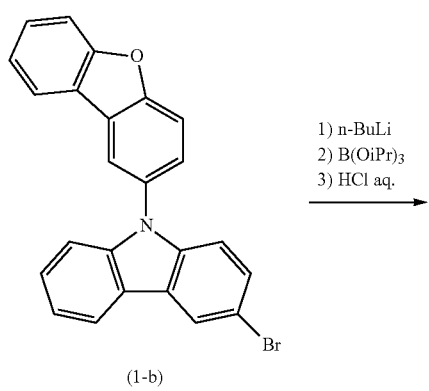

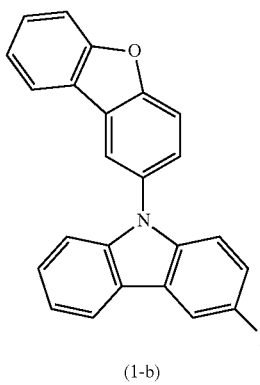

(1-b)

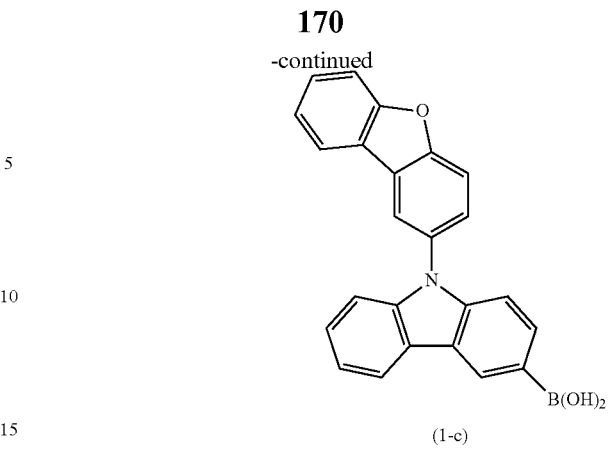

A three neck flask was charged with 16.5 g (40 mmol) of the compound (1-b) and 200 ml of dehydrated tetrahydrofuran under nitrogen atmosphere to dissolve the sample, and the flask was cooled down to −78° C. To a solution, n-Butyllithium 30.6 ml (1.57M in hexane, 48 mmol) was dropwise added over 10 minutes. The solution was stirred at −78° C. for 20 minutes, and then 18.3 ml (80 mmol) of triisopropyl borate was added thereto in one lot, followed by stirring the solution at room temperature for 3 hours.

After finishing the reaction, the solution was concentrated to about a half, and 20 ml of a hydrochloric acid aqueous solution (1N) was added thereto, followed by stirring the solution at room temperature for 2 hours. The solution was extracted with dichloromethane by means of a separating funnel, and the extract was dried on anhydrous magnesium sulfate, filtrated and concentrated. The concentrate was purified by silica gel chromatography (dichloromethane:ethyl acetate=9:1 as eluent), and then hexane was added thereto to precipitate a sample. The sample was suspended and filtered off to give a white solid matter (compound (1-c)). Amount: 10.3 g and yield: 68%

(4) Synthesis of Compound (1):

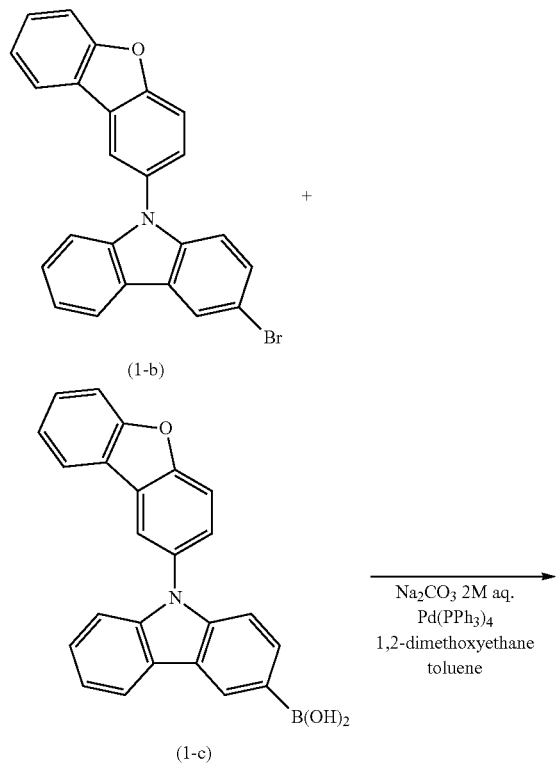

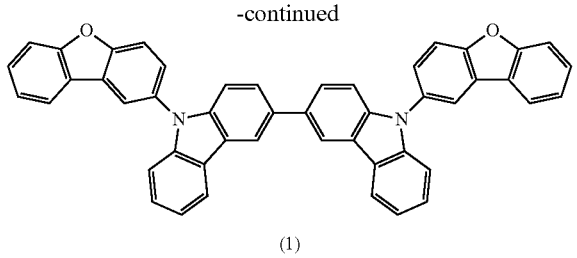

(1)

A three neck flask was charged with 9.11 g (22.1 mmol) of the compound (1-b), 10.0 g (26.5 mmol) of the compound (1-c), 22.1 ml of a sodium carbonate 2M aqueous solution, 40 ml of 1,2-dimethoxyethane and 40 ml of toluene, and 0.51 g (0.442 mmol) of tetrakis(triphenylphosphine)palladium was added to the above mixed solution, followed by refluxing the solution for 8 hours.

After finishing the reaction, the solution was cooled down to room temperature, and then methanol was added thereto to recover a precipitated sample and dry it under vacuum. The sample was dissolved in 1 L of toluene by heating, and the solution was cooled down to room temperature. Then, it was allowed to pass through a short column of silica gel and concentrated. The concentrate was subjected to disperse washing with ethyl acetate to obtain a white solid matter (compound (1)). Amount: 12.0 g and yield: 81%

Synthetic Example 2

Synthesis of Compound (3)

(1) Synthesis of Compound (3-a):

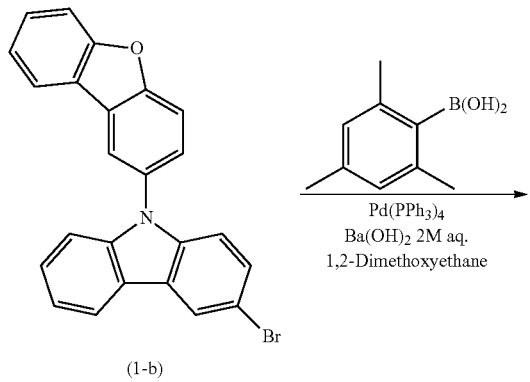

(3-a)

A three neck flask was charged with 41.2 g (100 mmol) of the compound (1-b), 23.0 g (140 mmol) of mesityl boronic acid, 200 ml of a barium hydroxide 2M aqueous solution and 50 ml of 1,2-dimethoxyethane under nitrogen atmosphere, and 3.47 g (3 mmol) of tetrakis(triphenylphosphine)palladium was added to the above mixed solution, followed by refluxing the solution for 8 hours.

After finishing the reaction, the solution was cooled down to room temperature, and then the solution was extracted with toluene by means of a separating funnel. The extract was dried on anhydrous magnesium sulfate, filtrated and concentrated, and then the concentrate was purified by silica gel chromatography (toluene:hexane=3:7). This was recrystallized from hexane to obtain a white solid matter (compound (3-a)). Amount: 15.3 g and yield: 34%

(2) Synthesis of Compound (3)

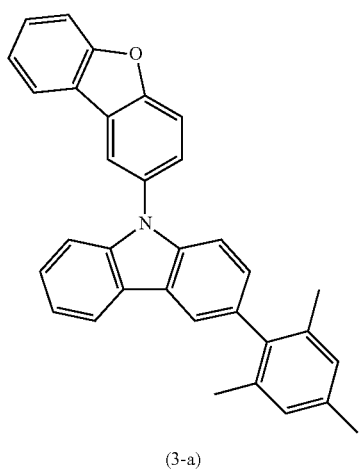

(3-a)

(3-b)

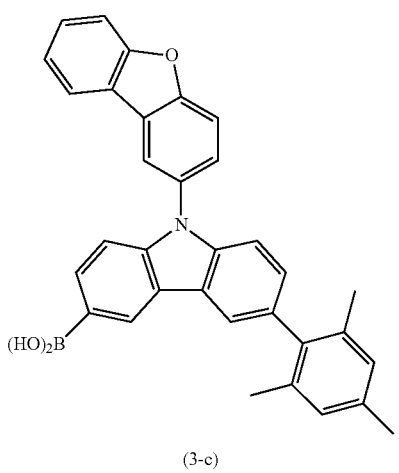

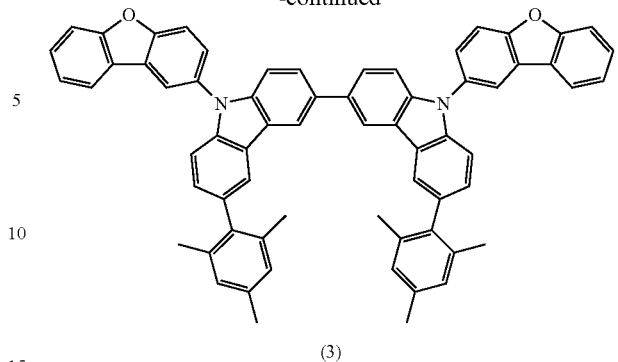

A compound (3) was synthesized by the same method as in the compounds (1-b) to (1), except that the raw material was changed from the compound (1-a) to the compound (3-a).

Synthetic Example 3

Synthesis of Compound (36)

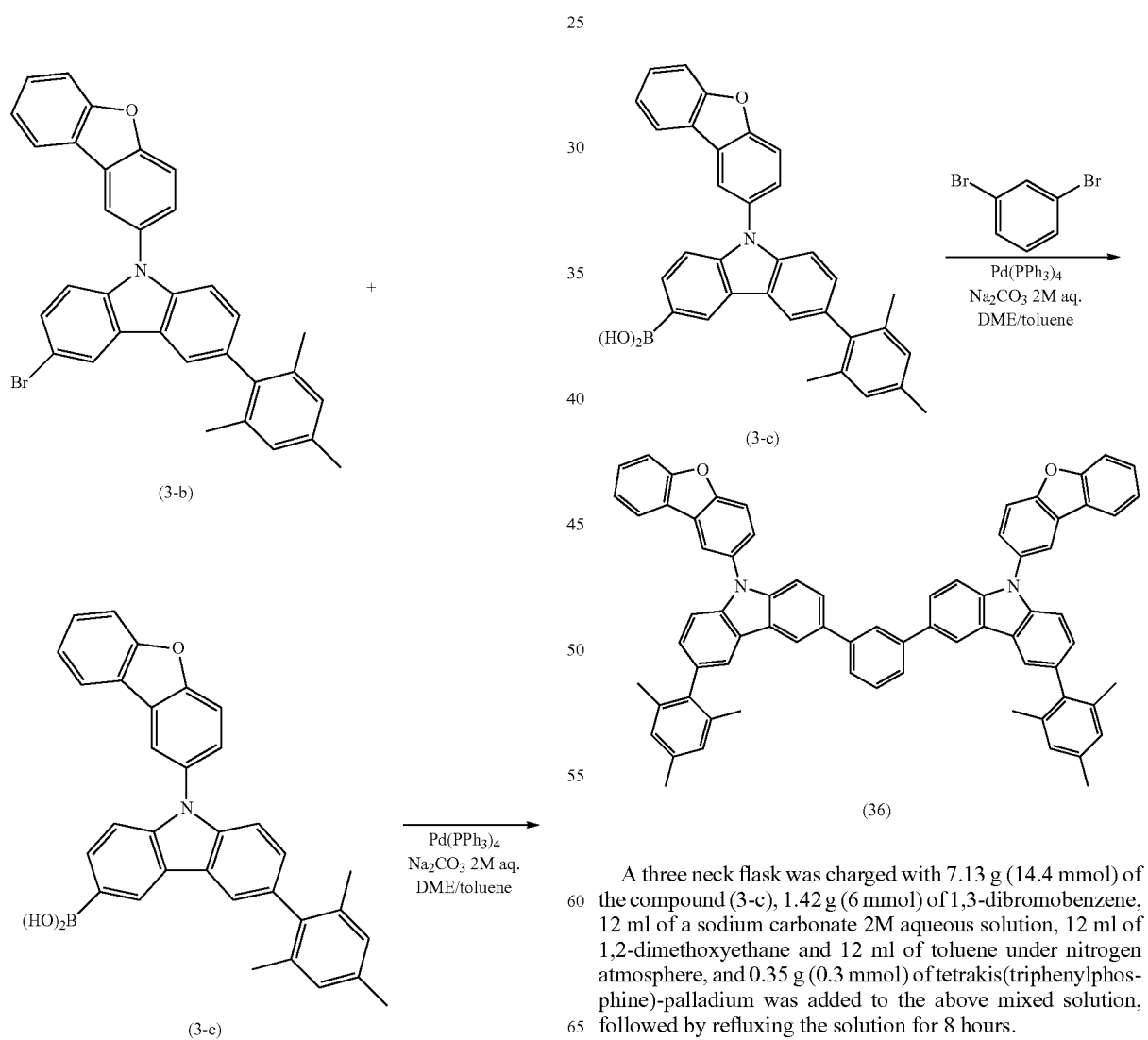

A three neck flask was charged with 7.13 g (14.4 mmol) of the compound (3-c), 1.42 g (6 mmol) of 1,3-dibromobenzene, 12 ml of a sodium carbonate 2M aqueous solution, 12 ml of 1,2-dimethoxyethane and 12 ml of toluene under nitrogen atmosphere, and 0.35 g (0.3 mmol) of tetrakis(triphenylphosphine)-palladium was added to the above mixed solution, followed by refluxing the solution for 8 hours.

After finishing the reaction, the solution was cooled down to room temperature, and then the sample solution was transferred into a separating funnel and extracted several times with toluene. The extract was dried on anhydrous magnesium sulfate, then filtrated and concentrated, and the concentrate was purified by silica gel chromatography to obtain a white solid matter (compound (36)). Amount: 4.3 g and yield: 73%.

The above compounds were subjected to measurement of FD/MS and identified by an agreement of the theoretical values of the molecular weights with the actual measured values thereof.

Comparative Synthetic Example

Synthesis of Compound (33)

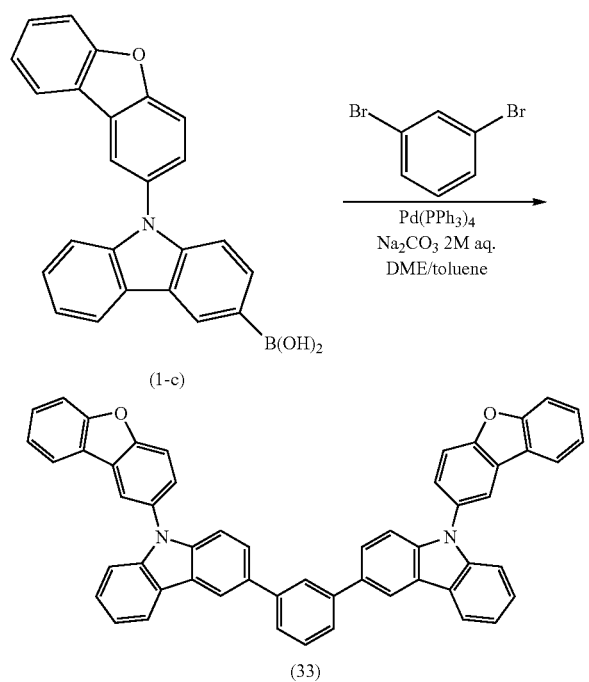

A three neck flask was charged with 5.43 g (14.4 mmol) of the compound (1-c), 1.42 g (6 mmol) of 1,3-dibromobenzene, 12 ml of a sodium carbonate 2M aqueous solution, 12 ml of 1,2-dimethoxyethane and 12 ml of toluene under nitrogen atmosphere, and 0.35 g (0.3 mmol) of tetrakis(triphenylphosphine)-palladium was added to the above mixed solution, followed by refluxing the solution for 8 hours.

After finishing the reaction, the solution was cooled down to room temperature, and then methanol was added thereto to recover a precipitated sample and dry it under vacuum. The sample was dissolved in 1 L of toluene by heating, and the solution was cooled down to room temperature. Then, it was allowed to pass through a short column of silica gel and concentrated. The concentrate was subjected to disperse washing with a mixed solvent of ethyl acetate/hexane to obtain a white solid matter (compound (33)). Amount: 3.78 g and yield: 85%

Example 1

A glass substrate (manufactured by Geomatech Co., Ltd.) of 25 mm×75 mm×1.1 mm equipped with an ITO transparent electrode was subjected to sonication in isopropyl alcohol for 5 minutes and then to UV ozone treatment for 30 minutes. After the treatment, the glass substrate equipped with an ITO transparent electrode line was loaded in a substrate holder of a vacuum vapor deposition apparatus, and a compound (HT) was subjected to resistance heating vapor deposition (thickness: 60 nm) on a face of a side on which the transparent electrode line was formed so that it covered the transparent electrode. The film-deposition rate was set to 1 Å/s. The above HT film functions as a hole injecting-transporting layer.

Next, the compound (1) (host compound) was subjected to resistance heating vapor deposition on the HT film to form a compound (1) film having a thickness of 30 nm. Simultaneously, a compound (BD) as a phosphorescent dopant was deposited so that the compound (BD) accounted for 10% in terms of a mass ratio based the compound (1). The film-deposition rates were set to 1 Å/s and 0.11 Å/s respectively. The above film functions as a phosphorescent layer.

Next, a compound (HB) was subjected to resistance heating vapor deposition on the above phosphorescent emitting layer to form an HB film having a thickness of 10 nm. The film-deposition rate was 1 Å/s. The above HB film functions as a hole blocking layer.

A tris(8-quinolinol)aluminum (Alq) complex was deposited (film thickness: 30 nm) at a film-deposition rate of 1 Å/s on the above film. This film functions as an electron injecting layer.

Then, LiF was deposited (film thickness: 0.5 nm) at a film-deposition rate of 0.1 Å/s on the Alq film. Metal Al was deposited at a film-deposition rate of 1 Å/s on the above LiF film to form a metal cathode (film thickness: 100 nm), and an organic EL device was obtained.

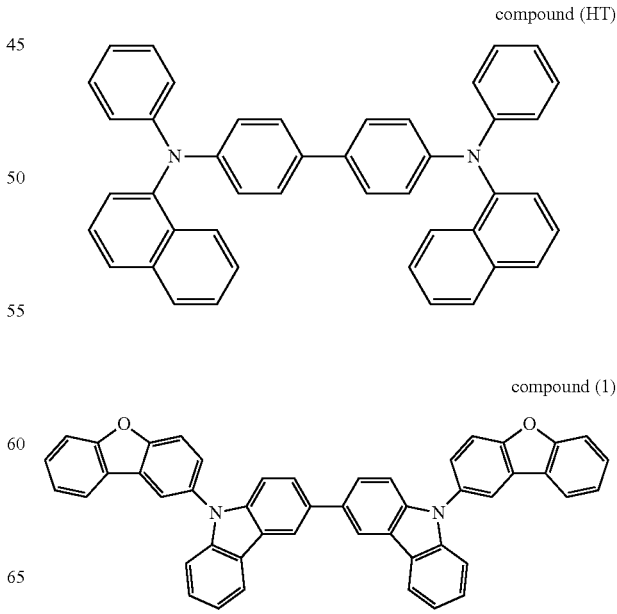

compound (BD)

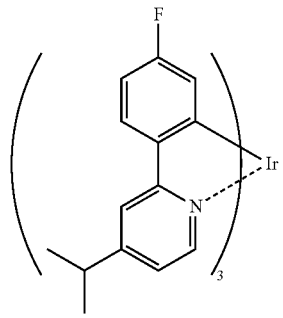

compound (HB)

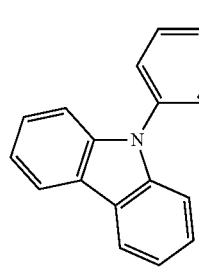

Alq

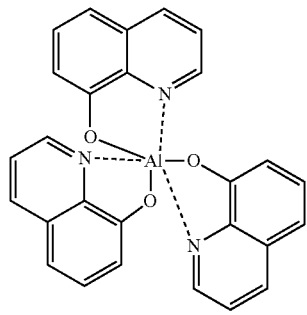

compound (3)

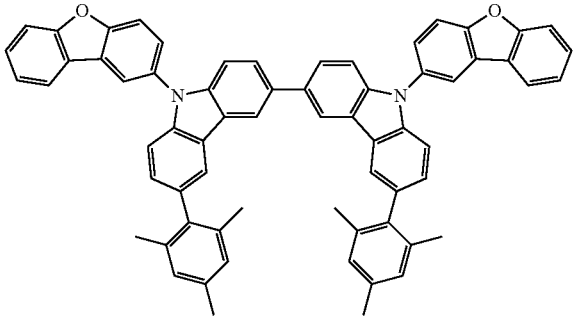

compound (33)

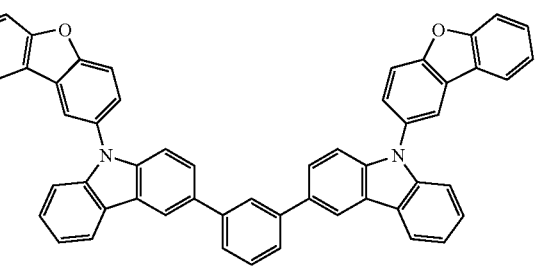

compound (36)

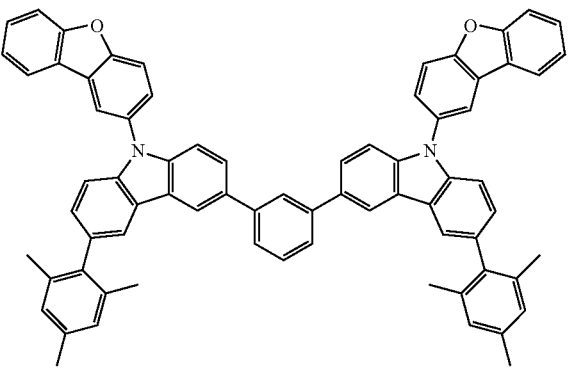

Examples 2 and 3

Organic EL devices were prepared in the same manner as in Example 1, except that host materials described in Table 1 were used in place of the compound (1) in Example 1.

Comparative Examples 1 to 6

Organic EL devices were prepared in the same manner as in Example 1, except that the following compounds (H1) to (H6) were used in place of the compound (1).

compound (H1)
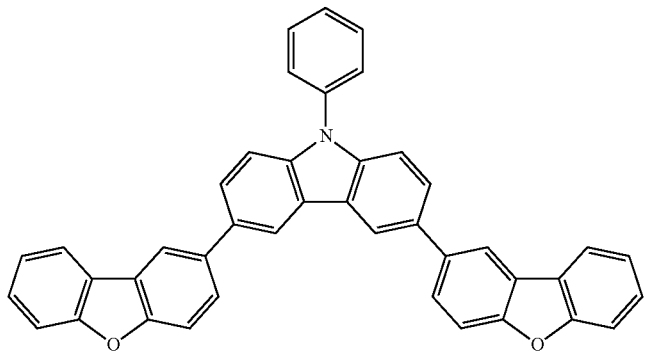
compound (H2)
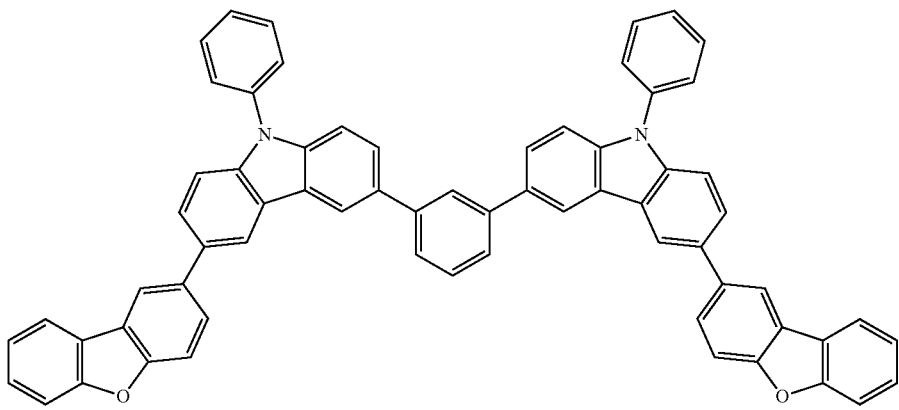
compound (H4)                                   compound (H5)
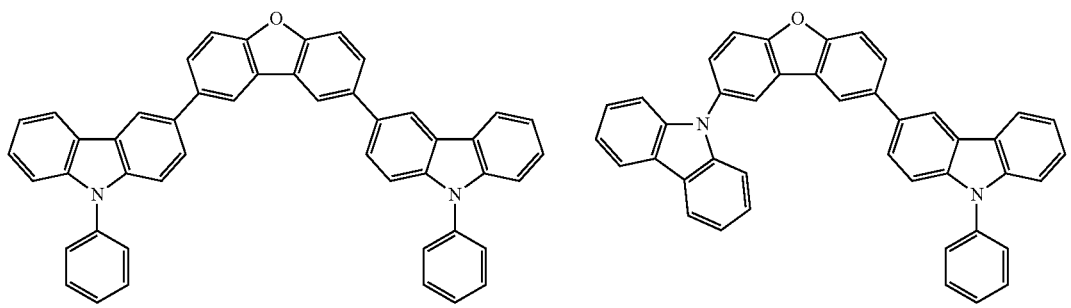
compound (H6)
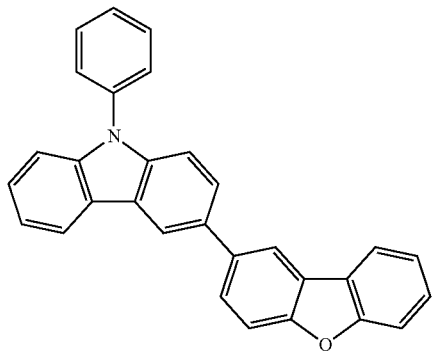

TABLE 1

| | Host | Voltage (V) | External quantum efficiency (%) | Half life (hour) |
|---|---|---|---|---|
| Example 1 | (1) | 7.4 | 6.3 | 1050 |
| Example 2 | (3) | 7.6 | 11.1 | 1190 |
| Example 3 | (36) | 7.4 | 9.2 | 1010 |
| Comparative Example 1 | H1 | 8.8 | 7.0 | 700 |
| Comparative Example 2 | H2 | 8.8 | 7.1 | 650 |
| Comparative Example 3 | H4 | 9.3 | 6.4 | 450 |
| Comparative Example 4 | H5 | 9.5 | 6.9 | 480 |
| Comparative Example 5 | H6 | 9.3 | 6.9 | 250 |
| Comparative Example 6 | (33) | 8.3 | 7.2 | 1000 |

It can be found from the results shown in Table 1 that the compounds (1), (3) and (36) of the present invention have higher efficiencies and longer lifetimes than those of the compounds used in Comparative Examples 1 to 5. Further, it can be found that since the organic EL devices of the present invention can be operated at lower voltages, they are organic EL devices which are reduced in power consumption.

In Table 1, Comparative Example 6 is not comparable to the other examples in terms of a reduced voltage and a half life. This is considered to be due to that it is not comparable to the other examples in terms of a chemical stability and control of a carrier balance attributable to that all of 6-positions of carbazoles are hydrogen atoms and that they are not bonded at 3-positions via single bonds.

Example 4

A glass substrate (manufactured by Geomatech Co., Ltd.) of 25 mm×75 mm×1.1 mm equipped with an ITO transparent electrode was subjected to sonication in isopropyl alcohol for 5 minutes and then to UV ozone treatment for 30 minutes. After the treatment, the glass substrate equipped with an ITO transparent electrode line was loaded in a substrate holder of a vacuum vapor deposition apparatus, and the compound (1) was subjected to resistance heating vapor deposition (thickness: 60 nm) on a face of a side on which the transparent electrode line was formed so that it covered the transparent electrode. The film-deposition rate was set to 1 Å/s. The above compound (1) film functions as a hole injecting-transporting layer.

Next, a compound (A-1) (host compound) was subjected to resistance heating vapor deposition on the compound (1) film to form a compound (A-1) film having a thickness of 30 nm. Simultaneously, the compound (BD) as a phosphorescent dopant was deposited so that the compound (BD) accounted for 10% in terms of a mass ratio based the compound (A-1). The film-deposition rates were set to 1 Å/s and 0.11 Å/s respectively. The above film functions as a phosphorescent emitting layer.

Next, the compound (HB) (host compound) was subjected to resistance heating vapor deposition on the above phosphorescent layer to form an HB film having a thickness of 10 nm. The film-deposition rate was 1 Å/s. The above HB film functions as a hole blocking layer.

A tris(8-quinolinol)aluminum (Alq) complex was deposited (film thickness: 30 nm) on the above film. This film functions as an electron injecting layer.

Then, LiF was deposited (film thickness: 0.5 nm) on the Alq film at a film-deposition rate of 0.1 Å/s. Metal Al was deposited on the above LiF film at a film-forming rate of 1 Å/s to form a metal cathode (film thickness: 100 nm), and an organic EL device was obtained.

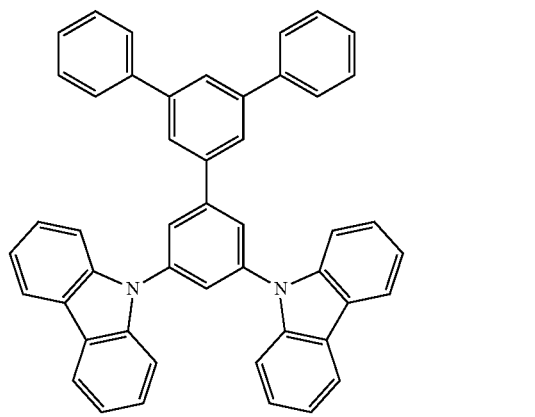

compound (A-1)

Example 5

An organic EL device was prepared in the same manner as in Example 4, except that the compound (3) was used for the hole injecting-transporting layer in place of the compound (1) in Example 4.

Comparative Example 7

An organic EL device was prepared in the same manner as in Example 4, except that the compound (HT) was used in place of the compound (1).

TABLE 2

| | Hole injecting-transporting layer | Voltage (V) | External quantum efficiency (%) | Half life (hour) |
|---|---|---|---|---|
| Example 4 | (1) | 8.3 | 10.4 | 1000 |
| Example 5 | (3) | 8.5 | 10.2 | 1030 |
| Comparative Example 7 | HT | 7.3 | 5.5 | 420 |

It can be found from the results shown in Table 2 that the compounds (1) and (3) of the present invention have lower voltages, higher efficiencies and longer lifetimes than that of the compound used in the comparative example.

INDUSTRIAL APPLICABILITY

As explained above in detail, use of the materials for an organic EL device according to the present invention provides organic EL devices having a high light emission efficiency and a long lifetime. Accordingly, the organic EL devices of the present invention are very useful as displays for various electronic equipment, light sources and the like.

What is claimed is:

1. A material for an organic electroluminescence device represented by formula (2):

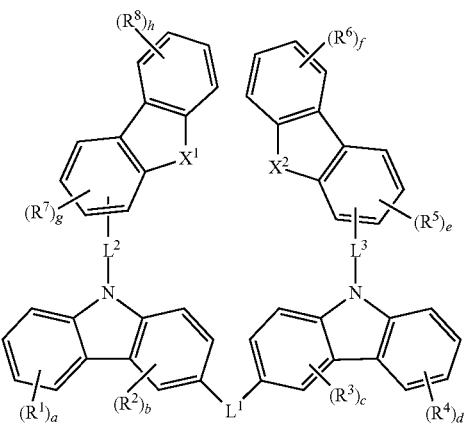

(2)

wherein
$X^1$ and $X^2$ are each an oxygen atom;
$R^1$ to $R^8$ each independently represent a hydrogen atom or an aryl group having 6 to 18 ring carbon atoms;
a, d, f and h are each independently 0 or 1;
b, c, e and g are each 0;
$L^1$ represents a single bond; and
$L^2$ and $L^3$ each independently represent a single bond, p-phenylene or m-phenylene.

2. The material for an organic electroluminescence device according to claim 1, wherein $L^2$ and $L^3$ are single bonds.

3. The material for an organic electroluminescence device according to claim 1, which is represented by formula (3):

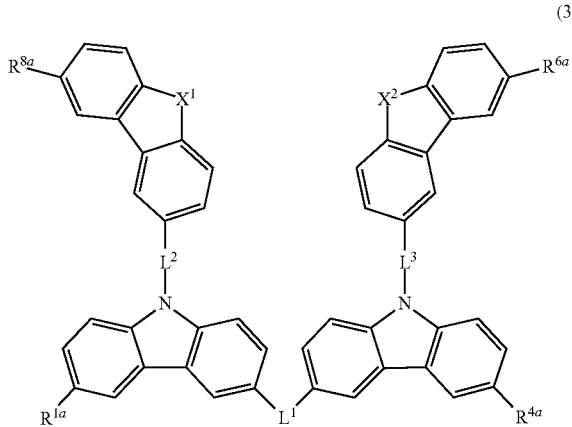

(3)

wherein
$R^{1a}$, $R^{4a}$, $R^{6a}$ and $R^{8a}$ each represent independently a hydrogen atom or an aryl group having 6 to 18 ring carbon atoms; and
$X^1$, $X^2$ and $L^1$ to $L^3$ are as defined in claim 1.

4. The material for an organic electroluminescence device according to claim 1, wherein a triplet energy level of the material is 2.0 eV or more.

5. The material for an organic electroluminescence device according to claim 1, wherein each of $R^1$ to $R^8$ represents phenyl, tolyl, xylyl or mesityl.

6. The material for an organic electroluminescence device according to claim 1, wherein a, b, c, d, e, f, g and h each represent 0.

7. The material for an organic electroluminescence device according to claim 1, which is represented by the formula

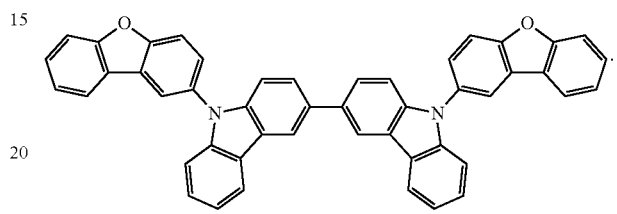

8. An organic electroluminescence device provided with one or more organic thin film layers including a light emitting layer between a cathode and an anode, wherein at least one layer of the above organic thin film layers contains the material for an organic electroluminescence device according to claim 1.

9. The organic electroluminescence device according to claim 8, wherein the light emitting layer contains the material for an organic electroluminescence device described above as a host material.

10. The organic electroluminescence device according to claim 8, wherein the light emitting layer contains a host material and a phosphorescence luminescence material, and the above host material is the material for an organic electroluminescence device described above.

11. The organic electroluminescence device according to claim 10, wherein the phosphorescence luminescence material is a compound containing metal selected from iridium (Ir), osmium (Os) and platinum (Pt).

12. The organic electroluminescence device according to claim 11, wherein the compound containing metal is an ortho-metallization metal complex.

13. The organic electroluminescence device according to claim 8, wherein an electron injecting layer is provided between the light emitting layer and the cathode, and the above electron injecting layer contains a nitrogen-containing heterocyclic derivative.

14. The organic electroluminescence device according to claim 8, wherein a hole transporting layer is provided between the light emitting layer and the anode, and the above hole transporting layer contains the material for an organic electroluminescence device described above.

* * * * *